US012778901B2

(12) United States Patent
Kealey

(10) Patent No.: US 12,778,901 B2
(45) Date of Patent: Nov. 3, 2026

(54) SCAFFOLDS TO TREAT SOLID TUMOR CELLS AND ESCAPE VARIANTS

(71) Applicant: Monarch Biosciences, Inc., Los Angeles, CA (US)

(72) Inventor: Colin Patrick Kealey, Los Angeles, CA (US)

(73) Assignee: Monarch Biosciences, Inc., Los Angeles, CA (US)

(*) Notice: Subject to any disclaimer, the term of this patent is extended or adjusted under 35 U.S.C. 154(b) by 353 days.

(21) Appl. No.: 17/846,391

(22) Filed: Jun. 22, 2022

(65) Prior Publication Data

US 2022/0339195 A1 Oct. 27, 2022

Related U.S. Application Data

(63) Continuation of application No. 16/472,764, filed as application No. PCT/US2017/067965 on Dec. 21, 2017, now abandoned.

(60) Provisional application No. 62/437,572, filed on Dec. 21, 2016.

(51) Int. Cl.

| | |
|---|---|
| ***A61K 9/70*** | (2006.01) |
| ***A61K 38/17*** | (2006.01) |
| ***A61K 38/20*** | (2006.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61K 45/06*** | (2006.01) |
| ***A61K 47/34*** | (2017.01) |
| ***A61L 31/00*** | (2006.01) |
| ***A61L 31/04*** | (2006.01) |
| ***A61L 31/06*** | (2006.01) |
| ***A61L 31/14*** | (2006.01) |
| ***A61L 31/16*** | (2006.01) |
| ***A61P 35/00*** | (2006.01) |
| ***A61P 35/04*** | (2006.01) |
| ***C12N 5/0783*** | (2010.01) |

(52) U.S. Cl.

CPC .............. *A61K 9/70* (2013.01); *A61K 38/177* (2013.01); *A61K 38/1774* (2013.01); *A61K 38/2086* (2013.01); *A61K 40/11* (2025.01); *A61K 40/31* (2025.01); *A61K 40/4224* (2025.01); *A61K 45/06* (2013.01); *A61K 47/34* (2013.01); *A61L 31/005* (2013.01); *A61L 31/042* (2013.01); *A61L 31/046* (2013.01); *A61L 31/06* (2013.01); *A61L 31/146* (2013.01); *A61L 31/16* (2013.01); *A61P 35/00* (2018.01); *A61P 35/04* (2018.01); *C12N 5/0636* (2013.01); *C12N 5/0638* (2013.01); *A61K 2039/54* (2013.01); *A61K 2039/575* (2013.01); *A61K 2239/31* (2023.05); *A61K 2239/54* (2023.05); *A61L 2300/416* (2013.01); *A61L 2300/606* (2013.01); *C12N 2501/06* (2013.01); *C12N 2501/998* (2013.01); *C12N 2501/999* (2013.01); *C12N 2510/00* (2013.01); *C12N 2533/00* (2013.01); *C12N 2533/74* (2013.01)

(58) Field of Classification Search

None

See application file for complete search history.

(56) References Cited

U.S. PATENT DOCUMENTS

| | | | | |
|---|---|---|---|---|
| 2001/0000647 | A1 | 5/2001 | Akram | |
| 2002/0062154 | A1 | 5/2002 | Ayers | |
| 2006/0067909 | A1 | 3/2006 | West et al. | |
| 2010/0060175 | A1 | 3/2010 | Lethellier | |
| 2010/0208502 | A1 | 8/2010 | Horii | |
| 2012/0245706 | A1 | 9/2012 | Alavi et al. | |
| 2014/0079774 | A1 | 3/2014 | Brinker et al. | |
| 2014/0180399 | A1 | 6/2014 | Alavi et al. | |
| 2014/0334205 | A1 | 11/2014 | Zhang | |
| 2015/0372601 | A1 | 12/2015 | Shiu et al. | |
| 2016/0008399 | A1 | 1/2016 | Stephan | |
| 2016/0079790 | A1 | 3/2016 | Kleinpenning et al. | |
| 2016/0235564 | A1 | 8/2016 | Johnson et al. | |
| 2016/0261204 | A1 | 9/2016 | Kikuchi et al. | |
| 2016/0287623 | A1 | 10/2016 | Gajewski et al. | |
| 2016/0294180 | A1 | 10/2016 | Pagano et al. | |
| 2017/0340658 | A1* | 11/2017 | Vernejoul | A61P 35/00 |
| 2018/0006569 | A1 | 1/2018 | Kikuchi | |
| 2018/0062510 | A1 | 3/2018 | Trescases et al. | |
| 2018/0138797 | A1 | 5/2018 | Tsu et al. | |
| 2018/0175738 | A1 | 6/2018 | Kukuchi | |

(Continued)

FOREIGN PATENT DOCUMENTS

| | | | | |
|---|---|---|---|---|
| WO | WO-2014110591 | A1 * | 7/2014 | A01K 67/0271 |
| WO | WO 2016/096577 | A1 | 6/2016 | |

(Continued)

OTHER PUBLICATIONS

Shabalovskaya et al. “Critical overview of Nitinol surfaces and their modifications for medical applications.” Acta Biomaterialia 4.3 ( 2008): 447-467. (Year: 2008).*

(Continued)

*Primary Examiner* — Emily A Cordas

(74) *Attorney, Agent, or Firm* — Haynes and Boone, LLP

(57) ABSTRACT

Implantable scaffolds that treat solid tumors and escape variants and that provide effective vaccinations against cancer recurrence are described. The scaffolds include genetically-reprogrammed lymphocytes and a lymphocyte-activating moiety.

10 Claims, 37 Drawing Sheets

(1 of 37 Drawing Sheet(s) Filed in Color)

Specification includes a Sequence Listing.

(56) References Cited

U.S. PATENT DOCUMENTS

2018/0351462 A1 12/2018 Li et al.
2018/0367045 A1 12/2018 Zhang et al.
2019/0149056 A1 5/2019 Zheng
2019/0222132 A1 7/2019 Kikuchi
2019/0229635 A1 7/2019 Hyugaji et al.
2019/0326903 A1 10/2019 Yoshida
2019/0336532 A1 11/2019 Stephan et al.
2020/0112264 A1 4/2020 Arima et al.
2021/0091654 A1 3/2021 Rajesh et al.

FOREIGN PATENT DOCUMENTS

WO WO 2016/145102 A1 9/2016
WO WO 2016/161372 A1 10/2016
WO WO2016079899 8/2017

OTHER PUBLICATIONS

Wang et al. "Selective tumor cell inhibition effect of Ni—Ti layered double hydroxides thin films driven by the reversed pH gradients of tumor cells." ACS Applied Materials & Interfaces 7.15 (2015): 7843-7854. (Year: 2015).*
Shabalovskaya et al. "Effects of Nitinol surface treatments and ethylene oxide sterilization on Human Lymphocyte Proliferation." Journal of Materials Research (2004). (Year: 2004).*
Japanese Patent Application No. 2019-534814, first Office Action translation, 3 pages.
Ali et al.; "In situ regulation of DC subsets and T cells mediates tumor regression in mice," Sci. Transl. Med., vol. 1, No. 8, 2009, 8ra19, 22 pages.
An et al.; "Design and 3D Printing of Scaffolds and Tissues," Engineering, vol. 1, No. 2, 2015, pp. 261-268.
Baldwin & Kiick; "Polysaccharide modified synthetic polymeric biomaterials," Biopolymers, vol. 94, No. 1, 2010, pp. 128-140.
Boating et al.; "RGD and YIGSR synthetic peptides facilitate cellular adhesion identical to that of laminin and fibronectin but alter the physiology of neonatal cardiac myocytes," Am. J. Physiol. Cell Physio., vol. 288, No. 1, 2005, pp. 30-38.
Boontheekul et al.; "Controlling alginate gel degradation utilizing partial oxidation and bimodal molecular weight distribution," Biomaterials, vol. 26, No. 15, 2005, pp. 2455-2465.
Hanson et al.; "Nanoparticulate STING agonists are potent lymph node-targeted vaccine adjuvants", Technical Advance, The Journal of Clinical Investigation, vol. 125, No. 6, 2015, pp. 2532-2546.
Hansson et al.; "Whole blood coagulation on protein adsorption-resistant PEG and peptide functionalized PEG-coated titanium surfaces," Biomaterials, vol. 26, No. 8, 2005, pp. 861-872.
Hingorani et al.; "Trp53R172H and KrasG12D cooperate to promote chromosomal instability and widely metastatic pancreatic ductal adenocarcinoma in mice," Cancer Cell, vol. 7, No. 5, 2005, pp. 469-483.
Jun et al.; "Development of a YIGSR-peptide-modified polyurethaneurea to enhance endothelialization," J. Biomaterials Sci. Polymer Ed., vol. 15, No. 1, 2004, pp. 73-94.
Kim et al.; "Injectable, spontaneously assembling, inorganic scaffolds modulate immune cells in vivo and increase vaccine efficacy," Nat. Biotechnol., vol. 33, No. 1, 2015, pp. 64-72.
Lee et al.; "Three-Dimensional Collagen/Alginate Hybrid Scaffolds Functionalized with a Drug Delivery System (DDS) for Bone Tissue Regeneration," Chem Mater., vol. 24, No. 5, 2012, pp. 881-891.
Levengood et al.; "Chitosan-based scaffolds for bone tissue engineering," J. Mater. Chem. B, vol. 2, No. 21, 2014, pp. 3161-3184.
Li et al.; "Effects of filtration seeding on cell density, spatial distribution, and proliferation in nonwoven fibrous matrices," Biotechnol. Prog., vol. 17, No. 5, 2001, pp. 935-944.
Lin et al.; "Synthesis, surface and cell-adhesion properties of polyurethanes containing covalently grafted RGD-peptides," J. Biomedical Materials Res., vol. 28, No. 3, 1994, pp. 329-342.
PCT Search Report and Written Opinion mailed May 11, 2018 for PCT Application N. PCT/US2017/067965, 22 pages.
Rigberg et al.; "Thin-film nitinol (NiTi): a feasibility study for a novel aortic stent graft material," J. Vasc. Surg., vol. 50, No. 2, 2009, pp. 375-380.
Singh et al; "3D Printing of Scaffold for Cells Delivery: Advances in Skin Tissue Engineering," Polymers, vol. 8, No. 1, 2016, 17 pages.
Sittinger et al.; "Artificial tissues in perfusion culture," Int. J. Artif. Organs, vol. 2, No. 1, 1997, pp. 57-62.
Stephan et al.; "Biopolymer implants enhance the efficacy of adoptive T-cell therapy," Nat. Biotechnol., vol. 33, No. 1, 2015, pp. 97-101.
Wendt et al.; "Oscillating perfusion of cell suspensions through three-dimensional scaffolds enhances cell seeding efficiency and uniformity," Biotechnol. Bioeng., No. 84, No. 2, 2003, pp. 205-214.
Yang et al.; "Therapeutic potential and challenges of targeting receptor tyrosine kinase ROR1 with monoclonal antibodies in B-cell malignances," Plos One, vol. 6, No. 6, 2011, e21018, 15 pages.
Yang et al.; "Novel cell immobilization method utilizing centrifugal force to achieve high-density hepatocyte culture in porous scaffold," J. Biomed. Mater. Res, vol. 55, No. 3, 2001, pp. 379-386.
Zacco et al.; "A Self-Assembling Peptide Scaffold for the Multivalent Presentation of Antigens," Biomacromolecules, vol. 16, No. 7, 2015, pp. 2188-2197.
Adu-Berchie et al.; "Filmed over with CAR-T cells," Nature Biomedical Engineering, vol. 4, No. 2, 2020, pp. 142-143.
Coon et al.; "Nitinol thin films functionalized with CAR-T cells for the treatment of solid tumours," Nature Biomedical Engineering, vol. 4, No. 2, 2019, pp. 195-206.
Extended European Search Report dated Nov. 10, 2020 for European Application No. 17883391.9, 15 pages.
Gammon et al.; "Improving the clinical impact of biomaterials in cancer immunotherapy," Oncotarget, vol. 7, No. 13, 2016, pp. 15421-15443.
Koshy et al; "Biomaterials for enhancing anti-cancer immunity," Current Opinion in Biotechnology, vol. 40, 2016, pp. 1-8.
Smith et al.; "Biopolymers codelivering engineered T-cells and STING agonists can eliminate heterogeneous tumors," the Journal of Clinical Investigation, vol. 127, No. 6, 2017, pp. 195-206.
Song; "History and current Situation of Shape Memory Alloys Devices for Minimally Invasive Surgery," The Open Medical Devices Journal, vol. 2, No. 2, 2010, pp. 24-31.
Stephan et al.; "Biopolymer implants enhance the efficacy of adoptive T-cell therapy," Nature Biotechnology, vol. 33, No. 1, 2014, pp. 97-101.
Stephan et al.; "Supporting Online Material for Biopolymer implants enhance the efficacy of adoptive T-cell therapy," Nature Biotechnology, vol. 33, No. 1, 2014, pp. 97-101.
Wang et al.; "Selective Tumor Cell Inhibition Effect of Ni—Ti Layered Double Hydroxides Thin films Driven by the Reversed pH Gradients of Tumor Cells," ACS Applied Materials and Interfaces, vol. 7, No. 15, 2015, pp. 7843-7854.
Shabalovskaya et al.; "Critical overview of Nitinol surfaces and their modifications for medical applications," Acta Biomaterialia 4.3, (2008), pp. 447-467.
Michael E. Coon et al. (2020). Nitinol thin films functionalized with CAR-T cells for the treatment of solid tumours. Nature Biomedical Engineering. 4. 1-12. 10.1038/s41551-019-0486-0.

* cited by examiner

Pan-Cytokeratin Mesothelin EpCAM

Average velocity: 2.7 (± 1.1) μm/min 14.1 (± 7.3) μm/min

Average mean displacement: 56 (± 11 ) μm 293 (± 38) μm

TFN Micromesh loaded with CAR-T cells and placed against tissue mimetic for 6 days Ultra-high cells densities still present on film after 6 days.

FIG. 13A
Established tumor lesions in the diaphragm
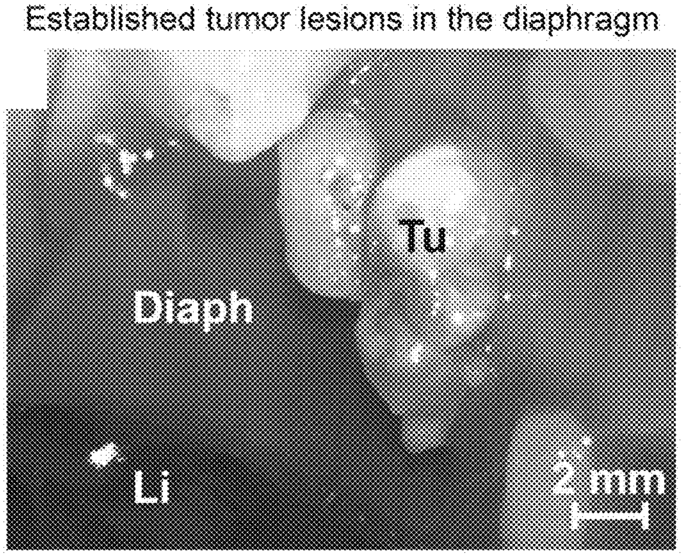
Placement of CAR T-cell seeded thin film
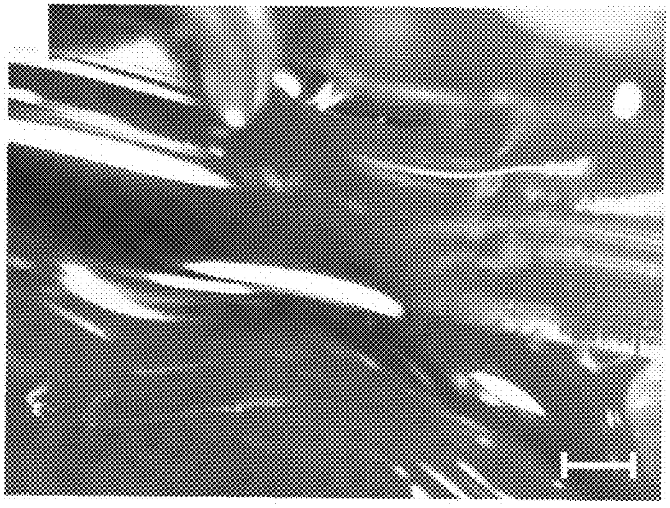
Implanted thin film
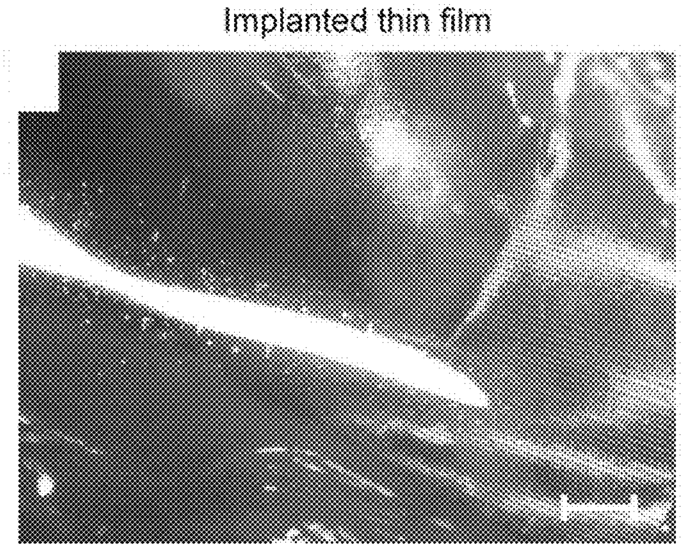

Animals treated with TFN Micromesh achieve 70% survival after 100 days (n = 10 per group, p < 0.0001 vs. control groups)

FIG. 16

GFOGER (SEQ ID NO: 1) Adhesion Motif
GFP*GER (SEQ ID NO: 1)
(P* = 4-hydroxyproline)

FIG. 17

GFOGER (SEQ ID NO: 1) Peptide
GGYGGGPCGPPGPPGPPGPPGPPGFP*GERGPPGPPGPPGPPGPPGPC (SEQ ID NO: 2)
(P* = 4-hydroxyproline)

FIG. 18

ICAM-1 Cell Adhesion Molecule
MAPSSPRPALPALLVLLGALFPGPGNAQTSVSPSKVILPRGGSVLVTCSTSCDQPKL
LGIETPLPKKELLLPGNNRKVYELSNVQEDSQPMCYSNCPDGQSTAKTFLTVYWTP
ERVELAPLPSWQPVGKNLTLRCQVEGGAPRANLTVVLLRGEKELKREPAVGEPAEV
TTTVLVRRDHHGANFSCRTELDLRPQGLELFENTSAPYQLQTFVLPATPPQLVSPRV
LEVDTQGTVVCSLDGLFPVSEAQVHLALGDQRLNPTVTYGNDSFSAKASVSVTAED
EGTQRLTCAVILGNQSQETLQTVTIYSFPAPNVILTKPEVSEGTEVTVKCEAHPRAKV
TLNGVPAQPLGPRAQLLLKATPEDNGRSFSCSATLEVAGQLIHKNQTRELRVLYGPR
LDERDCPGNWTWPENSQQTPMCQAWGNPLPELKCLKDGTFPLPIGESVTVTRDL
EGTYLCRARSTQGEVTREVTVNVLSPRYEIVIITVVAAAVIMGTAGLSTYLYNRQRKIK
KYRLQQAQKGTPMKPNTQATPP (SEQ ID NO: 3)

FIG. 19

FN-III$_{7\text{-}10}$ Fragment
PLSPPTNLHLEANPDTGVLTVSWERSTTPDITGYRITTTPTNGQQGNSLEEVVHADQ
SSCTFDNLSPGLEYNVSVYTVKDDKESVPISDTIIPAVPPPTDLRFTNIGPDTMRVTWA
PPPSIDLTNFLVRYSPVKNEEDVAELSISPSDNAVVLTNLLPGTEYVVSVSSVYEQHES
TPLRGRQKTGLDSPTGIDFSDITANSFTVHWIAPRATITGYRIRHHPEHFSGRPREDR
VPHSRNSITLTNLTPGTEYVVSIVALNGREESPLLIGQQSTVSDVPRDLEVVAATPTSLL
ISWDAPAVTVRYYRITYGETGGNSPVQEFTVPGSKSTATISGLKPGVDYTITVYAVTGR
GDSPASSKPISINYRT (SEQ ID NO: 4)

FIG. 20

IgG4-Fc
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPSCPAPEFLGGPSV
FLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEG
NVFSCSVMHEALHNHYTQKSLSLSLGK (SEQ ID NO: 14)

Hinge-CH2-CH3
ESKYGPPCPPCPAPEFLGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTIS
KAKGQPREPQVYTLPPSQEEMTKNQVSLTCLVKGFYPSDIAVEWESNGQPENNYKTTPP
VL DSDGSFFLYSRLTVDKSRWQEGNVFSCSVMHEALHNHYTQKSLSLSLGK (SEQ ID
NO: 15)

Hinge-CH3
ESKYGPPCPPCPGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYTQKSLSLSLGK
(SEQ ID NO: 16)

Hinge only
ESKYGPPCPPCP (SEQ ID NO: 17)

CD28 Transmembrane domain
MFWVLVVVGGVLACYSLLVTVAFIIFWV (SEQ ID NO: 18)

CD28 Cytoplasmic domain (LL to GG)
RSKRSRGGHSDYMNMTPRRPGPTRKHYQPYAPPRDFAAYRS (SEQ ID NO: 19)

4-1BB Cytoplasmic domain
KRGRKKLLYIFKQPFMRPVQTTQEEDGCSCRFPEEEEGGCEL (SEQ ID NO: 20)

CD3-ζ Cytoplasmic domain
RVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR
(SEQ ID NO: 21)

FIG. 20 (cont'd)

T2A
LEGGGEGRGSLLTCGDVEENPGPR (SEQ ID NO: 22)

tEGFR
LEGGGEGRGSLLTCGDVEENPGPR (SEQ ID NO: 23)

Strep tag II
WSHPQFEK (SEQ ID NO: 24)

Myc tag
EQKLISEEDL (SEQ ID NO: 25)

V5 tag
GKPIPNPLLGLDST (SEQ ID NO: 26)

FLAG tag
DYKDDDDK (SEQ ID NO: 27)

SEQUENCE LISTING

<160> NUMBER OF SEQ ID NOS: 27

<210> SEQ ID NO 1
<211> LENGTH: 6
<212> TYPE: PRT
<213> ORGANISM: Artificial sequence
<220> FEATURE:
<223> OTHER INFORMATION: GFOGER adhesion motif
<220> FEATURE:
<221> NAME/KEY: 4Hyp
<222> LOCATION: (3)..(3)

<400> SEQUENCE: 1

Gly Phe Pro Gly Glu Arg
1               5

<210> SEQ ID NO 2
<211> LENGTH: 47
<212> TYPE: PRT
<213> ORGANISM: Artificial
<220> FEATURE:
<223> OTHER INFORMATION: GFOGER peptide
<220> FEATURE:
<221> NAME/KEY: 4Hyp
<222> LOCATION: (26)..(26)

<400> SEQUENCE: 2

Gly Gly Tyr Gly Gly Gly Pro Cys Gly Pro Pro Gly Pro Pro Gly Pro
1               5                   10                  15

Pro Gly Pro Pro Gly Pro Pro Gly Phe Pro Gly Glu Arg Gly Pro Pro
            20                  25                  30

Gly Pro Pro Gly Pro Pro Gly Pro Pro Gly Pro Pro Gly Pro Cys
        35                  40                  45

<210> SEQ ID NO 3
<211> LENGTH: 532
<212> TYPE: PRT
<213> ORGANISM: Homo sapiens

<400> SEQUENCE: 3

-continued

```
Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415
```

-continued

```
Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
    450                 455                 460

Glu Val Thr Arg Glu Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
    530


<210> SEQ ID NO 4
<211> LENGTH: 368
<212> TYPE: PRT
<213> ORGANISM: Homo sapiens

<400> SEQUENCE: 4

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
    50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro Ala Val Pro
                85                  90                  95

Pro Pro Thr Asp Leu Arg Phe Thr Asn Ile Gly Pro Asp Thr Met Arg
            100                 105                 110

Val Thr Trp Ala Pro Pro Pro Ser Ile Asp Leu Thr Asn Phe Leu Val
        115                 120                 125

Arg Tyr Ser Pro Val Lys Asn Glu Glu Asp Val Ala Glu Leu Ser Ile
    130                 135                 140

Ser Pro Ser Asp Asn Ala Val Val Leu Thr Asn Leu Leu Pro Gly Thr
145                 150                 155                 160

Glu Tyr Val Val Ser Val Ser Ser Val Tyr Glu Gln His Glu Ser Thr
                165                 170                 175

Pro Leu Arg Gly Arg Gln Lys Thr Gly Leu Asp Ser Pro Thr Gly Ile
            180                 185                 190

Asp Phe Ser Asp Ile Thr Ala Asn Ser Phe Thr Val His Trp Ile Ala
        195                 200                 205

Pro Arg Ala Thr Ile Thr Gly Tyr Arg Ile Arg His His Pro Glu His
    210                 215                 220

Phe Ser Gly Arg Pro Arg Glu Asp Arg Val Pro His Ser Arg Asn Ser
225                 230                 235                 240

Ile Thr Leu Thr Asn Leu Thr Pro Gly Thr Glu Tyr Val Val Ser Ile
                245                 250                 255
```

-continued

Val Ala Leu Asn Gly Arg Glu Glu Ser Pro Leu Leu Ile Gly Gln Gln
260 265 270

Ser Thr Val Ser Asp Val Pro Arg Asp Leu Glu Val Val Ala Ala Thr
275 280 285

Pro Thr Ser Leu Leu Ile Ser Trp Asp Ala Pro Ala Val Thr Val Arg
290 295 300

Tyr Tyr Arg Ile Thr Tyr Gly Glu Thr Gly Gly Asn Ser Pro Val Gln
305 310 315 320

Glu Phe Thr Val Pro Gly Ser Lys Ser Thr Ala Thr Ile Ser Gly Leu
325 330 335

Lys Pro Gly Val Asp Tyr Thr Ile Thr Val Tyr Ala Val Thr Gly Arg
340 345 350

Gly Asp Ser Pro Ala Ser Ser Lys Pro Ile Ser Ile Asn Tyr Arg Thr
355 360 365

<210> SEQ ID NO 5
<211> LENGTH: 5
<212> TYPE: PRT
<213> ORGANISM: Artificial Sequence
<220> FEATURE:
<223> OTHER INFORMATION: Sequence in a polymer backbone

<400> SEQUENCE: 5

Tyr Ile Gly Ser Arg
1 5

<210> SEQ ID NO 6
<211> LENGTH: 750
<212> TYPE: PRT
<213> ORGANISM: Homo sapiens

<400> SEQUENCE: 6

Met Trp Asn Leu Leu His Glu Thr Asp Ser Ala Val Ala Thr Ala Arg
1 5 10 15

Arg Pro Arg Trp Leu Cys Ala Gly Ala Leu Val Leu Ala Gly Gly Phe
20 25 30

Phe Leu Leu Gly Phe Leu Phe Gly Trp Phe Ile Lys Ser Ser Asn Glu
35 40 45

Ala Thr Asn Ile Thr Pro Lys His Asn Met Lys Ala Phe Leu Asp Glu
50 55 60

Leu Lys Ala Glu Asn Ile Lys Lys Phe Leu Tyr Asn Phe Thr Gln Ile
65 70 75 80

Pro His Leu Ala Gly Thr Glu Gln Asn Phe Gln Leu Ala Lys Gln Ile
85 90 95

Gln Ser Gln Trp Lys Glu Phe Gly Leu Asp Ser Val Glu Leu Ala His
100 105 110

Tyr Asp Val Leu Leu Ser Tyr Pro Asn Lys Thr His Pro Asn Tyr Ile
115 120 125

Ser Ile Ile Asn Glu Asp Gly Asn Glu Ile Phe Asn Thr Ser Leu Phe
130 135 140

Glu Pro Pro Pro Pro Gly Tyr Glu Asn Val Ser Asp Ile Val Pro Pro
145 150 155 160

Phe Ser Ala Phe Ser Pro Gln Gly Met Pro Glu Gly Asp Leu Val Tyr
165 170 175

Val Asn Tyr Ala Arg Thr Glu Asp Phe Phe Lys Leu Glu Arg Asp Met
180 185 190

-continued

```
Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
```

```
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750


<210> SEQ ID NO 7
<211> LENGTH: 123
<212> TYPE: PRT
<213> ORGANISM: Homo sapiens

<400> SEQUENCE: 7

Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ala Ile Leu Ala Leu Leu Pro Ala
            100                 105                 110

Leu Gly Leu Leu Leu Trp Gly Pro Gly Gln Leu
        115                 120


<210> SEQ ID NO 8
<211> LENGTH: 622
<212> TYPE: PRT
<213> ORGANISM: Homo sapiens

<400> SEQUENCE: 8

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
```

-continued

```
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr His Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495
```

```
Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620


<210> SEQ ID NO 9
<211> LENGTH: 556
<212> TYPE: PRT
<213> ORGANISM: Homo sapiens

<400> SEQUENCE: 9

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ser
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
```

-continued

```
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555
```

<210> SEQ ID NO 10
<211> LENGTH: 297
<212> TYPE: PRT
<213> ORGANISM: Homo sapiens

<400> SEQUENCE: 10

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60
```

-continued

Ala Leu Gly Gly Leu Leu Met Ile Pro Ala Gly Ile Tyr Ala Pro Ile
65 70 75 80

Cys Val Thr Val Trp Tyr Pro Leu Trp Gly Gly Ile Met Tyr Ile Ile
85 90 95

Ser Gly Ser Leu Leu Ala Ala Thr Glu Lys Asn Ser Arg Lys Cys Leu
100 105 110

Val Lys Gly Lys Met Ile Met Asn Ser Leu Ser Leu Phe Ala Ala Ile
115 120 125

Ser Gly Met Ile Leu Ser Ile Met Asp Ile Leu Asn Ile Lys Ile Ser
130 135 140

His Phe Leu Lys Met Glu Ser Leu Asn Phe Ile Arg Ala His Thr Pro
145 150 155 160

Tyr Ile Asn Ile Tyr Asn Cys Glu Pro Ala Asn Pro Ser Glu Lys Asn
165 170 175

Ser Pro Ser Thr Gln Tyr Cys Tyr Ser Ile Gln Ser Leu Phe Leu Gly
180 185 190

Ile Leu Ser Val Met Leu Ile Phe Ala Phe Phe Gln Glu Leu Val Ile
195 200 205

Ala Gly Ile Val Glu Asn Glu Trp Lys Arg Thr Cys Ser Arg Pro Lys
210 215 220

Ser Asn Ile Val Leu Leu Ser Ala Glu Glu Lys Lys Glu Gln Thr Ile
225 230 235 240

Glu Ile Lys Glu Glu Val Val Gly Leu Thr Glu Thr Ser Ser Gln Pro
245 250 255

Lys Asn Glu Glu Asp Ile Glu Ile Ile Pro Ile Gln Glu Glu Glu Glu
260 265 270

Glu Glu Thr Glu Thr Asn Phe Pro Glu Pro Pro Gln Asp Gln Glu Ser
275 280 285

Ser Pro Ile Glu Asn Asp Ser Ser Pro
290 295

<210> SEQ ID NO 11
<211> LENGTH: 937
<212> TYPE: PRT
<213> ORGANISM: Homo sapiens

<400> SEQUENCE: 11

Met His Arg Pro Arg Arg Arg Gly Thr Arg Pro Pro Leu Leu Ala Leu
1 5 10 15

Leu Ala Ala Leu Leu Leu Ala Ala Arg Gly Ala Ala Ala Gln Glu Thr
20 25 30

Glu Leu Ser Val Ser Ala Glu Leu Val Pro Thr Ser Ser Trp Asn Ile
35 40 45

Ser Ser Glu Leu Asn Lys Asp Ser Tyr Leu Thr Leu Asp Glu Pro Met
50 55 60

Asn Asn Ile Thr Thr Ser Leu Gly Gln Thr Ala Glu Leu His Cys Lys
65 70 75 80

Val Ser Gly Asn Pro Pro Pro Thr Ile Arg Trp Phe Lys Asn Asp Ala
85 90 95

Pro Val Val Gln Glu Pro Arg Arg Leu Ser Phe Arg Ser Thr Ile Tyr
100 105 110

Gly Ser Arg Leu Arg Ile Arg Asn Leu Asp Thr Thr Asp Thr Gly Tyr
115 120 125

Phe Gln Cys Val Ala Thr Asn Gly Lys Glu Val Val Ser Ser Thr Gly
130 135 140

-continued

Val Leu Phe Val Lys Phe Gly Pro Pro Pro Thr Ala Ser Pro Gly Tyr
145 150 155 160

Ser Asp Glu Tyr Glu Glu Asp Gly Phe Cys Gln Pro Tyr Arg Gly Ile
165 170 175

Ala Cys Ala Arg Phe Ile Gly Asn Arg Thr Val Tyr Met Glu Ser Leu
180 185 190

His Met Gln Gly Glu Ile Glu Asn Gln Ile Thr Ala Ala Phe Thr Met
195 200 205

Ile Gly Thr Ser Ser His Leu Ser Asp Lys Cys Ser Gln Phe Ala Ile
210 215 220

Pro Ser Leu Cys His Tyr Ala Phe Pro Tyr Cys Asp Glu Thr Ser Ser
225 230 235 240

Val Pro Lys Pro Arg Asp Leu Cys Arg Asp Glu Cys Glu Ile Leu Glu
245 250 255

Asn Val Leu Cys Gln Thr Glu Tyr Ile Phe Ala Arg Ser Asn Pro Met
260 265 270

Ile Leu Met Arg Leu Lys Leu Pro Asn Cys Glu Asp Leu Pro Gln Pro
275 280 285

Glu Ser Pro Glu Ala Ala Asn Cys Ile Arg Ile Gly Ile Pro Met Ala
290 295 300

Asp Pro Ile Asn Lys Asn His Lys Cys Tyr Asn Ser Thr Gly Val Asp
305 310 315 320

Tyr Arg Gly Thr Val Ser Val Thr Lys Ser Gly Arg Gln Cys Gln Pro
325 330 335

Trp Asn Ser Gln Tyr Pro His Thr His Thr Phe Thr Ala Leu Arg Phe
340 345 350

Pro Glu Leu Asn Gly Gly His Ser Tyr Cys Arg Asn Pro Gly Asn Gln
355 360 365

Lys Glu Ala Pro Trp Cys Phe Thr Leu Asp Glu Asn Phe Lys Ser Asp
370 375 380

Leu Cys Asp Ile Pro Ala Cys Asp Ser Lys Asp Ser Lys Glu Lys Asn
385 390 395 400

Lys Met Glu Ile Leu Tyr Ile Leu Val Pro Ser Val Ala Ile Pro Leu
405 410 415

Ala Ile Ala Leu Leu Phe Phe Phe Ile Cys Val Cys Arg Asn Asn Gln
420 425 430

Lys Ser Ser Ser Ala Pro Val Gln Arg Gln Pro Lys His Val Arg Gly
435 440 445

Gln Asn Val Glu Met Ser Met Leu Asn Ala Tyr Lys Pro Lys Ser Lys
450 455 460

Ala Lys Glu Leu Pro Leu Ser Ala Val Arg Phe Met Glu Glu Leu Gly
465 470 475 480

Glu Cys Ala Phe Gly Lys Ile Tyr Lys Gly His Leu Tyr Leu Pro Gly
485 490 495

Met Asp His Ala Gln Leu Val Ala Ile Lys Thr Leu Lys Asp Tyr Asn
500 505 510

Asn Pro Gln Gln Trp Thr Glu Phe Gln Gln Glu Ala Ser Leu Met Ala
515 520 525

Glu Leu His His Pro Asn Ile Val Cys Leu Leu Gly Ala Val Thr Gln
530 535 540

Glu Gln Pro Val Cys Met Leu Phe Glu Tyr Ile Asn Gln Gly Asp Leu
545 550 555 560

-continued

His Glu Phe Leu Ile Met Arg Ser Pro His Ser Asp Val Gly Cys Ser
565 570 575

Ser Asp Glu Asp Gly Thr Val Lys Ser Ser Leu Asp His Gly Asp Phe
580 585 590

Leu His Ile Ala Ile Gln Ile Ala Ala Gly Met Glu Tyr Leu Ser Ser
595 600 605

His Phe Phe Val His Lys Asp Leu Ala Ala Arg Asn Ile Leu Ile Gly
610 615 620

Glu Gln Leu His Val Lys Ile Ser Asp Leu Gly Leu Ser Arg Glu Ile
625 630 635 640

Tyr Ser Ala Asp Tyr Tyr Arg Val Gln Ser Lys Ser Leu Leu Pro Ile
645 650 655

Arg Trp Met Pro Pro Glu Ala Ile Met Tyr Gly Lys Phe Ser Ser Asp
660 665 670

Ser Asp Ile Trp Ser Phe Gly Val Val Leu Trp Glu Ile Phe Ser Phe
675 680 685

Gly Leu Gln Pro Tyr Tyr Gly Phe Ser Asn Gln Glu Val Ile Glu Met
690 695 700

Val Arg Lys Arg Gln Leu Leu Pro Cys Ser Glu Asp Cys Pro Pro Arg
705 710 715 720

Met Tyr Ser Leu Met Thr Glu Cys Trp Asn Glu Ile Pro Ser Arg Arg
725 730 735

Pro Arg Phe Lys Asp Ile His Val Arg Leu Arg Ser Trp Glu Gly Leu
740 745 750

Ser Ser His Thr Ser Ser Thr Thr Pro Ser Gly Gly Asn Ala Thr Thr
755 760 765

Gln Thr Thr Ser Leu Ser Ala Ser Pro Val Ser Asn Leu Ser Asn Pro
770 775 780

Arg Tyr Pro Asn Tyr Met Phe Pro Ser Gln Gly Ile Thr Pro Gln Gly
785 790 795 800

Gln Ile Ala Gly Phe Ile Gly Pro Pro Ile Pro Gln Asn Gln Arg Phe
805 810 815

Ile Pro Ile Asn Gly Tyr Pro Ile Pro Pro Gly Tyr Ala Ala Phe Pro
820 825 830

Ala Ala His Tyr Gln Pro Thr Gly Pro Pro Arg Val Ile Gln His Cys
835 840 845

Pro Pro Pro Lys Ser Arg Ser Pro Ser Ser Ala Ser Gly Ser Thr Ser
850 855 860

Thr Gly His Val Thr Ser Leu Pro Ser Ser Gly Ser Asn Gln Glu Ala
865 870 875 880

Asn Ile Pro Leu Leu Pro His Met Ser Ile Pro Asn His Pro Gly Gly
885 890 895

Met Gly Ile Thr Val Phe Gly Asn Lys Ser Gln Lys Pro Tyr Lys Ile
900 905 910

Asp Ser Lys Gln Ala Ser Leu Leu Gly Asp Ala Asn Ile His Gly His
915 920 925

Thr Glu Ser Met Ile Ser Ala Glu Leu
930 935

<210> SEQ ID NO 12
<211> LENGTH: 168
<212> TYPE: PRT
<213> ORGANISM: Homo sapiens

<400> SEQUENCE: 12

```
Met Gly His His His His His His His His His His Ser Ser Gly His
1               5                   10                  15

Ile Glu Gly Arg His Met Arg Arg Val Pro Gly Val Ala Pro Thr Leu
            20                  25                  30

Val Arg Ser Ala Ser Glu Thr Ser Glu Lys Arg Pro Phe Met Cys Ala
        35                  40                  45

Tyr Pro Gly Cys Asn Lys Arg Tyr Phe Lys Leu Ser His Leu Gln Met
    50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
            100                 105                 110

Lys Phe Ser Arg Ser Asp His Leu Lys Thr His Thr Arg Thr His Thr
        115                 120                 125

Gly Glu Lys Pro Phe Ser Cys Arg Trp Pro Ser Cys Gln Lys Lys Phe
    130                 135                 140

Ala Arg Ser Asp Glu Leu Val Arg His His Asn Met His Gln Arg Asn
145                 150                 155                 160

Met Thr Lys Leu Gln Leu Ala Leu
                165


<210> SEQ ID NO 13
<211> LENGTH: 15
<212> TYPE: PRT
<213> ORGANISM: Artificial Sequence
<220> FEATURE:
<223> OTHER INFORMATION: linker

<400> SEQUENCE: 13

Gly Gly Gly Gly Ser Gly Gly Gly Gly Ser Gly Gly Gly Gly Ser
1               5                   10                  15


<210> SEQ ID NO 14
<211> LENGTH: 327
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125
```

-continued

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 15
<211> LENGTH: 229
<212> TYPE: PRT
<213> ORGANISM: Artificial Sequence
<220> FEATURE:
<223> OTHER INFORMATION: Hinge-CH2-CH3

<400> SEQUENCE: 15

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160
```

-continued

```
Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 16
<211> LENGTH: 119
<212> TYPE: PRT
<213> ORGANISM: Artificial Sequence
<220> FEATURE:
<223> OTHER INFORMATION: Hinge-CH3

<400> SEQUENCE: 16

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115


<210> SEQ ID NO 17
<211> LENGTH: 12
<212> TYPE: PRT
<213> ORGANISM: Artificial Sequence
<220> FEATURE:
<223> OTHER INFORMATION: Hinge

<400> SEQUENCE: 17

Glu Ser Lys Tyr Gly Pro Pro Cys Pro Pro Cys Pro
1               5                   10


<210> SEQ ID NO 18
<211> LENGTH: 28
<212> TYPE: PRT
<213> ORGANISM: Homo sapiens

<400> SEQUENCE: 18

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25


<210> SEQ ID NO 19
<211> LENGTH: 41
```

<212> TYPE: PRT
<213> ORGANISM: Homo sapiens

<400> SEQUENCE: 19

```
Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 20
<211> LENGTH: 42
<212> TYPE: PRT
<213> ORGANISM: Homo sapiens

<400> SEQUENCE: 20

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 21
<211> LENGTH: 112
<212> TYPE: PRT
<213> ORGANISM: Homo sapiens

<400> SEQUENCE: 21

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 22
<211> LENGTH: 24
<212> TYPE: PRT
<213> ORGANISM: Homo sapiens

<400> SEQUENCE: 22

```
Leu Glu Gly Gly Gly Glu Gly Arg Gly Ser Leu Leu Thr Cys Gly Asp
1               5                   10                  15

Val Glu Glu Asn Pro Gly Pro Arg
            20
```

<210> SEQ ID NO 23
<211> LENGTH: 357
<212> TYPE: PRT
<213> ORGANISM: homo sapiens

<400> SEQUENCE: 23

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 24
<211> LENGTH: 8
<212> TYPE: PRT
<213> ORGANISM: Artificial Sequence
<220> FEATURE:
<223> OTHER INFORMATION: Strep Tag II -continued

```
<400> SEQUENCE: 24

Trp Ser His Pro Gln Phe Glu Lys
1               5


<210> SEQ ID NO 25
<211> LENGTH: 10
<212> TYPE: PRT
<213> ORGANISM: Artificial Sequence
<220> FEATURE:
<223> OTHER INFORMATION: Myc tag

<400> SEQUENCE: 25

Glu Gln Lys Leu Ile Ser Glu Glu Asp Leu
1               5                   10


<210> SEQ ID NO 26
<211> LENGTH: 14
<212> TYPE: PRT
<213> ORGANISM: Artificial Sequence
<220> FEATURE:
<223> OTHER INFORMATION: V5 tag

<400> SEQUENCE: 26

Gly Lys Pro Ile Pro Asn Pro Leu Leu Gly Leu Asp Ser Thr
1               5                   10


<210> SEQ ID NO 27
<211> LENGTH: 8
<212> TYPE: PRT
<213> ORGANISM: Artificial Sequence
<220> FEATURE:
<223> OTHER INFORMATION: FLAG tag

<400> SEQUENCE: 27

Asp Tyr Lys Asp Asp Asp Asp Lys
1               5
```

SCAFFOLDS TO TREAT SOLID TUMOR CELLS AND ESCAPE VARIANTS

CROSS REFERENCE TO RELATED APPLICATION

This application is a continuation of U.S. patent application Ser. No. 16/472,764, filed Jun. 21, 2019, which is a U.S. national stage entry of PCT/US2017/067965, filed Dec. 21, 2017, which claims priority to U.S. Provisional Patent Application No. 62/437,572, filed on Dec. 21, 2016, the entire contents of each which is incorporated by reference herein.

STATEMENT REGARDING FEDERALLY SPONSORED RESEARCH OR DEVELOPMENT

This invention was made with government support under CA181413 awarded by the National Institutes of Health. The government has certain rights in the invention.

REFERENCE TO SEQUENCE LISTING

A computer readable text file currently filed herewith, created on or about Jun. 21, 2022, with a file size of 50 KB, contains the sequence listing for this application and is hereby incorporated by reference in its entirety.

FIELD OF THE DISCLOSURE

The present disclosure provides implantable scaffolds that treat solid tumors and escape variants and provide effective vaccinations against cancer recurrence. The scaffolds include genetically-reprogrammed lymphocytes and a lymphocyte-activating moiety.

BACKGROUND OF THE DISCLOSURE

Cancer immunotherapy describes a field in which a patient's immune system is used to treat cancer. For example, cancer immunotherapy includes the use of vaccines to immunize patients against the development of cancer. Unfortunately, the responses cancer vaccines can elicit can require months to mature and are usually insufficient to control advanced disease.

Attempts have also been made to more quickly or potently stimulate a patient's own T cells to attack cancer cells. The repertoire of receptors normally expressed by T cells generally has a low affinity to self/tumor antigens, however, so this approach has not achieved sufficient success in the fight against cancer.

An emerging immunotherapy approach involves the alteration of patient-derived lymphocytes (e.g., T cells) with genes encoding chimeric antigen receptors (CARs) that are engineered to have high affinity for selected macromolecular targets in the tumors. The introduced genes can also produce costimulatory signals to elicit robust T cell expansion. The method involves retrieval of T cells from a patient and redirecting them ex vivo to express CARs composed of a tumor-specific single-chain antibody (scFv) fused to costimulatory and CD3ζ signaling domains, which enable the programmed cells to lyse tumor targets in a human leukocyte antigen (HLA)-independent fashion.

Therapies that employ such CAR-programmed T cells have consistently produced positive results in patients with hematologic malignancies (i.e., liquid blood cancers) in clinical trials. However, when it comes to solid tumors, the effectiveness of these therapies has been limited by: 1) inefficient homing of the lymphocytes to the tumor site; 2) the immunosuppressive microenvironment solid tumors create; and 3) the phenotypic diversity of solid tumors which means that cancer cells not recognized by the CAR-programmed T cells' targeting receptors can form escape variants that elude the programmed T cells. Thus, while the genetic re-programming of T cells remains a promising therapy, significant improvements are required in their use to treat solid tumors.

US 2016/0008399 describes an implantable scaffold that greatly improves the ability of genetically-reprogrammed lymphocytes (e.g., T cells) to treat solid tumors. The implantable scaffolds include genetically-reprogrammed lymphocytes, at least one lymphocyte-adhesion moiety associated with the scaffold; at least one lymphocyte-activating moiety associated with the scaffold, and optionally an immune stimulant. Because the scaffold can be implanted at the site of a solid tumor, issues regarding the inefficient homing of the lymphocytes to the tumor site is overcome.

US 2016/0008399 also describes how the implantable scaffolds create extended second wave protection against tumor cells. Particularly, lymphocytes seeded within the scaffold exit the scaffold following implantation and disperse at high densities throughout, for example, a tumor resection bed and into draining lymph nodes to destroy remaining residual tumor cells following a resection. This step releases large amounts of tumor antigens from dying tumor cells into the tissue. The tumor antigens are subsequently taken up by antigen presenting cells (APCs). By releasing an immune stimulant, the scaffolds can activate APCs and tumor-reactive immune cells to mount a robust host anti-tumor immune response. This "second wave" of anti-tumor immunity is broader and involves multiple cell types acting in synergy to eliminate remaining tumor cells.

STING (STimulator of INterferon Genes) pathway agonists are a type of potent immune stimulant that have been the focus of intense study in cancer immunotherapy. However, like previously described adjuvant compounds (e.g., R848 and related imidazoquinoline TLR7/8 agonists, muramyl dipeptides that trigger (NOD)-like receptors, and RNA oligonucleotide ligands of RIG-I), treatments with unformulated STING agonists are accompanied by systemic inflammatory toxicity, which represents a major hurdle for using these compounds to treat cancer patients. Thus, to be clinically effective, high dosages of STING agonists are required to be repeatedly injected directly into tumor lesions, which limits this therapy to sites that are accessible for daily inoculations (e.g., skin malignancies).

SUMMARY OF THE DISCLOSURE

The current disclosure continues to advance cancer immunotherapy by providing improved implantable scaffold. The implantable scaffolds disclosed herein are seeded with (i) genetically-reprogrammed lymphocytes; and (ii) at least one lymphocyte-activating moiety. Thus, in particular embodiments, these implantable scaffolds can be simpler in form than those described in US 2016/0008399. In particular embodiments, the implantable scaffolds disclosed herein can also include a STING agonist. These embodiments provide a mechanism to harness the potent immunostimulatory effects of STING agonists, without systemic inflammatory toxicity and without the need for daily injections.

The robustness of the anti-cancer effects observed with the disclosed implantable scaffolds were synergistic, unexpected, and remarkable. In almost half of all subjects tested, complete eradication of solid tumors was achieved. Thus, tumor cells recognized by the genetically-reprogrammed lymphocytes as well as tumor cells that normally would have become escape variants were effectively treated. In addition, following complete eradication of solid tumors, subjects were re-challenged with cancer cells. One hundred percent of re-challenged subjects failed to develop any measurable tumors demonstrating the effectiveness of the self-vaccine site. Thus, the implantable scaffolds disclosed herein provide a significant advance in the ongoing fight against solid tumor cancers.

In particular embodiments, the scaffolds include a scaffold matrix material selected from a micropatterned metallic thin film or a polymer. In particular embodiments, the genetically-reprogrammed lymphocytes are T cells or natural killer (NK) cells. In particular embodiments, the at least one lymphocyte-activating moiety is selected from interleukin 15 and/or antibodies specific for CD3, CD28, and/or CD137. In particular embodiments, the scaffolds include a STING agonist. In particular embodiments, the STING agonist is c-diGMP. In particular embodiments, the STING agonist is embedded within a drug eluting polymer. In particular embodiments, the scaffolds include a lymphocyte-adhesion moiety. In particular embodiments, the lymphocyte-adhesion moiety is selected from fibrin or a GFOGER (SEQ ID NO: 1) peptide.

In particular embodiments, the scaffolds include: (i) genetically-reprogrammed lymphocytes disposed within a Thin Film Nitinol (TFN) micromesh. The genetically-reprogrammed lymphocytes can include T cells with lymphocyte-activating moieties including antibodies specific for CD3, CD28, and/or CD137 and/or can include NK cells with lymphocyte-activating moieties including interleukin-15 and antibodies specific for CD137. In particular embodiments, these embodiments can include the lymphocyte-adhesion moiety fibrin. In particular embodiments, these embodiments can include c-diGMP. In particular embodiments, these embodiments can include c-diGMP embedded within a drug eluting polymer coated onto the surface of the TFN micromesh. In particular embodiments, these embodiments can include a STING agonist (e.g., c-diGMP) embedded within particles. If particles are used, one or more lymphocyte activating moieties may be on the surface of the particles.

In particular embodiments, a scaffold including a TFN micromesh can include a high-density of cells (at least $7\times10^6$ per $cm^2$ or at least $8\times10^6$ cells per $cm^2$). TFN micromesh can allow for high cell densities, for example, by packing three layers of cells into each layer of TFN micromesh.

In particular embodiments, a scaffold including a TFN micromesh can be used as a long-acting scaffold that may continue to deliver lymphocytes for several days, for more than one week, and/or for more than two weeks.

In particular embodiments, the scaffolds include (i) genetically-reprogrammed lymphocytes disposed within an alginate scaffold matrix. The genetically-reprogrammed lymphocytes can include T cells with lymphocyte-activating moieties including antibodies specific for CD3, CD28, and/or CD137 and/or can include NK cells with lymphocyte-activating moieties including interleukin-15 and antibodies specific for CD137. In particular embodiments, these embodiments can include a GFOGER (SEQ ID NO: 1) peptide lymphocyte-adhesion moiety. In particular embodiments, these embodiments can include c-diGMP. In particular embodiments, these embodiments can include c-diGMP embedded within a drug eluting polymer coated onto the surface of the alginate scaffold. In particular embodiments, these embodiments can include a STING agonist (e.g., c-diGMP) embedded within particles. If particles are used, one or more lymphocyte activating moieties may be on the surface of the particles.

BRIEF DESCRIPTION OF THE FIGURES

The patent or application file contains at least one drawing executed in color. Copies of this patent or patent application publication with color drawing(s) will be provided by the Office upon request and payment of the necessary fee.

(FIG. 2A) Orthotopic mouse model of pancreatic ductal adenocarcinoma. (FIG. 2B) Bright field microscopy of KPC pancreas 7 days after surgical implantation. Hematoxylin/eosin staining reveals invasive adenocarcinoma interspersed with parenchymal tissue in the head of the pancreas; the adjacent healthy tissue accentuates the disorganized nature of the neoplastic regions. The formation of both differentiated and undifferentiated acinar structures (i.e., glands and ducts), which are hallmarks of adenocarcinoma, is also clear in these samples. Analysis of magnified (20×) images revealed substantial recruitment of immune cells, including polymorphonuclear leukocytes, within the tumor microenvironment. The dashed rectangle localizes the magnified insert. Scale bar, 100 μm. (FIG. 2C) Heat map representation of flow cytometry data that quantifies the cell-to-cell variability in Rae-1 expression by KPC tumors. Seven-day-old tumors (tagged with GFP to distinguish them) were disaggregated into single-cell suspensions and labeled with antibodies against Rae-1 so mean fluorescent intensities of this antigen could be measured by flow cytometry; the shading indicates relative expression levels compared to an isotype control. Results from 1,800 randomly-chosen cells are shown. (FIG. 2D) This schematic depicts how the chimeric receptor used to recognize Rae-1 includes full-length mouse NGK2D fused to a murine CD3ζ intracellular signaling molecule. (FIG. 2E) Flow cytometry measuring surface expression of the NKG2D CAR on mouse effector T cells after retroviral transduction and three days of expansion in medium containing G418. (FIG. 2F) $^{51}$Cr release cytotoxicity assay of NKG2D CAR-transduced T cells reacting with KPC pancreatic tumor cells. (FIG. 2G) Ten days after firefly luciferase-expressing KPC tumor cells were transplanted into the pancreas of albino C57BL/6 mice, the animals were injected with $10^7$ NKG2D CAR-transduced T cells. To measure the dynamics of programmed lymphocyte targeting, in parallel experiments mice were injected with CAR-T cells that co-express the click beetle red luciferase reporter. Shown is sequential bioluminescence imaging of the KPC tumors and the adoptively transferred T cells in five representative mice from each cohort (n=10). (FIG. 2H) Kaplan- Meier survival curves for treated and control mice. Shown are ten mice per treatment group pooled from three independent experiments; ms, median survival. Statistical analysis between the treated experimental and the untreated control group, depicted here, was done using the Log-rank test and $P<0.05$ was considered significant. (FIG. 2I) Flow cytometry quantification of Rae-1 antigen expression on KPC tumor cells following NKG2D CAR-T cell therapy. Shown are 1,800 randomly-chosen cells.

(FIG. 3A) Brightfield microscopy of stimulatory microspheres incorporated into the scaffold; below is a depiction of microparticle composition. Scale bar, 70 μm. (FIG. 3B) This series illustrates a disclosed methodology: [1] Scaffold; [2] Seeding of tumor-reactive T cells into the device; [3] Incision; [4] Orthotopic KPC pancreatic tumor; [5]-[7] Implantation of a T cell-loaded device; [8] Wound closure; [9] Sustained release of tumor-reactive T cells.

(FIG. 4A) Bioluminescence imaging of KPC tumors and adoptively transferred CAR-T cells. Mice were treated with $10^7$ NKG2D-transduced lymphocytes injected locally into the tumor, or contained in bioactive scaffolds implanted directly onto the tumor surface. Five representative mice from each cohort (n=10) are shown. (FIG. 4B) T cell signal intensities from sequential bioluminescence images captured every two days after cell transfer. Each line represents one animal and each dot indicates the whole animal photon count. At the indicated time points, pairwise differences in photon counts between treatment groups were analyzed with the Wilcoxon rank-sum test. (FIG. 4C) Quantified KPC bioluminescent tumor signal. (FIG. 4D) Kaplan-Meier survival curves for treated and control mice. Shown are ten mice per treatment group pooled from three independent experiments. ms, median survival. Statistical analysis between the treated experimental and the untreated control group, depicted here, was done using the Log-rank test and $P<0.05$ was considered significant. (FIG. 4E) Flow cytometry quantification of Rae-1 antigen expression on KPC tumor cells following NKG2D CAR-T cell therapy. Shown are 1,800 randomly-chosen cells.

(FIG. 5A) Schematic diagrams of a scaffold loaded with CAR-T cells interacting with the tumor bed: Panels 1 and 2 show how factor-containing microspheres incorporated into the device stimulate the expansion of CAR-expressing T cells and promote their egress into surrounding tissue. APC, antigen presenting cell. Panels 2 and 3 illustrate the release of vaccine adjuvant from T cell-loaded scaffolds, priming host immune cells to recognize and lyse tumor cells and thereby protect against antigen escape variants. (FIG. 5B) Macro- and microscopic views of a porous alginate matrix functionalized with microparticles with the STING agonist cyclic-di-GMP (i.e., c-diGMP or cdGMP, which are used interchangeably) entrapped in the polymer core and stimulatory anti-CD3/CD28/CD137 antibodies tethered to its phospholipid membrane. The chemical structure of c-diGMP is shown below.

(FIGS. 6A, 6B) Ten days after transplanting luciferase-expressing KPC tumor cells into the pancreas of mice, scaffolds containing either $7\times10^6$ tumor-reactive CAR-T cells, 6 μg c-diGMP, or a combination of both were implanted on the tumor surface; control mice received no treatment. Five days later, peripancreatic lymph nodes were digested into cell suspensions for analysis by flow cytometry. Only lymph nodes that were not engulfed by tumors were used, and they were pooled from at least five animals. (FIG. 6A) Flow cytometry of myeloid maturation markers (CD11b and CD11c): histograms shown on the right depict the expression of the costimulatory factor CD86 and MHC class II molecules after gating on CD11c+CD11b+ double-positive cell populations. (FIG. 6B) Absolute numbers of mature and activated (CD11b+CD11c+CD86+MHC-II+) dendritic cells in peripancreatic lymph nodes. Points represent the cell number per lymph node in samples pooled from 5 mice, and the data are representative of four separate studies.

(FIGS. 7A, 7B) KPC tumors expressing glycoprotein 33 were transplanted into mice. These mice were treated with biomaterial-delivered c-diGMP, CAR-T cells, or a combination of the two and host gp33-specific T cells in the peripheral blood were quantified by tetramer staining. To differentiate endogenous from adoptively transferred T cells, congenic CD45.1 recipient mice were used for these studies. (FIG. 7A) Representative flow cytometry plots showing percentages of gp33 tetramer-positive cells in peripheral blood 10 days after scaffold implantation, gated on CD45.1+ (host) CD8+ cells. Shown profiles are representative of three independent experiments. (FIG. 7B) Absolute numbers of primed (CD45.1+CD8+gp33+) T cells. Shown are ten mice pooled from three independent experiments. Each bar represents the mean absolute cell count±s.e.m. The unpaired Student's t-test was used to test the difference between absolute cell counts.

(FIG. 8A) Serial in vivo bioluminescence imaging of KPC-luc tumors. Shown are five representative mice from each cohort (n=10). (FIG. 8B) Quantified KPC bioluminescent tumor signals; shown are ten mice per treatment group pooled from three independent experiments. (FIG. 8C) Kaplan-Meier survival curves for treated and control mice. ms, median survival. Statistical analysis between the treated experimental and the untreated control group, depicted here, was done using the Log-rank test and $P<0.05$ was considered significant.

(FIG. 9A) Serial in vivo bioluminescence imaging of KPC-luc tumor cells injected intravenously into the four mice that experienced complete tumor regression as described in relation to FIGS. 8A-8C. Age-matched naive mice were used as control. (FIG. 9B) Kaplan-Meier survival curves.

(FIG. 10A) Schematic illustrating scaffolds functionalized with lymphocyte-activating moieties (e.g., anti-CD3/CD28/CD137 antibodies) by covalent coupling of the moieties to a cell scaffold (e.g. Thin Film Nitinol (TFN) micromesh). (FIG. 10B) Schematic illustrating cell scaffolds functionalized with lymphocyte-activating moieties (e.g., anti-CD3/CD28/CD137 antibodies) by covalent coupling of the moieties to lymphocyte-adhesion moieties (e.g., fibrin, collagen) covalently coupled to or coated on a cell scaffold (e.g., TFN micromesh). (FIG. 10C) Schematic illustrating three-dimensional implants formed with multi-layered thin film micromesh (e.g., TFN micromesh) and embedded with an ultra-high density of tumor reactive immune cells (e.g., CAR T cells). (FIG. 10D) Functionalized micropatterned metallic thin film (e.g. TFN micromesh) achieves ultra-high cell densities.

(FIG. 11A) Photograph of a TFN micromesh. Scale bar: 2 mm. (FIG. 11B) Light microscopy image of an uncoated (left panel) and fibrin coated (right panel) TFN micromesh. Magnification: 40×. Scale bar: 120 μm (FIG. 11C) Electron microscopy image of an uncoated (left panel) and fibrin coated (right panel) TFN micromesh. Magnification: 270×1,100× magnified versions are shown in panel (FIG. 11D). (FIG. 11E) Time-lapse video projections of lymphocyte migration through uncoated (left) and fibrin-coated (right) TFN micromeshes tracked for 30 min; each shaded color represents an individual T cell. Scale bar: 50 μm. Shown below are comparison of average velocities and mean T cell displacements, based on 30 randomly chosen cells from two independent experiments. (FIG. 11F) High magnification confocal image of human T cells (Alexa 488-labeled: green) entrapped in a fibrin-coated TFN micromesh. Scale bar: 100 μm. The inset shows a magnification. Scale bar: 50 μm. (FIG. 11G) Schematic diagram of a TFN micromesh functionalized with a T-cell adhesion ligand (fibrin) and stimulatory ligands (anti-CD3/CD28/CD137 antibodies covalently coupled to fibrin by EDC chemistry). (FIG. 11H) Representative carboxyfluorescein succinimidyl ester (CFSE) assay of T cells that have exited TFN micromeshes during the 7d test period, in which proliferation was assessed by measuring CFSE dilution (consequent to cell division) using flow cytometry. Mean CFSE fluorescence intensities (MFI) for the lymphocyte populations are indicated at the upper left.

(FIG. 12C, FIG. 12D). Photomicrographs of a micromesh film or stent. (FIG. 12E, FIG. 12F) The egress of lymphocytes from TFN micromesh was measured by abutting them to a three-dimensional collagen gel (PureCol) containing 10 ng/mL inflammatory cytokine IP-10 and culturing in complete RPMI medium. Microscopy of a TFN micromesh (FIG. 12E) or a stent (FIG. 12F) containing embedded CAR T cells at day 0 or day 2. (FIG. 12G, FIG. 12H) Absolute counts of viable T cells transited from these TFN micromeshes (FIG. 12G) or stents (FIG. 12H) into surrounding collagen matrix. Each line represents one TFN micromesh. Data are representative of three independent experiments. (FIG. 12I) Lymphocytes demonstrate high persistence on TFN micromesh after 6 days. TFN micromesh was loaded with CAR-T cells and placed against a tissue mimetic for 6 days. Ultra-high cell densities were still present on the film after 6 days, indicating favorable lymphocyte persistence can be obtained at tumor sites.

FIGS. 13A-13B. Launching ovarian cancer-specific CAR T cells from bioactive TFN micromeshes eradicates established multifocal disease. One million OVCAR-3 human ovarian cancer cells (expressing the tumor antigen tyrosine kinase-like orphan receptor ROR1 and firefly luciferase) were surgically implanted into the diaphragm of NOD scid gamma (NSG) mice and allowed to establish for 8 weeks. At that time point, all animals developed ovarian cancer lesions mimicking spread to the diaphragm in women with ovarian cancer. Mice were treated with $10\times10^6$ human CAR T cells specific for ROR-1 injected intravenously, injected locally into tumor lesions or $2\times10^6$ cells delivered from an implanted TFN micromesh. (FIG. 13A) Implementation of the approach: [1] Established ovarian cancer lesions in the diaphragm; Li: Liver. Diaph: Diaphragm. Tu: Tumor. [2] implantation of the TFN micromesh loaded with anti-ROR1 CAR T cells between the liver and the diaphragm. [3] TFN micromesh after implantation. (FIG. 13B) Serial in vivo bioluminescence imaging of OVCAR-3-luc tumors.

FIG. 16. Polypeptide sequence of the GFOGER (SEQ ID NO: 1) adhesion motif.

FIG. 17. Polypeptide sequence of an exemplary GFOGER (SEQ ID NO: 1) peptide (SEQ ID NO: 2).

FIG. 18. Polypeptide sequence of the ICAM-1 cell adhesion molecule (SEQ ID NO: 3).

FIG. 19. Polypeptide sequence of the FN-$III_{7-10}$ fragment (SEQ ID NO: 4).

FIG. 20. Exemplary sequences that can be used to engineer chimeric antigen receptors (SEQ ID NOs: 14-27).

DETAILED DESCRIPTION

Figure 1:
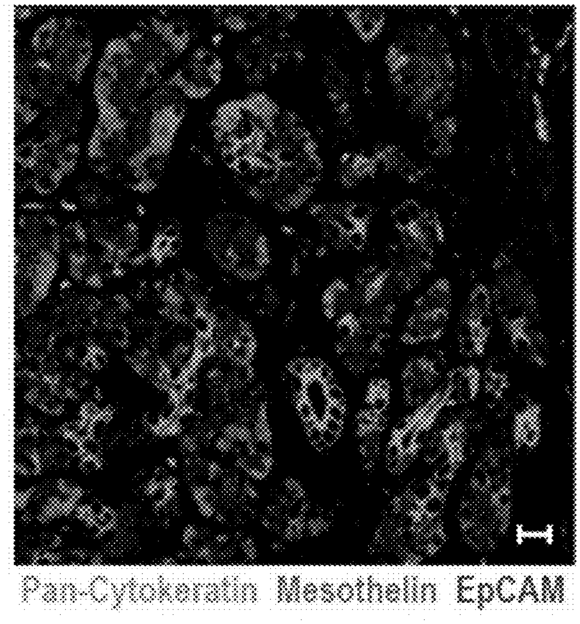
FIG. 1. Solid tumors are heterogeneous and express various levels of antigens commonly used as targets for therapy. This is a representative confocal image of a human pancreatic ductal adenocarcinoma that exhibits the substantial diversity of protein expression by these tumors. Cytokeratin expression commonly occurs in adenocarcinomas, so a pan-cytokeratin antibody was used to define tumor cell populations. The tumor differentiation antigen mesothelin is a likely candidate for immunotherapy, and treatments targeting the cancer stem cell marker EpCAM are currently in clinical development. Scale bar, 100 μm. In color reproductions of this FIG., pan-cytokeratin antibody is green, mesothelin is red, and EpCAM is blue.

Cancer immunotherapy describes a field in which a patient's immune system is used to treat cancer. For example, cancer immunotherapy includes the use of vaccines to immunize patients against the development of cancer. Unfortunately, the responses cancer vaccines can elicit can require months to mature and are usually insufficient to control advanced disease.

Attempts have also been made to more quickly or potently stimulate a patient's own T cells to attack cancer cells. The repertoire of receptors normally expressed by T cells generally has a low affinity to self/tumor antigens, however, so this approach has not achieved sufficient success in the fight against cancer.

An emerging immunotherapy approach involves the alteration of patient-derived lymphocytes (e.g., T cells) with genes encoding chimeric antigen receptors (CARs) that are engineered to have high affinity for selected macromolecular targets in the tumors. The introduced genes can also produce costimulatory signals to elicit robust T cell expansion. The method involves retrieval of T cells from a patient and redirecting them ex vivo to express CARs composed of a tumor-specific single-chain antibody (scFv) fused to costimulatory and CD3ζ signaling domains, which enable the programmed cells to lyse tumor targets in a human leukocyte antigen (HLA)-independent fashion.

Therapies that employ such CAR-programmed T cells have consistently produced positive results in patients with hematologic malignancies in clinical trials. However, when it comes to solid tumors, the effectiveness of these therapies has been limited by: 1) inefficient homing of the lymphocytes to the tumor site; and 2) the immunosuppressive microenvironment solid tumors create. Moreover, 3) CAR-programmed T cells only recognize the tumor antigen for which they have been programmed. The phenotypic diversity of solid tumors, however, means that cancer cells not recognized by the CAR-programmed T cells can form escape variants that elude the programmed T cells. Thus, while the genetic re-programming of T cells remains a promising therapy, significant improvements are required in their use to treat solid tumors.

US 2016/0008399 describes an implantable scaffold that greatly improves the ability of genetically-reprogrammed lymphocytes (e.g., T cells) to treat solid tumors. The implantable scaffolds include genetically-reprogrammed lymphocytes, at least one lymphocyte-adhesion moiety associated with the scaffold; at least one lymphocyte-activating moiety associated with the scaffold, and optionally an immune stimulant.

US 2016/0008399 also describes how the implantable scaffolds create extended second wave protection against tumor cells. Particularly, lymphocytes seeded within the scaffold exit the scaffold following implantation and disperse at high densities throughout, for example, a tumor resection bed and into draining lymph nodes to destroy remaining residual tumor cells following a resection. This step releases large amounts of tumor antigens from dying tumor cells into the tissue. The tumor antigens are subsequently taken up by antigen presenting cells (APCs). By releasing an immune stimulant, the scaffolds can activate APCs and tumor-reactive immune cells to mount a robust host anti-tumor immune response. This “second wave” of anti-tumor immunity is broader and involves multiple cell types acting in synergy to eliminate remaining tumor cells.

STING (STimulator of INterferon Genes) pathway agonists are a type of potent immune stimulant that have been the focus of intense study in cancer immunotherapy. However, like previously described adjuvant compounds (e.g., R848 and related imidazoquinoline TLR7/8 agonists, muramyl dipeptides that trigger (NOD)-like receptors, and RNA oligonucleotide ligands of RIG-I), treatments with unformulated STING agonists are accompanied by systemic inflammatory toxicity, which represents a major hurdle for using these compounds to treat cancer patients. Thus, to be clinically effective, high dosages of STING agonists are required to be repeatedly injected directly into tumor lesions, which limits this therapy to sites that are accessible for daily inoculations (e.g., skin malignancies).

The current disclosure continues to advance cancer immunotherapy by providing an implantable scaffold seeded with (i) genetically-reprogrammed lymphocytes; and (ii) at least one lymphocyte activating moiety. This scaffold overcomes the three problems noted above with cell therapy in solid tumors because 1) the scaffold can be implanted at the site of a solid tumor, thereby overcoming inefficient homing of the lymphocytes to the tumor; the immunosuppressive tumor microenvironment is addressed by the inclusion of lymphocyte stimulating antibodies in the scaffold which encourage T-cell proliferation and tumor cell killing; and 3) inclusion of STING agonists in such a scaffold provides a mechanism to harness their potent immunostimulatory effects without systemic inflammatory toxicity and without the need for daily injections.

The robustness of the anti-cancer effects observed with the disclosed implantable scaffolds were synergistic, unexpected, and remarkable. In almost half of all subjects tested, complete eradication of solid tumors was achieved. Thus, tumor cells recognized by the genetically-reprogrammed lymphocytes as well as tumor cells that normally would have become escape variants were effectively treated. In addition, following complete eradication of solid tumors, subjects were re-challenged with cancer cells. One hundred percent of re-challenged subjects failed to develop any measurable tumors demonstrating the effectiveness of the self-vaccine site. Thus, the implantable scaffolds disclosed herein provide a significant advance in the ongoing fight against solid tumor cancers.

In particular embodiments, the implantable scaffolds disclosed herein can also be simpler in form and easier to manufacture than those described in US 2016/0008399. The implantable scaffolds disclosed herein can also include a STING agonist For clarity, within the current disclosure, heterogenous solid tumors are those including tumor cells that express an antigen targeted by a genetically-reprogrammed lymphocyte (e.g., a genetically-reprogrammed CAR-T cells) and tumor cells that do not express the targeted antigen. Those tumor cells expressing the targeted antigen are targeted solid tumor cells. Tumor cells not expressing the targeted antigen are escape variants.

Various components of the disclosed implantable scaffolds are now described in more detail.

Implantable Scaffold Matrix Materials. The structures of implantable scaffolds disclosed herein can be constructed from a variety of materials.

Figure 10A:
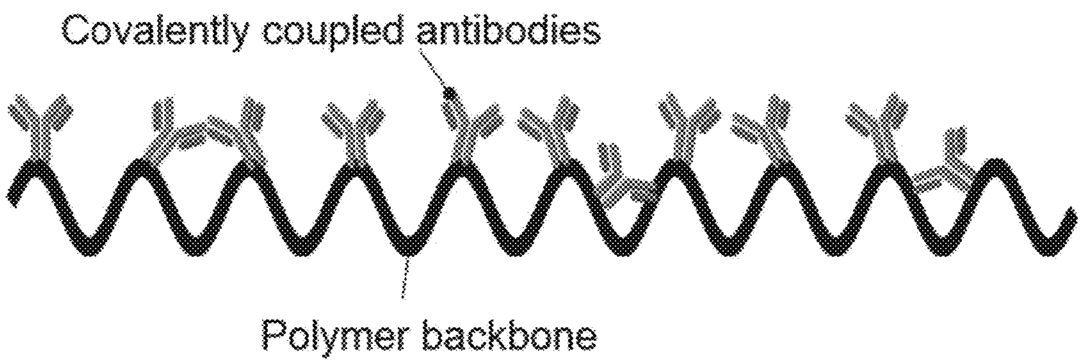
FIGS. 10A-10D.
Figure 10B:
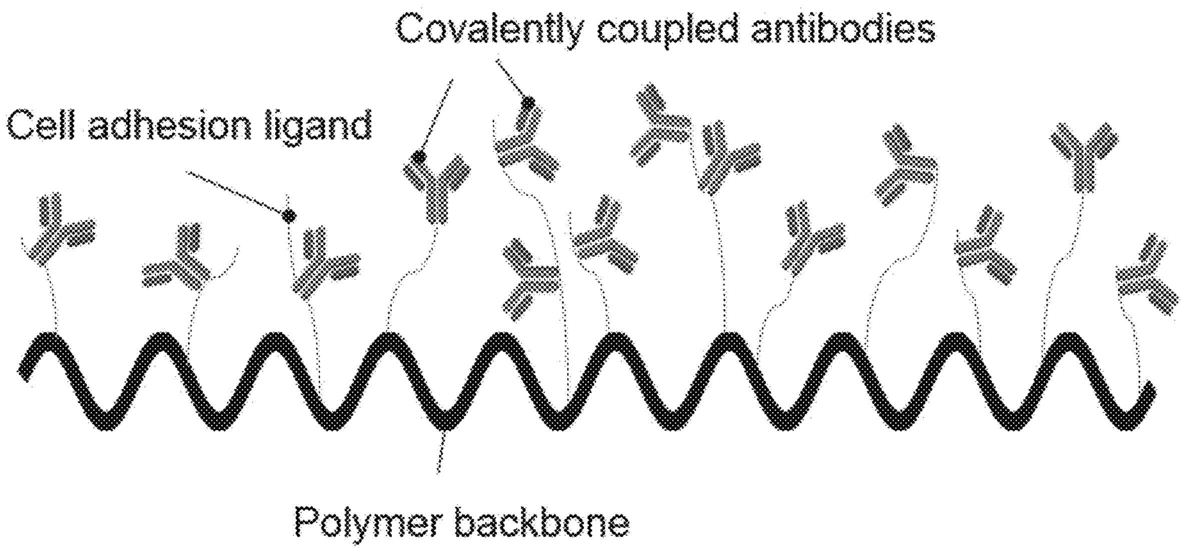
Figure 10C:
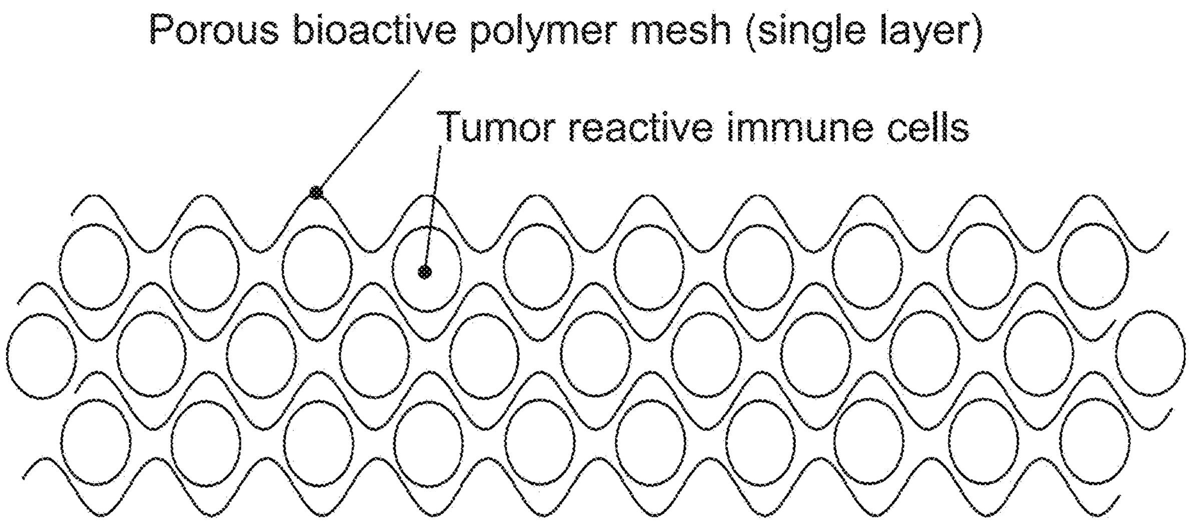

In particular embodiments, the scaffold matrix material includes a micropatterned metallic thin film. Micropatterned metallic thin films are formulated out of at least one metallic material, include a repetitive pattern in their structure, and have a thickness of 100 μm or less. Exemplary metals that can be used for a micropatterned metallic thin film include ELGILOY® (Elgiloy Specialty Metals, Elgin, IL), stainless steel, and nitinol. In particular embodiments, Thin Film Nitinol (TFN) micromesh is used as a scaffold matrix material (e.g., Rigberg et al., *J Vasc Surg.* 2009 August; 50(2):375-80). Nitinol refers to a family of alloys of nickel and titanium that include between 50% and 60% nickel and between 40% and 50% titanium. Up to 2% of the nickel in a nitinol alloy can be replaced with cobalt. TFN micromesh is a variant of the bulk material that is produced on micropatterned silicon wafers via a sputter deposition process. A particular advantage of TFN micromesh is that because it is based on photolithographic technology, one can exert exquisite control over the size and shape of the TFN micromesh pores. TFN micromesh can refer to nitinol in the shape of a thin sheet or film (e.g., 100 μm, 10 μm, 1 μm, or 0.1 μm thick). To enhance the cell cargo capacity of single-layer TFN micromeshes, sandwich-like layer-by-layer thin films with alternating TFN- and cells-layers can be fabricated into three-dimensional structures (as illustrated in FIG. 10C).

In particular embodiments, the scaffold matrix material includes biocompatible polymers. Exemplary biocompatible polymers include agar, agarose, alginate, alginate/calcium phosphate cement (CPC), beta-galactosidase (β-GAL), (1,2,3,4,6-pentaacetyl a-D-galactose), cellulose, chitin, chitosan (see, for example, Levengood et al., J. Mater. Chem. B, 2014, 2, 3161-3184 describing porous chitosan scaffolds), collagen, elastin, gelatin, hyaluronic acid collagen, hydroxyapatite, poly(3-hydroxybutyrate-co-3-hydroxy-hexanoate) (PHBHHx), poly(lactide), poly(caprolactone) (PCL), poly (lactide-co-glycolide) (PLG), polyethylene oxide (PEO), poly(lactic-co-glycolic acid) (PLGA; see, for example, Omar et al., Sci. Transl. Med. 2009 Nov. 25; 1(8): 8ra19 describing porous PLGA scaffolds), polypropylene oxide (PPO), poly(vinyl alcohol) (PVA), silk, soy protein, and soy protein isolate, alone or in combination with any other polymer composition, in any concentration and in any ratio. Blending different polymer types in different ratios using various grades can result in characteristics that borrow from each of the contributing polymers. Various terminal group chemistries can also be adopted.

When injectable implantable scaffolds are used, the scaffold matrix (e.g., polymers) can be responsive to a changed environmental condition following implantation. Polymers with these characteristics are known to those of ordinary skill in the art. For example, in particular embodiments, an injectable in situ gel-forming system is used. In particular embodiments, the polymer formulation can gel in vivo in response to temperature change (thermal gelation), in response to pH change or in response to light. For example, polymers that gel in response to ultraviolet (UV) light can be used. In particular embodiments, the polymer formulation can gel in vivo in response to ionic cross-linking. In particular embodiments, the polymer formulation can gel in vivo in response to solvent exchange. In particular embodiments, the gel used is thermoreversible, pH reversible, or light reversible. In particular embodiments, the gel used is high-viscosity and shear-thinning. In additional gelling embodiments, the gel can be a gel formed from any appropriate polymer. Injectable, spontaneously assembling scaffolds fabricated from mesoporous silica rods are described in Kim et al., Nature Biotechnology 33, 64-72 (2015).

Self-assembling peptide scaffolds can also be used as scaffold matrix materials (see, e.g., Zacco et al., Biomacromolecules. 2015 Jul. 13; 16(7): 2188-97).

In particular embodiments, alginate is used as a scaffold matrix material, either separately or in combination with one or more other materials. Alginate is easily processed, water soluble, and non-immunogenic. Alginate is a biodegradable anionic polysaccharide with free hydroxyl groups that offer easy gelling. In alternative embodiments, the polymer may be a polyelectrolyte complex mixture (PEC) formed from a 1:1 solution of alginate and chitosan.

In particular embodiments, a structure (e.g., scaffold matrix material) may formed from an alginate/calcium carbonate/glucono-delta-lactone mixture, such as 0.5-5% alginate, 0.5-15 g/L calcium carbonate, and 1-50 g/L gluconon-delta-lactone in a ratio of 2:1:1 (alginate:$CaCO_3$:GDL). Polymer structures may also include varying amounts of gelatin in combination with varying amounts of alginate. Depending on the materials and material ratios in mixture, the structures may optionally be cross-linked. Collagen/alginate hybrid scaffolds such as those described in Lee at al., Chem. Mater., 2012, 24(5), 881-891 can also be used.

In particular embodiments, polymer solutions having varying amounts of polymer dissolved in an acidic solution can be used to form the structures disclosed herein. The concentration of the acid can be adjusted depending on the amount of polymer dissolved. In one aspect, the acidic solution is 1% (v/v) acetic acid. In particular embodiments, the amount of polymer in solution is between 0.5-5% (w/v) and any whole or partial increments therebetween. For example, the amount of polymer in solution (w/v) can be 0.5%, 1%, 1.5%, 2%, 2.5%, 3%, 3.5%, 4%, 4.5% or 5%. In particular embodiments, the amount of polymer in solution is 2.4% (w/v). In other various embodiments, the polymer is dissolved in at least one of water, acid, acetic acid, camphene, or camphene-naphthalene.

When gelatin is incorporated, the concentration of the acid can be adjusted depending on the amount of gelatin in combination with polymer (in particular embodiments, alginate) that is dissolved. In one aspect, the acidic solution is 1% (v/v) acetic acid. In particular embodiments, the amount of gelatin in solution is between 1-10% (w/v) and any whole or partial increments therebetween. For example, the amount of alginate in solution (w/v) can be 1%, 2%, 3%, 4%, 5%, 6%, 7%, 8%, 9% or 10%. In particular embodiments, the amount of alginate in solution is 5.5% (w/v). In particular embodiments, the polymer solution includes a combination of 2.4% (w/v) alginate solution and a 5.5% (w/v) gelatin solution. In other various embodiments, the gelatin in combination with varying amounts of alginate is dissolved in at least one of water, acid, acetic acid, camphene, or camphene-naphthalene.

In particular embodiments, polymer-based scaffolds can be formed as follows: a weight by volume (w/v) polymer solution in deionized (DI) water can be prepared and filtered with a 0.45 micrometer bottle filter to remove any particles and then frozen to −80° C. The frozen sample can be lyophilized in a 4.5 liter benchtop freeze dry system (Labconco, Kansas City, MO). The filtered lyophilized polymer can be reconstituted into solutions of various concentrations (0.1%-5%) with water or buffer.

Crosslinking can be performed with, for example, calcium chloride and/or calcium carbonate. Calcium carbonate is a slow crosslinker, with samples taking up to several hours to fully crosslink. To increase the speed of the reaction gluconodeltalactone (GDL) can be added. Calcium chloride is a fast crosslinker and the samples will fully gel in a few minutes. In one method, the addition of $CaCl_2$ to the polymer solution can occur prior to freezing. Other methods include use of a 5.5% (w/v) solution of calcium carbonate+GDL added to the polymer solution prior to initial freezing.

In particular embodiments, polymer solutions can be degassed in a speed mixer and poured slowly into casts to prevent bubbles from forming. When pipetting the polymer solutions into small molds, air bubble formation can be avoided by placing a micropipette on the open end of mold grooves and repeatedly flushing the entire canal system until the residual air is flushed out.

Freeze casting can be used to form the scaffolds disclosed herein. Various polymer solutions can be freeze cast into various sized casts as would be understood by those skilled in the art. The rate of cooling should be controlled as it affects the size and alignment of pores, as well as the formation of ridges. In particular embodiments, the cooling rate can range between 0.1-100° C. per minute (m) and any whole or partial increments therebetween. In particular embodiments, the cooling rate can range between 1-10° C./m, and any whole or partial increments therebetween. For example, the cooling rate (° C./m) can be 0.1, 0.5, 1, 2, 3, 4, 5, 5.5, 6, 6.5, 7, 7.5, 8, 8.5, 9, 9.5, or 10.

In particular embodiments, in preparing an alginate scaffold, an alginate/calcium carbonate/glucono-delta-lactone mixture can be prepared by stirring, with concentrations ranging from 0.5-5 wt % alginate, 0.5-15 g/L calcium carbonate, and 1-50 g/L glucono-delta-lactone in a volume ratio of 2:1:1 (alginate:$CaCO_3$:GDL) as a “pre-gelling” process. In particular embodiments, the resulting mixture can be freeze cast (directionally frozen) at a constant cooling rate (0.1°/min-10°/min) until solid and lyophilized until dry. The dried scaffolds can be crosslinked in 0.1-2.5 wt. % calcium chloride for 5-30 minutes and washed in HEPES buffered saline prior to any further use of the scaffold.

In particular embodiments, in preparing an alginate-chitosan scaffold, an alginate-chitosan polyelectrolyte complex (PEC) mixture can be prepared by sonicating or homogenizing on ice in a range of 1:1 to 1:9 solutions (both ways) of alginate (prepared in water) and chitosan (prepared in 1% acetic acid) and total polymer content ranging from 0.5%-5%. The pH of the resulting mixture can be adjusted with NaOH up to 10.0. In particular embodiments, the alginate-chitosan PEC mixture can be freeze cast at a constant cooling rate (0.1°/min-10°/min) until solid and lyophilized until dry. Dried scaffolds can be crosslinked in 0.1-2.5% calcium chloride for 5-30 minutes and washed in PBS prior to any further use of the scaffold.

Implantable scaffolds can also be manufactured from various materials using 3D bioprinting (see, e.g., Singh et al., *Polymers* 2016, 8(1), 19; and An et al., *Engineering*, Volume 1, Issue 2, June 2015, Pages 261-268).

Lymphocyte-Activating Moieties. Particular embodiments of the implantable scaffolds disclosed herein may also include Lymphocyte-Activating Moieites (LAM). LAM include any compound that activates a lymphocyte and can be incorporated in or attached to the implantable scaffolds disclosed herein. Activation of a lymphocyte refers to the state of a lymphocyte that has been sufficiently stimulated to induce detectable cellular proliferation, cytokine production, or effector function such as tumor targeting and/or killing. If the lymphocyte is a T-cell, activation also results in expression of cell surface markers particular to the T-cell type. Exemplary LAM include IL-15, CD3, CD27, CD28, CD80, CD86, 4-1BB, CD137, OX40, CD30, CD40, LFA-1, CD2, CD7, LIGHT, NKG2C, B7-H3, and CD83 ligands or antibodies, CD1d, recombinant CD1d molecules preloaded with α-galactosyl ceramide and/or recombinant major histocompatibility complex (MHC) molecules loaded with defined tumor antigens or peptides to selectively expand particular lymphocyte types embedded within a scaffold. Exemplary LAM for NK cells include IL-15 and CD137.

STING Agonists. "STING" is an abbreviation of "stimulator of interferon genes", which is also known as "endoplasmic reticulum interferon stimulator (ERIS)", "mediator of IRF3 activation (MITA)", "MPYS" or "transmembrane protein 173 (TM173)". STING is a transmembrane receptor protein and is encoded by the gene TMEM173 in human. Activation of STING leads to production of Type I interferons (e.g. IFN-a and IFN-β), via the IRF3 (interferon regulatory factor 3) pathway; and to production of pro-inflammatory cytokines (e.g. TNF-a and IL-1β), via the NF-κB pathway and/or the NLRP3 inflammasome.

Human and murine STING are naturally activated two ways: via binding of exogenous (3',3) cyclic dinucleotides (c-diGMP, c-diAMP and c-GAMP) that are released by invading bacteria or archaea; and via binding of (2',3')cyclic guanosine monophosphate-adenosine monophosphate ((2',3')c-GAMP), an endogenous cyclic dinucleotide that is produced by the enzyme cyclic GMP-AMP synthase (cGAS; also known as C6orfl50 or MB21D1) in the presence of exogenous double-stranded DNA (e.g. that released by invading bacteria, viruses or protozoa).

The term "STING agonist" refers to a substance that activates the STING receptor in vitro or in vivo. A compound can be deemed a STING agonist if: (i) induces Type I interferons in vitro in human or animal cells that contain STING; and (ii) does not induce Type I interferons in vitro in human or animal cells that do not contain STING or does not contain functioning STING. A typical test to ascertain whether a ligand is a STING agonist is to incubate the ligand in a wild-type human or animal cell line and in the corresponding cell line in which the STING coding gene has been genetically inactivated by a few bases or a longer deletion (e.g. a homozygous STING knockout cell line). An agonist of STING will induce Type I interferon in the wild-type cells but will not induce Type I interferon in the cells in which STING is inactivated.

In particular embodiments, STING agonists include cyclic molecules with one or two phosphodiester linkages, and/or one or two phosphorothioate diester linkages, between two nucleotides. This includes (3',5')-(3',5') nucleotide linkages (abbreviated as (3',3')); (3',5')-(2',5') nucleotide linkages (abbreviated as (3',2')); (2',5')-(3',5') nucleotide linkages (abbreviated as (2',3')); and (2',5')-(2',5') nucleotide linkages (abbreviated as (2',2')). "Nucleotide" refers to any nucleoside linked to a phosphate group at the 5', 3' or 2' position of the sugar moiety.

In particular embodiments, STING agonists include compounds of the formula:

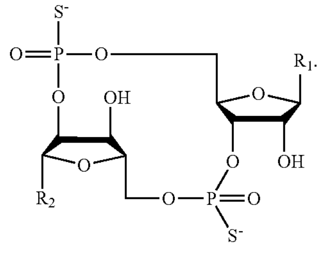

In particular embodiments, R1 and R2 may be independently 9-purine, 9-adenine, 9-guanine, 9-hypoxanthine, 9-xanthine, 9-uric acid, or 9-isoguanine, as shown below:

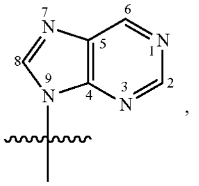

9-purine

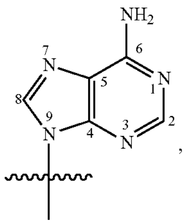

9-adenine

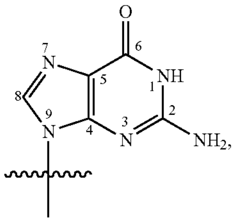

9-guanine

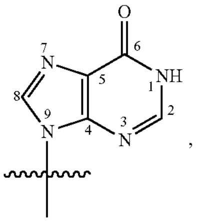

9-hypoxanthine

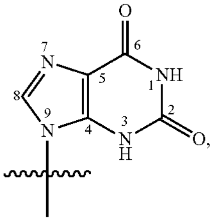

9-xanthine

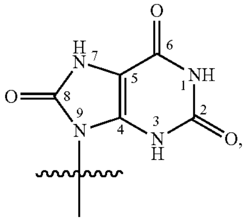

9-uric acid

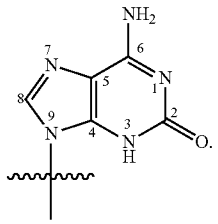

9-isoguanine

Figure 5A:
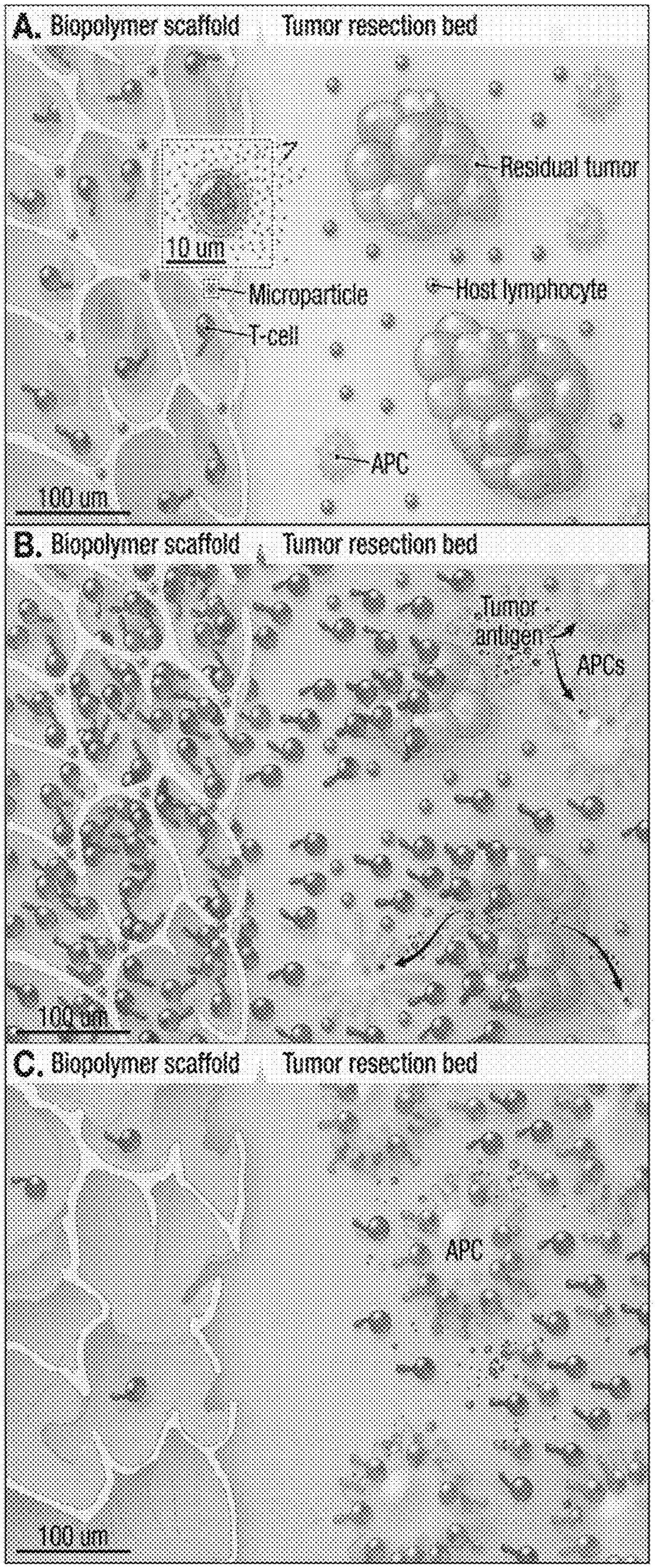
FIGS. 5A, 5B. Design of a biomaterial carrier that co-delivers CAR-expressing T cells and an immune stimulant (shown as a vaccine adjuvant in this example) to simultaneously clear heterogeneous cancer cells and establish systemic anti-tumor immunity.
Figure 5B:
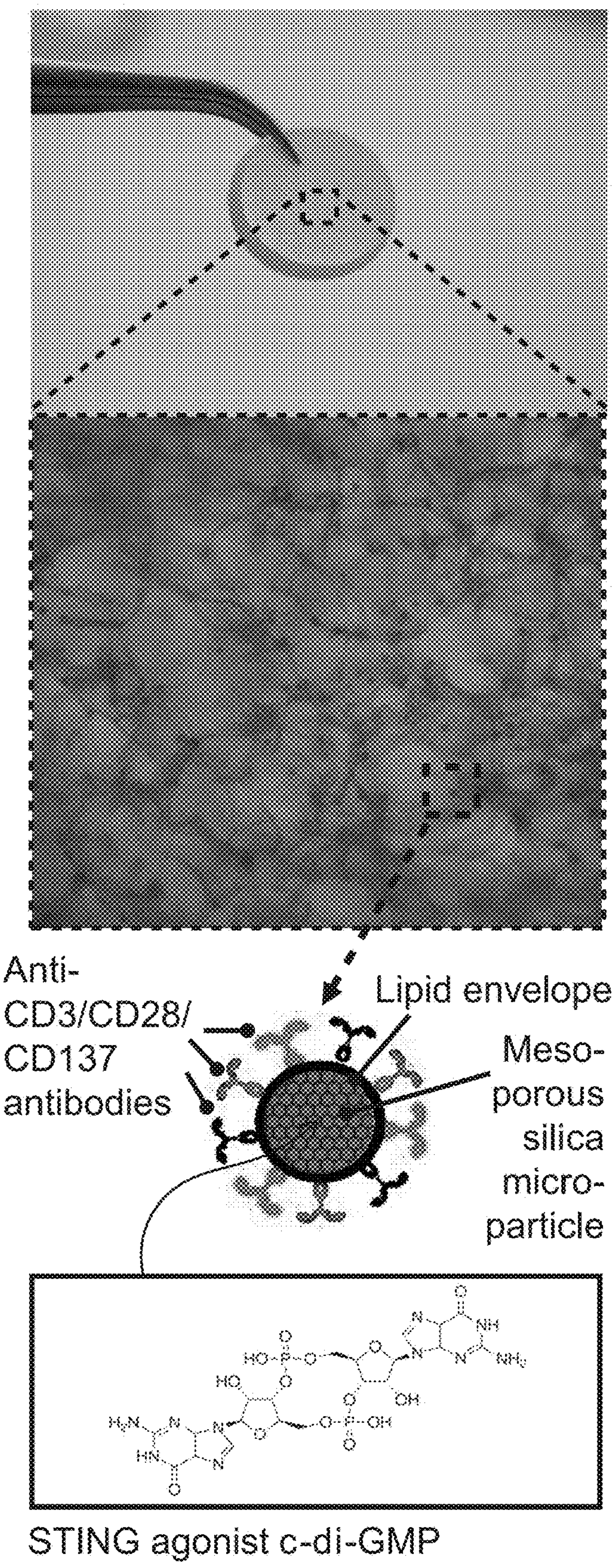

In particular embodiments, the STING agonist can include dithio-($R_P$, $R_P$)-[cyclic[A(2',5')pA(3',5')p]] (also known as 2'-5', 3'-5' mixed phosphodiester linkage (ML) RR-S2 c-di-AMP or ML RR-S2 CDA), ML RR-S2-c-di-GMP (ML-CDG), ML RR-S2 cGAMP, or any mixtures thereof.
The structure of c-diGMP is shown in FIG. 5B. The structure of c-diAMP includes:
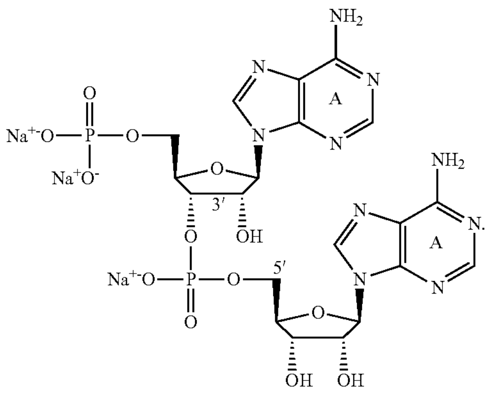
The structure of c-GAMP includes:
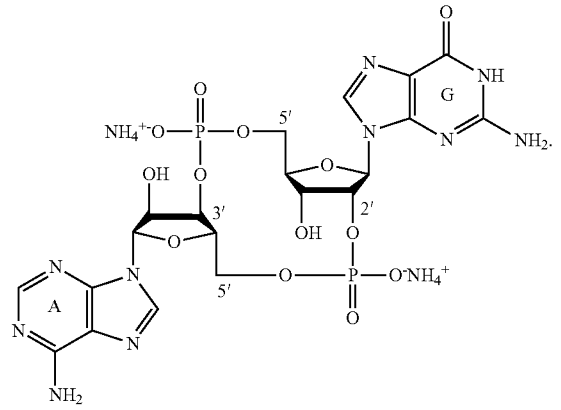
Additional particular examples of STING agonists include:
| Name | Structure |
| --- | --- |
| c-AIMP | 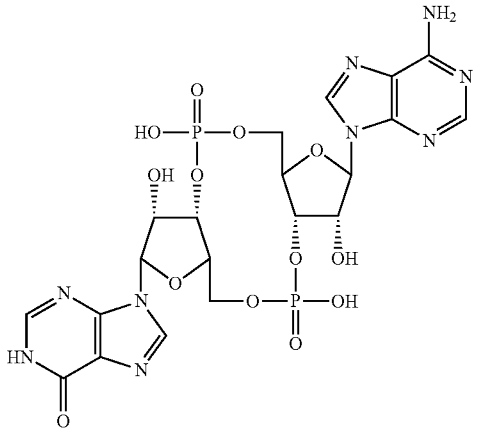 |
| (3',2')c-AIMP | 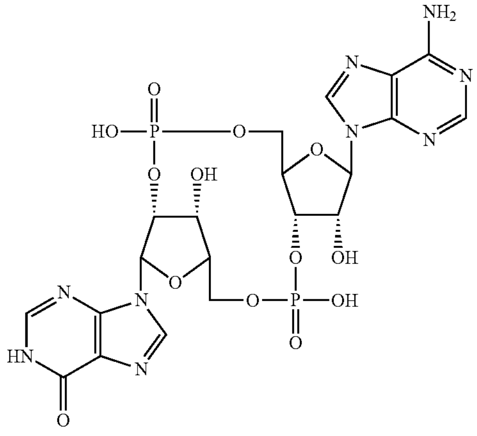 [SMILES: Nc1ncnc2c1ncn2C1OC2COP(=O)(O)O[C@H]3C(n4cnc5c(=O)[nH]cnc54)OC(COP(=O)(O)O[C@H]2[C@H]1O)[C@H]3O] |

-continued
| Name | Structure |
| --- | --- |
| (2',2')c-AIMP | 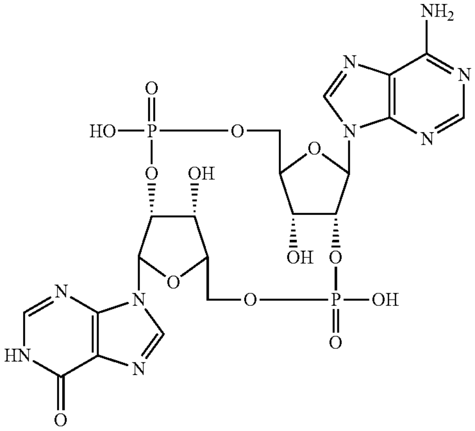 [SMILES: Nc1ncnc2c1ncn2C1OC2COP(=O)(O)O[C@H]3C(n4cnc5c(=O)[nH]cnc54)OC(COP(=O)(O)O[C@@H]1[C@@H]2O)[C@H]3O] |
| (2',3')c-AIMP | 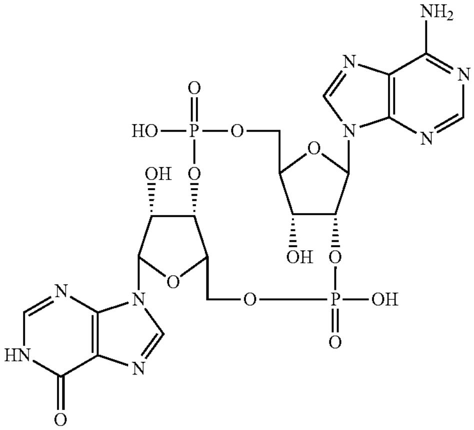 [SMILES: Nc1ncnc2c1ncn2C1OC2COP(=O)(O)O[C@@H]3C(COP(=O)(O)O[C@@H]1[C@@H]2O)OC(n1cnc2c(=O)[nH]cnc21)[C@@H]3O] |
| c-AIMP(S) | 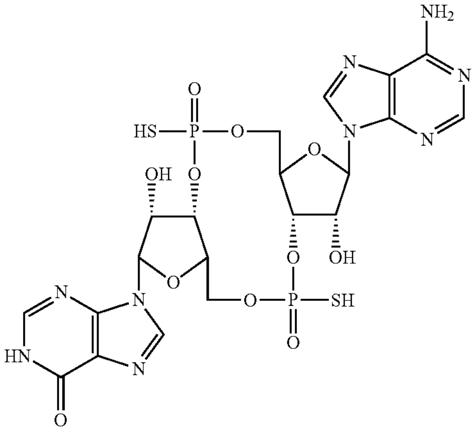 [SMILES: Nc1ncnc2c1ncn2C1OC2COP(=O)(S)O[C@@H]3C(COP(=O)(S)O[C@H]2[C@H]1O)OC(n1cnc2c(=O)[nH]cnc21)[C@@H]3O] |

-continued
| Name | Structure |
|---|---|
| c-(dAMP-dIMP) | 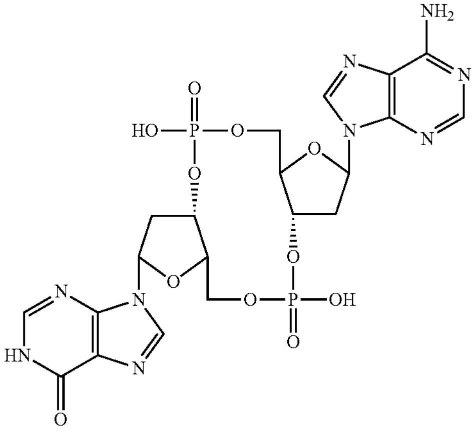 [SMILES: Nc1ncnc2c1ncn2C1C[C@@H]2OP(=O)(O)OCC3OC(n4cnc5c(=O)[nH]cnc54)C[C@@H]3OP(=O)(O)OCC2O1] |
| c-(dAMP-2'FdIMP) | 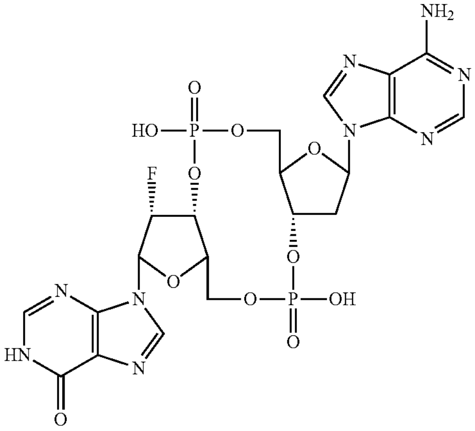 [SMILES: Nc1ncnc2c1ncn2C1C[C@@H]2OP(=O)(O)OCC3OC(n4cnc5c(=O)[nH]cnc54)[C@H](F)[C@@H]3OP(=O)(O)OCC2O1] |
| c-(2'FdAMP-2'FdIMP) | 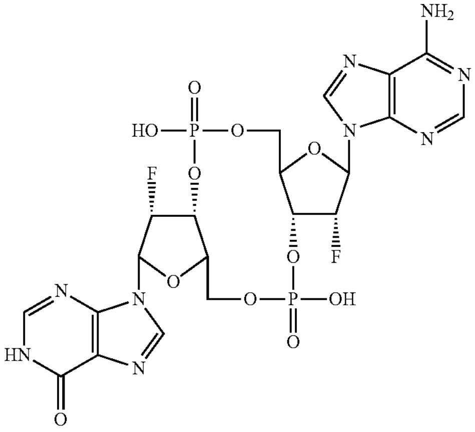 [SMILES: Nc1ncnc2c1ncn2C1OC2COP(=O)(O)O[C@@H]3C(COP(=O)(O)O[C@H]2[C@H]1F)OC(n1cnc2c(=O)[nH]cnc21)[C@@H]3F] |

-continued
| Name | Structure |
|---|---|
| (2',3')c-(AMP-2'FdIMP) | 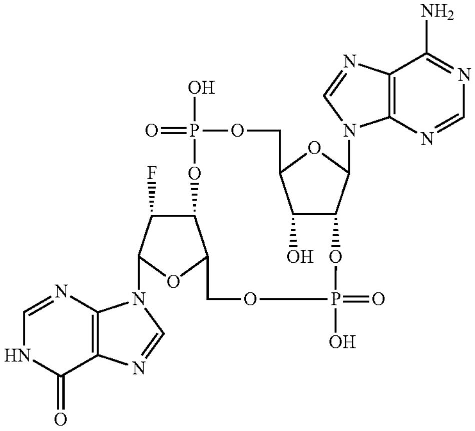 [SMILES: Nc1ncnc2c1ncn2C1OC2COP(=O)(O)O[C@@H]3C(COP(=O)(O)O[C@@H]1[C@@H]2O)OC(n1cnc2c(=O)[nH]cnc21)[C@@H]3F] |
| c-[2'FdAMP(S)-2'FdIMP(S)] | 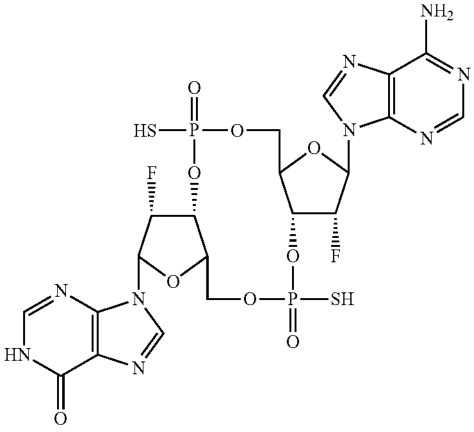 |
| c-[2'FdAMP(S)-2'FdIMP(S)](P0M)[2] | 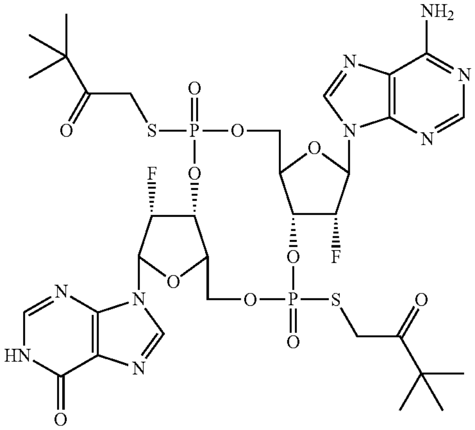 [SMILES: CC(C)(C)C(=O)CSP1(=O)OCC2OC(n3cnc4c(=O)[nH]cnc43)[C@H](F)[C@@H]2OP(=O)(SCC(=O)C(C)(C)C)OCC2OC(n3cnc4c(N)ncnc43)[C@H](F)[C@@H]2O1] |

Examples of STING agonists also include DMXAA:

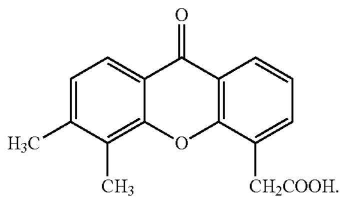

Additional examples of STING agonists are described in WO2016/145102.

The optional uses of additional immune stimulants and lymphocyte-adhesion moieties are described next.

Additional Immune Stimulants. In particular embodiments, immune stimulants in addition to STING agonists can be included. In particular embodiments, the immune stimulant is a cytokine, an antibody, a small molecule, an siRNA, a plasmid DNA, and/or a vaccine adjuvant.

Exemplary cytokines include IL-2, IL-7, IL-12, IL-15, IL-18, IL-21, TNFα, IFN-α, IFN-β, IFN-γ, or GM-CSF. In particular embodiments, the immune stimulant may be a cytokine and or a combination of cytokines, such as IL-2, IL-12 or IL-15 in combination with IFN-α, IFN-β or IFN-γ, or GM-CSF, or any effective combination thereof, or any other effective combination of cytokines. The above-identified cytokines stimulate $T_H1$ responses, but cytokines that stimulate $T_H2$ responses may also be used, such as IL-4, IL-10, IL-11, or any effective combination thereof. Also, combinations of cytokines that stimulate $T_H1$ responses along with cytokines that stimulate $T_H2$ responses may be used.

Exemplary antibodies include anti-PD1, anti-PDL1, anti-CTLA-4, anti-TIM3, agonistic anti-CD40, agonistic anti-4-1BB, and/or bispecific antibodies (e.g., BITE-antibodies: anti-CD3/anti-tumor antigen). Exemplary small molecule drugs include, TGF-beta inhibitors, SHP-inhibitors, STAT-3 inhibitors, and/or STAT-5 inhibitors. Any siRNA capable of down-regulating immune-suppressive signals or oncogenic pathways (such as kras) can be used whereas any plasmid DNA (such as minicircle DNA) encoding immune-stimulatory proteins can be used. Exemplary vaccine adjuvants, include any kind of Toll-like receptor ligand or combinations thereof (e.g. CpG, Cpg-28 (a TLR9 agonist), Polyriboinosinic polyribocytidylic acid (Poly(I:C)), α-galactoceramide, MPLA, Motolimod (VTX-2337, a novel TLR8 agonist developed by VentiRx), IMO-2055 (EMD1201081), TMX-101 (imiquimod), MGN1703 (a TLR9 agonist), G100 (a stabilized emulsion of the TLR4 agonist glucopyranosyl lipid A), Entolimod (a derivative of *Salmonella* flagellin also known as CBLB502), Hiltonol (a TLR3 agonist), and Imiquimod), and/or inhibitors of heat-shock protein 90 (Hsp90), such as 17-DMAG (17-dimethylaminoethylamino-17-demethoxygeldanamycin).

Immune stimulants derived from the molecules noted in the preceding paragraphs can also be used. For example, RLI is an IL-15-IL-15 receptor-α fusion protein that exhibits 50-fold greater potency than IL-15 alone. IL-15 impacts the anti-tumor immune response at multiple points. It can differentiate monocytes into stimulatory antigen presenting cells; promote the effector functions and proliferation of tumor-reactive T-cells; and recruit and activate NK cells.

Lymphocyte-Adhesion Moieties. The disclosed scaffolds can include lymphocyte-adhesion moieties to promote lymphocyte mobility out of the implanted scaffolds. Lymphocyte-adhesion moieties include cell-adhesion moieties such as cell-adhesion polypeptides that mimic the extracellular matrix (such as collagen). As used herein, "cell adhesion polypeptides" refer to compounds having at least two amino acids per molecule which are capable of binding via cell surface molecules, such as integrin. The cell adhesion polypeptides may be any of the proteins of the extracellular matrix which are known to play a role in cell adhesion, including fibrin, fibronectin, vitronectin, laminin, elastin, fibrinogen, collagen types I, II, and V, as described in Boateng et al., Am. J. Physiol.—Cell Physio. 288:30-38 (2005). Additionally, the cell adhesion polypeptides may be any peptide derived from any of these proteins, including fragments or sequences containing the binding domains. Cell adhesion polypeptides include those having integrin-binding motifs, such as the ICAM-1 motif, and related peptides that are functional equivalents. Cell adhesion polypeptides may also be any of the peptides described in U.S. Patent Publication No. 20060067909.

In particular embodiments, the structures include compounds having lymphocyte-adhesion moieties, such as a ligand for $\alpha_1\beta_1$ integrin, a ligand for $\alpha_2\beta_1$ integrin, a ligand for $\alpha4\beta_1$ integrin, a ligand for $\alpha_5\beta_1$ integrin, a ligand for lymphocyte function-associated antigen (LFA-1), or combinations thereof. In particular embodiments, the ligand interacts specifically with one integrin. In particular embodiments, the ligand is not a complete fibronectin molecule or is not a complete collagen molecule.

The lymphocyte-adhesion moiety can be a peptide, antibody, or a small organic molecule. A small organic molecule refers to a carbon-based molecule having a molecular weight of 500 daltons or less. The antibody or an integrin binding fragment thereof can be single chained, humanized, or chimeric. In particular embodiments, the lymphocyte-adhesion moiety can be a collagen-mimetic peptide, for example a stable triple-helical, collagen-mimetic peptide that contains the GFOGER (SEQ ID NO: 1) adhesion motif from type I collagen, GFP*GER (SEQ ID NO: 1), wherein P* is 4-hydroxyproline, which is recognized by the $\alpha_2\beta_1$ integrin. This peptide adopts a stable triple-helical conformation similar to the native structure of type I collagen. "GFOGER (SEQ ID NO: 1) peptide" can refer to a collagen-mimetic peptide containing a GFOGER (SEQ ID NO: 1) adhesion motif. An exemplary GFOGER (SEQ ID NO: 1) peptide sequence is $GGYGGGPC(GPP)_5GFP*GER(GPP)_5GPC$ (SEQ ID NO: 2), wherein P* is 4-hydroxyproline.

Particular embodiments utilize ICAM-1 as a lymphocyte-adhesion moiety. ICAM-1 is an Ig-like cell adhesion molecule that binds integrins promoting cell-cell adhesion and is a ligand for lymphocyte function-associated (LFA) antigens. ICAM-1 is found primarily on monocytes and endothelial cells, and is widely inducible, or upregulated, on many cells including T-cells, B-cells, thymocytes, dendritic cells, endothelial cells, fibroblasts, keratinocytes, chondrocytes, and epithelial cells. This protein has a co-stimulatory effect upon cytotoxic T-cell interaction, and is utilized in a number of intercellular binding interactions. In particular embodiments, ICAM-1 includes SEQ ID NO: 3.

Particular embodiments utilize $FNIII_{7-10}$ as a lymphocyte-adhesion moiety. $FNIII_{7-10}$ is a fibronectin fragment spanning the 7-10th type III repeats of fibronectin. The sequence of fibronectin is known in the art. In particular embodiments, $FNIII_{7-10}$ includes SEQ ID NO: 4.

Various methods can be utilized to incorporate LAM, STING agonists, additional immune stimulants and/or lymphocyte-activating moieties into or onto the implantable scaffolds disclosed herein. For purposes of this discussion the LAM, STING agonists, additional immune stimulants and/or lymphocyte-activating moieties are referred to as "components."

Components can be found within injectable forms of the structures or embedded within the pores of the scaffolds, attached to the surface of the scaffolds, coated on to the surface of the scaffolds, and/or embedded within the scaffolds themselves.

Within particular embodiments, components may be incorporated into the backbone of a polymer chain. For example, a polymer can be created containing YIGSR (SEQ ID NO: 5) in the backbone as described in Jun et al., J. Biomaterials Sci., Polymer Ed. 15(1), 73-94 (2004).

In particular embodiments, the components may be grafted onto a polymer. In one method, polymers having side branches containing reactive functional groups such as epoxide, halide, amine, alcohol, sulfonate, azido, anhydride, or carboxylic acid moieties can be covalently linked to the amine terminus of polypeptides via the reactive side branches using conventional coupling techniques such as carbodiimide reactions. For example, RGD (Arg-Gly-Asp)-containing peptides have been grafted onto the backbone of polymers as described in Lin, et al., J. Biomedical Materials Res, 28(3), 329-42 (1994). In another example, RGD-containing peptides have been grafted onto the side branches of polyethylene glycol based polymers, as described in Hansson, et al., Biomaterials, 26, 861-872 (2005). In particular embodiments, components can be directly coupled to an implantable scaffold backbone (illustrated in FIG. 10A), or coupled to the lymphocyte-adhesion moieties (e.g. Fibrin, Collagen; illustrated in FIG. 10B) using carbodiimide chemistry prior to scaffold formation (e.g., molding).

The advantage of these approaches from a manufacturing perspective is that the implanted scaffolds are entirely composed of a single biodegradable material without using particles as a second component. In addition, the strategy of integrating LAM into the scaffold can bypass the need to use lymphocyte-adhesion moieties. Without being bound by theory, in these embodiments, scaffold-embedded lymphocytes migrate along the displayed LAM (e.g., anti-CD3, anti-CD28, anti-CD137 antibodies, IL-15), which serve as adhesion molecules and stimulatory cues. This approach renders the use of particles and lymphocyte-adhesion moieties optional in embodiments disclosed herein.

In manufacturing, 3D bioprinting can better ensure well-defined scaffold porosity and composition and could facilitate GM P-manufacturing. In this scenario, components could also be printed into the scaffolds to better ensure controlled spatial distribution of these components within the scaffold.

As previously indicated, TFN micromesh is a variant of the bulk material that is produced on micropatterned silicon wafers via a sputter deposition process. A particular advantage of TFN micromesh is that because it is based on photolithographic technology, one can also exert exquisite control over the size and shape of its micromesh pores.

In particular embodiments, scaffolds can also be coated with a bioactive coating (e.g., a drug eluting polymer) including one or more components. In particular embodiments, the scaffold is at least partially coated with a bioactive coating. The bioactive coating can be applied onto the surface of the scaffold in various ways, including the use of coating methods that are known in the art. For example, the bioactive coating (e.g., a drug eluting polymer) may be sprayed onto the scaffold by a conventional electrostatic spraying process, resulting in charged droplets being deposited onto the surface of the scaffold. As the coating fluid dries, the components, for example, polypeptides and/or small molecules, remain adhered to the surface of the scaffold, for example, by inter-molecular bonding with the side-chain groups on the polypeptides. In particular embodiments, the deposited bioactive coating may form a monolayer on the surface of the scaffolding.

In particular embodiments, the bioactive coating may be bonded to the surface of a scaffold by any type of chemical or physical bonding means, including covalent, polar, ionic, coordinate, metallic, electrostatic, or intermolecular dipolar (including Van der Waals) bonds. Bioactive coatings can additionally include other components to alter the surface of the scaffold, for example polylysine, polyornitine, or other glycoproteins.

Exemplary biocompatible polymers that can be used as drug eluting polymers include agar, agarose, alginate, alginate/calcium phosphate cement (CPC), beta-galactosidase (β-GAL), (1,2,3,4,6-pentaacetyl a-D-galactose), cellulose, chitin, chitosan (see, for example, Levengood et al., J. Mater. Chem. B, 2014, 2, 3161-3184 describing porous chitosan scaffolds), collagen, elastin, gelatin, hyaluronic acid collagen, hydroxyapatite, poly(3-hydroxybutyrate-co-3-hydroxy-hexanoate) (PHBHHx), poly(lactide), poly(caprolactone) (PCL), poly(lactide-co-glycolide) (PLG), polyethylene oxide (PEO), poly(lactic-co-glycolic acid) (PLGA; see, for example, Omar et al., Sci. Transl. Med. 2009 Nov. 25; 1(8): 8ra19 describing porous PLGA scaffolds), polypropylene oxide (PPO), poly(vinyl alcohol) (PVA), silk, soy protein, and soy protein isolate, alone or in combination with any other polymer composition, in any concentration and in any ratio.

In particular embodiments, for placement of a bioactive coating, surfaces of the scaffolds can be coated in polylysine or polyornithine (0.1-1.0 mg/ml for 3-10 minutes) followed by coating in a protein, such as a LAM (e.g., anti-CD3, anti-CD28, and/or anti-CD137 antibodies, and/or IL-15) and/or a GFOGER (SEQ ID NO: 1) peptide or fibrin (10 μg/ml-250 μg/ml for 30 minutes-24 hours).

In particular embodiments, for placement of a bioactive coating, surfaces of the scaffolds can be coated in polylysine or polyornithine (0.5 mg/ml for 6 minutes) followed by coating in a protein, such as a LAM (e.g., anti-CD3, anti-CD28, and/or anti-CD137 antibodies and/or IL-15) and/or a GFOGER (SEQ ID NO: 1) peptide or fibrin (10 μg/ml-250 μg/ml for 30 minutes-24 hours).

In particular embodiments, the surface of the scaffold is coated with LAM and/or a GFOGER (SEQ ID NO: 1) peptide. As an example, the purified LAM and/or GFOGER (SEQ ID NO: 1) peptide or fibrin could be stored as a trifluoroacetic acid (TFA) salt and reconstituted to 10 mg/mL in 0.1% TFA and 0.01% sodium azide and stored at 4° C. prior to use. After the scaffolds are rinsed with ethanol to remove contaminants, cleaned in fresh ethanol, rinsed in $ddH_2O$, they can be soaked in phosphate buffered saline (PBS). The LAM and/or GFOGER (SEQ ID NO: 1) peptide or fibrin can then be absorbed onto the scaffolds passively by incubating the scaffolds in a solution of LAM and/or GFOGER (SEQ ID NO: 1) peptide or fibrin in PBS. Prior to implantation, scaffolds could be rinsed in PBS to remove unbound peptides.

In particular embodiments, a bioactive coating such as a drug eluting polymer can be coated on a scaffold matrix material (e.g., TFN micromesh or alginate). A drug eluting polymer may, for example, contain a small molecule (e.g., a STING agonist), and may slowly elute the small molecule over time (e.g., 3, 4, or 5 days, 1 week, or 2 weeks).

In particular embodiments, a drug eluting polymer (e.g., PLGA) directly coats the surface of the scaffold matrix as a monolayer, and other components of the lymphocyte scaffold (e.g., lymphocyte-activating moieties) may be applied over the drug eluting polymer. A drug eluting polymer can be useful, for example, for slowly eluting a small molecule or drug from the coating into an environment where the lymphocyte scaffold is implanted.

As indicated, components can be incorporated directly into or onto the structure of an implantable scaffold. In particular embodiments, components can be incorporated into or onto particles. Porous particles can be constructed from any material capable of forming a porous network. Exemplary materials include a variety of material such as biocompatible polymers, metals, transition metals and metalloids. Exemplary biocompatible polymers include agar, agarose, alginate, alginate/calcium phosphate cement (CPC), beta-galactosidase (β-GAL), (1,2,3,4,6-pentaacetyl a-D-galactose), cellulose, chitin, chitosan, collagen, elastin, gelatin, hyaluronic acid collagen, hydroxyapatite, poly(3-hydroxybutyrate-co-3-hydroxy-hexanoate) (PH BH Hx), poly(lactide), poly(caprolactone) (PCL), poly(lactide-co-glycolide) (PLG), poly(lactic-co-glycolic acid) (PLGA), poly(vinyl alcohol) (PVA), silk, soy protein, and soy protein isolate, alone or in combination with any other polymer composition, in any concentration and in any ratio. Blending different polymer types in different ratios using various grades can result in characteristics that borrow from each of the contributing polymers. Various terminal group chemistries can also be adopted. Exemplary metals, transition metals and metalloids include lithium, magnesium, zinc, aluminum and silica. In particular embodiments, the porous particles include silica. The exceptionally high surface area of mesoporous silica (exceeding 1,000 m2/g) enables STING agonist loading at levels exceeding conventional carriers such as liposomes or polymer conjugates. In additional embodiments, pores range in size from 10-20 nm.

Useful particles of particular embodiments also include those based on lipid-based delivery systems, including cationic lipids, ionizable cationic lipids, lipid-like molecules and pH-sensitive amphiphiles; and/or (ii) dendrimers (highly branched, spherical macromolecules synthesized from poly-amidoamine (PAMAM) and poly-propylene iminie (PPI), and block copolymers such as PAA/BMA/DMAEMA and PDMAEMA.

The particles can be a variety of different shapes, including spheroidal, cuboidal, pyramidal, oblong, cylindrical, toroidal, and the like. The components can be included in the porous nanoparticles in a variety of ways. For example, the components can be encapsulated in the porous particles. In other aspects, the components can be associated (e.g., covalently and/or non-covalently) with the surface or close underlying vicinity of the surface of the particles. In particular embodiments, the components can be incorporated in the particles e.g., integrated in the material of the particles. For example, the components can be incorporated into a polymer matrix of polymer particles. One of ordinary skill in the art will appreciate the various ways to carry the components within an implantable scaffold as described herein.

In particular embodiments, particles include liposomes. Liposomes are microscopic vesicles including at least one concentric lipid bilayer. Vesicle-forming lipids are selected to achieve a specified degree of fluidity or rigidity of the final complex. In particular embodiments, liposomes provide a lipid composition that is an outer layer surrounding a particle.

Liposomes can be neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including dioleoylphosphatidylethanolamine (DOPE), with a hydrocarbon chain length in the range of 14-22, and saturated or with one or more double C═C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioleoylphosphatidylglycerol (DOPG), dicetylphosphate that are able to form vesicles. In particular embodiments, lipids used to create liposomes disclosed herein include cholesterol, hydrogenated soy phosphatidylcholine (HSPC) and, the derivatized vesicle-forming lipid PEG-DSPE.

Methods of forming liposomes are described in, for example, U.S. Pat. Nos. 4,229,360; 4,224,179; 4,241,046; 4,737,323; 4,078,052; 4,235,871; 4,501,728; and 4,837,028, as well as in Szoka et al., Ann. Rev. Biophys. Bioeng. 9:467 (1980) and Hope et al., Chem. Phys. Lip. 40:89 (1986).

The size of the particles can vary over a wide range and can be measured in different ways. For example, particles of the present disclosure can have a minimum dimension of 100 nm. The particles of the present disclosure can also have a minimum dimension of equal to or less than 500 nm, less than 150 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, the particles can have a minimum dimension ranging between 5 nm and 500 nm, between 10 nm and 100 nm, between 20 nm and 90 nm, between 30 nm and 80 nm, between 40 nm and 70 nm, and between 40 nm and 60 nm. In particular embodiments, the dimension is the diameter of the particles. In particular embodiments, a population of particles can have a mean minimum dimension of equal to or less than 500 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, a population of particles in an implantable scaffold can have a mean diameter ranging between 5 nm and 500 nm, between 10 nm and 100 nm, between 20 nm and 90 nm, between 30 nm and 80 nm, between 40 nm and 70 nm, and between 40 nm and 60 nm. Dimensions of the particles can be determined using, e.g., conventional techniques, such as dynamic light scattering and/or electron microscopy.

In particular embodiments, the scaffolds include protocells as particles. Protocells can be formed via fusion of liposomes to porous silica nanoparticles. The high pore volume and surface area of the spherical mesoporous silica core allow high-capacity encapsulation of a spectrum of cargos, including components. The supported lipid bilayer, whose composition can be modified for specific biological applications, can serve as a modular, reconfigurable scaffold, allowing the attachment of a variety of functional molecules, such as the components described elsewhere herein.

When desired, release of various materials from particles can be modified by incorporation of surfactants, detergents, complexing agents, internal phase viscosity enhancers, surface active molecules, co-solvents, chelators, stabilizers, derivatives of cellulose, polysorbates, PVA or sucrose. Salts and buffers can also be used to alter release characteristics.

Figure 12A:
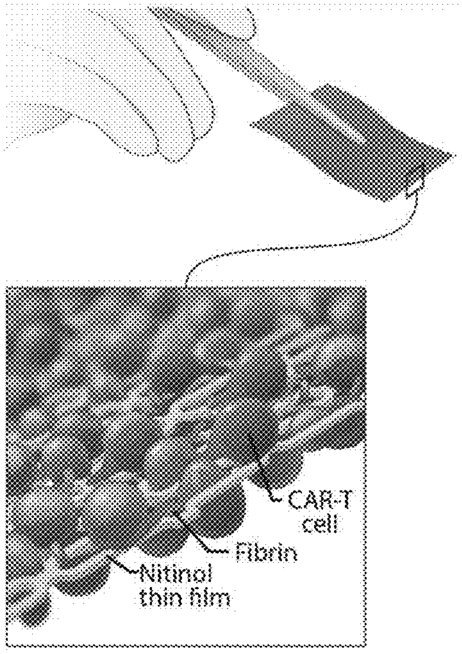
FIGS. 12A-12I. Sustained release of T cells from bioactive TFN micromeshes. (12A, 12B) Schematics of a single-layer TFN micromesh (FIG. 12A) or stent (FIG. 12B) functionalized with anti-CD3/CD28/CD137 antibody-functionalized fibrin and tumor-reactive CAR T cells.
Figure 12B:
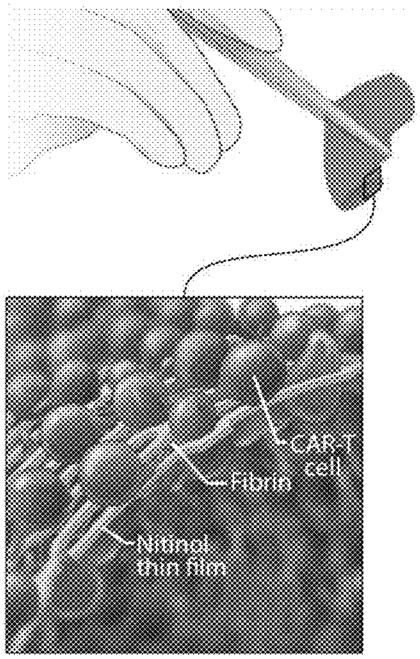
Figure 12C:
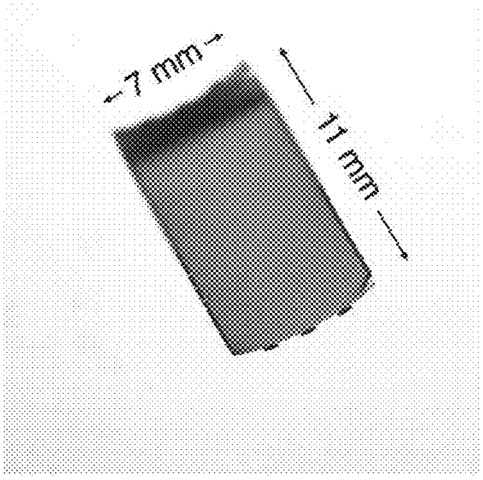
Figure 12D:
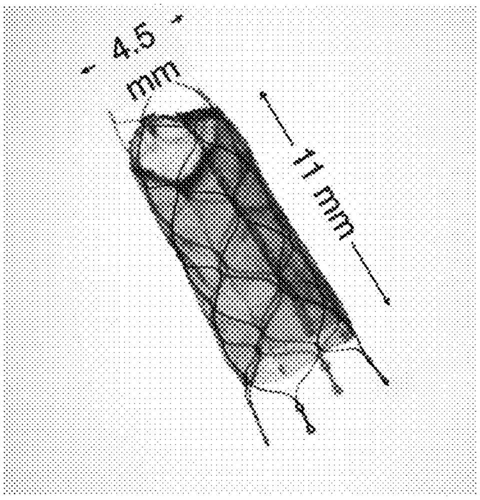
Figure 12E:
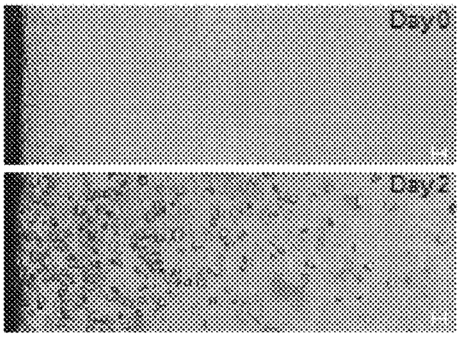
Figure 12F:
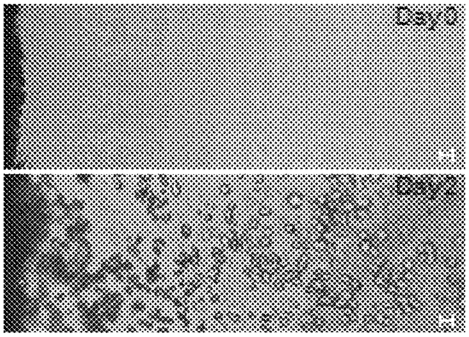
Figure 12G:
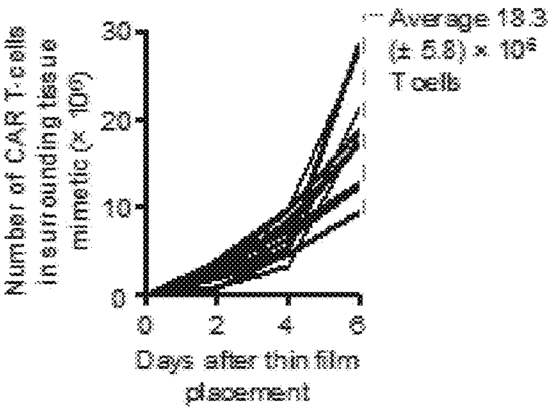
Figure 12H:
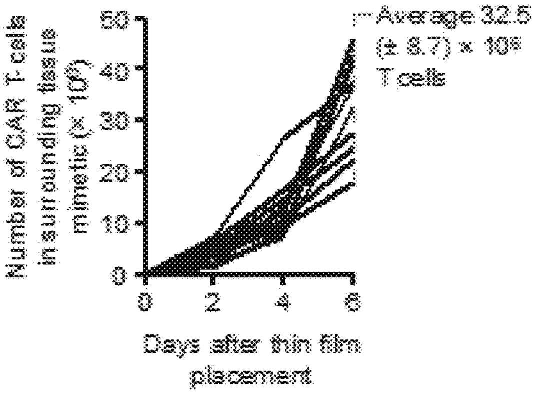

In particular embodiments a lymphocyte scaffold including a TFN micromesh can be coated on a medical device. TFN is unique among cell scaffolds in that it can be easily incorporated into a minimally-invasive medical device, such as a stent or another cylindrical-shaped device. Minimally invasive medical device can refer to a medical device that can be placed/implanted using a minimally invasive procedure. A minimally invasive procedure can be a procedure that requires only a very small incision (e.g., less than 1 cm or less than 2 cm), and/or is associated with shortened wound healing time, associated pain or risk of infection, as compared to procedures that require larger incisions. An example of a stent covered with a TFN micromesh is shown in FIG. 12D. This unique device facilitates delivery of anti-cancer lymphocytes directly to the site of a solid tumor without the need for open surgery.

Genetically Reprogrammed Lymphocytes. The structures of the scaffolds disclosed herein include embedded lymphocytes. Any type of lymphocyte capable of targeting and killing tumor cells, targeting tumor cells for killing by other cell types, or otherwise mediating tumor cell killing can be used. The lymphocytes can be autologous to the individual to whom the scaffold is administered.

Lymphocytes include T-cells, B cells and natural killer (NK) cells. The current disclosure focuses on the use of embedded T-cells and/or NK cells, but other types of lymphocytes may be used as well, alone or in combination.

Several different subsets of T-cells have been discovered, each with a distinct function. T-cells include helper cells (CD4+ T-cells) and cytotoxic T-cells (CTLs, CD8+ T-cells) which include cytolytic T-cells.

T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T-cells destroy virally infected cells and tumor cells, and are also implicated in transplant rejection. These cells are also known as CD8+ T-cells because they express the CD8 glycoprotein at their surface. These cells recognize their targets by binding to antigen associated with MHC class I, which is present on the surface of nearly every cell of the body.

A majority of T-cells have a T-cell receptor (TCR) existing as a complex of several proteins. The actual TCR is composed of two separate peptide chains, which are produced from the independent T-cell receptor alpha and beta (TCRα and TCRβ) genes and are called α- and β-TCR chains. Gamma-delta (γΔ) T-cells represent a small subset of T-cells that possess a distinct TCR on their surface. However, in γΔ T-cells, the TCR is made up of one γ-chain and one Δ-chain. This group of T-cells is much less common (2% of total T-cells) than the αβ T-cells.

"Central memory" T-cells (or "$T_{CM}$"), as used herein, refers to an antigen experienced CTL that expresses CD62L or CCR-7 and CD45RO on the surface thereof, and does not express or has decreased expression of CD45RA as compared to naive cells. In particular embodiments, central memory cells are positive for expression of CD62L, CCR7, CD2S, CD127, CD45RO, and CD95, and have decreased expression of CD54RA as compared to naive cells.

"Effector memory" T-cell (or "$T_{EM}$"), as used herein, refers to an antigen experienced T-cell that does not express or has decreased expression of CD62L on the surface thereof as compared to central memory cells, and does not express or has decreased expression of CD45RA as compared to a naive cell. In particular embodiments, effector memory cells are negative for expression of CD62L and CCR7, compared to naive cells or central memory cells, and have variable expression of CD28 and CD45RA.

"Naive" T-cells, as used herein, refers to a non-antigen experienced T lymphocyte that expresses CD62L and CD45RA, and does not express CD45RO as compared to central or effector memory cells. In particular embodiments, naive CD8+ T lymphocytes are characterized by the expression of phenotypic markers of naive T-cells including CD62L, CCR7, CD28, CD127, and CD45RA.

"Effector" or "TE" T-cells, as used herein, refers to an antigen experienced cytotoxic T lymphocyte cells that do not express or have decreased expression of CD62L, CCR7, CD28, and are positive for granzyme B and perforin as compared to central memory or naive T-cells.

NK cells are cytotoxic lymphocytes that can rapidly respond to viral infection or tumor formation. NK cells can recognize "stressed" cells in the absence of MHC expression or antibodies, and can release cytolytic granules containing proteins such as perforin, which may form pores in cell membranes of nearby cells. NK cells can become activated in the presence of cytokines including IL-12, IL-15, IL-18, IL-2, and CCL5. NK cells may become activated upon ligand binding to an NK cell activating receptor. Receptors that can contribute to NK cell activation include CD137, CD2, and CD44.

Each of the lymphocyte types described herein can be embedded in the scaffolds disclosed herein. In particular embodiments, the primary lymphocyte cell type will be CTL. CTLs can be included at 50% or more of the embedded lymphocyte population, 55% or more of the embedded lymphocyte population, 60% or more of the embedded lymphocyte population, 65% or more of the embedded lymphocyte population, 70% or more of the embedded lymphocyte population, 75% or more of the embedded lymphocyte population, 80% or more of the embedded lymphocyte population, 85% or more of the embedded lymphocyte population, 90% or more of the embedded lymphocyte population, 95% or more of the embedded lymphocyte population, or 100% the embedded lymphocyte population.

Various combinations of lymphocytes can also be used in the scaffolds disclosed herein. In particular embodiments, the scaffold includes a mixture of CD8+ cells, NK cells, invariant NKT cells (iNKT cells), Th17 CD4+ cells and/or B cells. In particular embodiments, the scaffolds include a mixture of CD8+ cells and NK cells. In particular embodiments, the mixture of CD8+ cells and NK cells is a 50:50 mix. In particular embodiments, the scaffolds include a mixture of CD8+ cells and iNKT cells. In particular embodiments, the mixture of CD8+ cells and iNKT cells is a 50:50 mix. All other possible combinations of the disclosed cell types can also be used within the scaffolds disclosed herein.

In particular embodiments, the lymphocytes can be isolated and expanded from resected tumor. In particular embodiments, subjects can be vaccinated with a tumor antigen (e.g., against Her2) and vaccine-induced T-cell populations can be expanded and embedded into the scaffold.

Lymphocytes within the scaffolds can be non-genetically modified or genetically-modified or can be provided in a combination of non-genetically-modified and genetically-modified forms. Genetic modifications can be made to enhance growth, survival, immune function and/or tumor cell targeting. Examples of genetic modifications include those allowing expression of: a chimeric antigen receptor (CAR), a αβ T-cell receptor (or modification thereof), and/or pro-inflammatory cytokines; or blocking expression of an inhibitor signal (e.g., killer-cell immunoglobulin-like receptor). CAR modification and/or αβ T-cell receptor modifications allow the modified lymphocytes to specifically target cell types.

In one aspect, genetically-modified lymphocytes can have improved tumor recognition, trigger increased native T-cell proliferation and/or cytokine production. Different potential CAR nucleic acid constructs that encode different ligand binding domains, different spacer region lengths, different intracellular binding domains and/or different transmembrane domains, can be tested in vivo (in an animal model) and/or in vitro to identify CARs with improved function over non-genetically modified lymphocytes and/or other CARs and in particular embodiments, using the scaffolds disclosed herein as an in vivo screening tool.

Exemplary CARs express ligand binding domains targeting, for example, NKG2D ligands, mesothelin, Her2, WT-1 and/or EGRF. An exemplary T-cell receptor modification targets melanoma-associated antigen (MAGE) A3 TCR.

The particular following cancers can be targeted by including within an extracellular component of a TCR or CAR a binding domain that binds the associated cellular marker(s):

| Targeted Cancer | Cellular Marker(s) |
|---|---|
| Prostate Cancer | PSMA, WT1, Prostate Stem Cell antigen (PSCA), SV40 T |
| Breast Cancer | HER2, ERBB2, ROR1 |
| Stem Cell Cancer | CD133 |
| Ovarian Cancer | L1-CAM, extracellular domain of MUC16 (MUC-CD), folate binding protein (folate receptor), Lewis Y, ROR1, mesothelin, WT-1 |
| Mesothelioma | mesothelin |
| Renal Cell Carcinoma | carboxy-anhydrase-IX (CAIX); |
| Melanoma | GD2 |
| Pancreatic Cancer | mesothelin, CEA, CD24, ROR1, NKG2D ligands (e.g., Rae-1) |
| Lung Cancer | ROR1 |

Without limiting the foregoing, cellular markers also include A33; BAGE; Bcl-2; β-catenin; B7H4; BTLA; CA125; CA19-9; CD3, CD5; CD19; CD20; CD21; CD22; CD25; CD28; CD30; CD33; CD37; CD40; CD52; CD44v6; CD45; CD56; CD79b; CD80; CD81; CD86; CD123; CD134; CD137; CD151; CD171; CD276; CEA; CEACAM6; c-Met; CS-1; CTLA-4; cyclin B1; DAGE; EBNA; EGFR; EGFRvIII, ephrinB2; ErbB2; ErbB3; ErbB4; EphA2; estrogen receptor; FAP; ferritin; α-fetoprotein (AFP); FLT1; FLT4; folate-binding protein; Frizzled; GAGE; G250; GD-2; GHRHR; GHR; GITR; GM2; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFIRβ; LRP; LRP5; LTβR; MAGE; MART; mesothelin; MUC; MUC1; MUM-1-B; myc; NYESO-1; O-acetyl GD-2; O-acetyl GD3; OSMRβ; p53; PD1; PD-L1; PD-L2; PRAME; progesterone receptor; PSA; PSMA; PTCH1; RANK; ras; Robo1; RORI; survivin; TCRα; TCRβ; tenascin; TGFBR1; TGFBR2; TLR7; TLR9; TNFR1; TNFR2; TNFRSF4; TWEAK-R; TSTA tyrosinase; VEGF; and WT1.

Particular cancer cell cellular markers include:

| Cancer Antigen | Sequence | SEQ ID NO: |
|---|---|---|
| PSMA | MWNLLHETDSAVATARRPRWLCAGALVLAGGFFLLGFLFGWFIKS<br>SNEATNITPKHNMKAFLDELKAENIKKFLYNFTQIPHLAGTEQNFQL<br>AKQIQSQWKEFGLDSVELAHYDVLLSYPNKTHPNYISIINEDGNEIF<br>NTSLFEPPPPGYENVSDIVPPFSAFSPQGMPEGDLVYVNYARTED<br>FFKLERDMKINCSGKIVIARYGKVFRGNKVKNAQLAGAKGVILYSD<br>PADYFAPGVKSYPDGWNLPGGGVQRGNILNLNGAGDPLTPGYPA<br>NEYAYRRGIAEAVGLPSIPVHPIGYYDAQKLLEKMGGSAPPDSSW | 6 |

-continued

| Cancer Antigen | Sequence | SEQ ID NO: |
|---|---|---|
| | RGSLKVPYNVGPGFTGNFSTQKVKMHIHSTNEVTRIYNVIGTLRGA VEPDRYVILGGHRDSWVFGGIDPQSGAAVVHEIVRSFGTLKKEGW RPRRTILFASWDAEEFGLLGSTEWAEENSRLLQERGVAYINADSSI EGNYTLRVDCTPLMYSLVHNLTKELKSPDEGFEGKSLYESWTKKS PSPEFSGMPRISKLGSGNDFEVFFQRLGIASGRARYTKNWETNKF SGYPLYHSVYETYELVEKFYDPMFKYHLTVAQVRGGMVFELANSI VLPFDCRDYAVVLRKYADKIYSISMKHPQEMKTYSVSFDSLFSAVK NFTEIASKFSERLQDFDKSNPIVLRMMNDQLMFLERAFIDPLGLPD RPFYRHVIYAPSSHNKYAGESFPGIYDALFDIESKVDPSKAWGEVK RQIYVAAFTVQAAAETLSEVA | |
| PSCA | MKAVLLALLMAGLALQPGTALLCYSCKAQVSNEDCLQVENCTQLG EQCWTARIRAVGLLTVISKGCSLNCVDDSQDYYVGKKNITCCDTD LCNASGAHALQPAAAILALLPALGLLLWGPGQL | 7 |
| Mesothelin | MALPTARPLLGSCGTPALGSLLFLLFSLGWVQPSRTLAGETGQEA APLDGVLANPPNISSLSPRQLLGFPCAEVSGLSTERVRELAVALAQ KNVKLSTEQLRCLAHRLSEPPEDLDALPLDLLLFLNPDAFSGPQAC THFFSRITKANVDLLPRGAPERQRLLPAALACWGVRGSLLSEADV RALGGLACDLPGRFVAESAEVLLPRLVSCPGPLDQDQQEAARAAL QGGGPPYGPPSTWSVSTMDALRGLLPVLGQPIIRSIPQGIVAAWR QRSSRDPSWRQPERTILRPRFRREVEKTACPSGKKAREIDESLIFY KKWELEACVDAALLATQMDRVNAIPFTYEQLDVLKHKLDELYPQG YPESVIQHLGYLFLKMSPEDIRKWNVTSLETLKALLEVNKGHEMSP QVATLIDRFVKGRGQLDKDTLDTLTAFYPGYLCSLSPEELSSVPPS SIWAVRPQDLDTCDPRQLDVLYPKARLAFQNMNGSEYFVKIQSFL GGAPTEDLKALSQQNVSMDLATFMKLRTDAVLPLTVAEVQKLLGP HVEGLKAEERHRPVRDWILRQRQDDLDTLGLGLQGGIPNGYLVLD LSVQEALSGTPCLLGPGPVLTVLALLLASTLA | 8 |
| CD19 | MPPPRLLFFLLFLTPMEVRPEEPLVVKVEEGDNAVLQCLKGTSDG PTQQLTWSRESPLKPFLKLSLGLPGLGIHMRPLASWLFIFNVSQQ MGGFYLCQPGPPSEKAWQPGVVTVNVEGSGELFRWNVSDLGGL GCGLKNRSSEGPSSPSGKLMSPKLYVWAKDRPEIWEGEPPCVPP RDSLNQSLSQDLTMAPGSTLWLSCGVPPDSVSRGPLSWTHVHPK GPKSLLSLELKDDRPARDMWVMETGLLLPRATAQDAGKYYCHRG NLTMSFHLEITARPVLWHWLLRTGGWKVSAVTLAYLIFCLCSLVG1 LHLQRALVLRRKRKRMTDPTRRFFKVTPPPGSGPQNQYGNVLSL PTPTSGLGRAQRWAAGLGGTAPSYGNPSSDVQADGALGSRSPP GVGPEEEEGEGYEEPDSEEDSEFYENDSNLGQDQLSQDGSGYE NPEDEPLGPEDEDSFSNAESYENEDEELTQPVARTMDFLSPHGS AWDPSREATSLGSQSYEDMRGILYAAPQLRSIRGQPGPNHEEDA DSYENMDNPDGPDPAWGGGGRMGTWSTR | 9 |
| CD20 | MTTPRNSVNGTFPAEPMKGPIAMQSGPKPLFRRMSSLVGPTQSF FMRESKTLGAVQIMNGLFHIALGGLLMIPAGIYAPICVTVWYPLWG GIMYIISGSLLAATEKNSRKCLVKGKMIMNSLSLFAAISGMILSIMDIL NIKISHFLKMESLNFIRAHTPYINIYNCEPANPSEKNSPSTQYCYSIQ SLFLGILSVMLIFAFFQELVIAGIVENEWKRTCSRPKSNIVLLSAEEK KEQTIEIKEEVVGLTETSSQPKNEEDIEIIPIQEEEEEETETNFPEPP QDQESSPIENDSSP | 10 |
| ROR1 | MHRPRRRGTRPPLLALLAALLLAARGAAAQETELSVSAELVPTSS WNISSELNKDSYLTLDEPMNNITTSLGQTAELHCKVSGNPPPTIRW FKNDAPVVQEPRRLSFRSTIYGSRLRIRNLDTTDTGYFQCVATNGK EVVSSTGVLFVKFGPPPTASPGYSDEYEEDGFCQPYRGIACARFI GNRTVYMESLHMQGEIENQITAAFTMIGTSSHLSDKCSQFAIPSLC HYAFPYCDETSSVPKPRDLCRDECEILENVLCQTEYIFARSNPMIL MRLKLPNCEDLPQPESPEAANCIRIGIPMADPINKNHKCYNSTGVD YRGTVSVTKSGRQCQPWNSQYPHTHTFTALRFPELNGGHSYCR NPGNQKEAPWCFTLDENFKSDLCDIPACDSKDSKEKNKMEILYILV PSVAIPLAIALLFFFICVCRNNQKSSSAPVQRQPKHVRGQNVEMSM LNAYKPKSKAKELPLSAVRFMEELGECAFGKIYKGHLYLPGMDHA QLVAIKTLKDYNNPQQWTEFQQEASLMAELHHPNIVCLLGAVTQE QPVCMLFEYINQGDLHEFLIMRSPHSDVGCSSDEDGTVKSSLDHG DFLHIAIQIAAGMEYLSSHFFVHKDLAARNILIGEQLHVKISDLGLSR ElYSADYYRVQSKSLLPIRWMPPEAIMYGKFSSDSDIWSFGVVLW EIFSFGLQPYYGFSNQEVIEMVRKRQLLPCSEDCPPRMYSLMTEC WNEIPSRRPRFKDIHVRLRSWEGLSSHTSSTTPSGGNATTQTTSL SASPVSNLSNPRYPNYMFPSQGITPQGQIAGFIGPPIPQNQRFIPIN GYPIPPGYAAFPAAHYQPTGPPRVIQHCPPPKSRSPSSASGSTST GHVTSLPSSGSNQEANIPLLPHMSIPNHPGGMGITVFGNKSQKPY KIDSKQASLLGDANIHGHTESMISAEL | 11 |
| WT1 | MGHHHHHHHHHHSSGHIEGRHMRRVPGVAPTLVRSASETSEKR PFMCAYPGCNKRYFKLSHLQMHSRKHTGEKPYQCDFKDCERRFF | 12 |

-continued

| Cancer Antigen | Sequence | SEQ ID NO: |
|---|---|---|
| | RSDQLKRHQRRHTGVKPFQCKTCQRKFSRSDHLKTHTRTHTGEK PFSCRWPSCQKKFARSDELVRHHNMHQRNMTKLQLAL | |

In particular embodiments, ROR1-specific and CD19-specific CARs can be constructed using VL and VH chain segments of the 2A2, R12, and R11 mAhs (ROR1) and FMC63 mAb (CD19). Variable region sequences for R11 and R12 are provided in Yang et al, Plos One 6(6):e21018, Jun. 15, 2011. Each scFV can be linked by a $(Gly_4Ser)_3$ (SEQ ID NO: 13) protein to a spacer domain derived from IgG4-Fc (UniProt Database: P01861, SEQ ID NO: 14) including either 'Hinge-CH2-CH3' (229 AA, SEQ ID NO: 15), 'Hinge-CH3' (119 AA, SEQ ID NO: 16) or 'Hinge' only (12 AA, SEQ ID NO: 17) sequences. All spacers can contain a S→P substitution within the 'Hinge' domain located at position 108 of the native IgG4-Fc protein, and can be linked to the 27 AA transmembrane domain of human CD28 (SEQ ID NO: 18, for an exemplary full-length CD28 see UniProt: P10747) and to an effector domain signaling module including either (i) the 41 AA cytoplasmic domain of human CD28 with an LL→GG substitution located at positions 186-187 of the native CD28 protein (SEQ ID NO: 19) or (ii) the 42 AA cytoplasmic domain of human 4-1BB (UniProt: Q07011, SEQ ID NO: 20), each of which can be linked to the 112 AA cytoplasmic domain of isoform 3 of human CD3ζ (UniProt: P20963, SEQ ID NO: 21). The construct encodes a T2A ribosomal skip element (SEQ ID NO: 22)) and a tEGFR sequence (SEQ ID NO: 23) downstream of the chimeric receptor. tEGFR can be replaced or supplemented with a tag cassette binding a sequence, such as STREP-TAG® II (SEQ ID NO: 24; IBA GMBH Ltd., Gottingen, DE), Myc tag (SEQ ID NO: 25), V5 tag (SEQ ID NO: 26), FLAG® (Sigma-Aldrich, St. Louis, MO) tag (SEQ ID NO: 27), His tag, or other peptides or molecules as disclosed herein. Codon-optimized gene sequences encoding each transgene can be synthesized (Life Technologies) and cloned into the epHIV7 lentiviral vector using NheI and Not1 restriction sites. The epHIV7 lentiviral vector can be derived from the pHIV7 vector by replacing the cytomegalovirus promoter of pHIV7 with an EF-1 promoter. ROR1-chimeric receptor, CD19-chimeric receptor, tEGFR, or tag cassette-encoding lentiviruses can be produced in 293T cells using the packaging vectors pCHGP-2, pCMV-Rev2 and pCMV-G, and Calphos™ calcium phosphate transfection reagent (Clontech).

HER2-specific chimeric receptors can be constructed using VL and VH chain segments of a HER2-specific mAb that recognizes a membrane proximal epitope on HER2, and the scFVs can be linked to IgG4 hinge/CH2/CH3, IgG4 hinge/CH3, and IgG4 hinge only extracellular spacer domains and to the CD28 transmembrane domain, 4-1BB and CD3ζ signaling domains.

As indicated, each CD19 chimeric receptor can include a single chain variable fragment corresponding to the sequence of the CD19-specific mAb FMC63 (scFv: VL-VH), a spacer derived from IgG4-Fc including either the 'Hinge-CH2-CH3' domain (229 AA, long spacer) or the 'Hinge' domain only (12 AA, short spacer), and a signaling module of CD3ζ with membrane proximal CD28 or 4-1BB costimulatory domains, either alone or in tandem. The transgene cassette can include a truncated EGFR (tEGFR) downstream from the chimeric receptor gene and be separated by a cleavable T2A element, to serve as a tag sequence for transduction, selection and in vivo tracking for chimeric receptor-modified cells. tEGFR can be replaced or supplemented with a tag cassette binding a ExoCBM, such as STREP-TAG® II (SEQ ID NO: 24), Myc tag (SEQ ID NO: 25), V5 tag (SEQ ID NO: 26), FLAG® tag (SEQ ID NO: 27), His tag, or other peptides or molecules as disclosed herein.

Other common features of engineered CARs such as spacers, intracellular domains, costimulatory domains, and transmembrane domains are known to those of skill in the art.

In particular embodiments it may be desired to introduce functional genes into the lymphocytes to allow for negative selection in vivo as described by, for example, Lupton et al., Mol. and Cell Biol., 11:6 (1991); and Riddell et al., Human Gene Therapy 3:319-338 (1992); see also the publications PCT/US91/08442 and PCT/US94/05601 by Lupton et. al. describing the use of bifunctional selectable fusion genes derived from fusing a dominant positive selectable marker with a negative selectable marker. This can be carried out in accordance with known techniques (see, e.g., U.S. Pat. No. 6,040,177 at columns 14-17) or variations thereof that will be apparent to those skilled in the art based upon the present disclosure. For example, it is contemplated that overexpression of a stimulatory factor (for example, a lymphokine or a cytokine) may be toxic to the treated subject. Therefore, it is within the scope of the disclosure to include gene segments that cause the cells of the disclosure to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene, which confers ganciclovir sensitivity; the cellular hypoxanthine phosphribosyltransferase (HPRT) gene, the cellular adenine phosphoribosyltransferase (APRT) gene, and bacterial cytosine deaminase.

Desired genes can be introduced into the lymphocytes prior to embedding in a scaffold disclosed herein. Genetic reprogramming of a cell can include, for example, insertion of a gene sequence, alteration of a gene sequence, and/or deletion of a gene sequence. In particular embodiments, lymphocytes can be genetically-reprogrammed by introducing a vector for genetic reprogramming into the lymphocytes. Particular embodiments can deliver nucleotides within a gene editing system. Gene editing systems modify or affect particular sequences of a cell's endogenous genome. Gene editing systems are useful for targeted genome editing, for example gene disruption, gene editing by homologous recombination, and gene therapy to insert therapeutic genes at the appropriate chromosomal target sites with a human genome.

Particular embodiments utilize transcription activator-like effector nucleases (TALENs) as gene editing systems. TALENs refer to fusion proteins including a transcription activator-like effector (TALE) DNA binding protein and a DNA cleavage domain. TALENs are used to edit genes and genomes by inducing double strand breaks (DSBs) in the DNA, which induce repair mechanisms in cells. Generally, two TALENs must bind and flank each side of the target DNA site for the DNA cleavage domain to dimerize and induce a DSB. The DSB is repaired in the cell by non-homologous end-joining (NHEJ) or by homologous recombination (HR) with an exogenous double-stranded donor DNA fragment.

As indicated, TALENs have been engineered to bind a target sequence of, for example, an endogenous genome, and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the 12th and 13th positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. The FokI domain functions as a dimer requiring two constructs with unique DNA binding domains for sites on the target sequence. The FokI cleavage domain cleaves within a five or six base pair spacer sequence separating the two inverted half-sites.

Particular embodiments utilize MegaTALs as gene editing systems. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Particular embodiments utilize zinc finger nucleases (ZFNs) as gene editing systems. ZFNs are a class of site-specific nucleases engineered to bind and cleave DNA at specific positions. ZFNs are used to introduce DSBs at a specific site in a DNA sequence which enables the ZFNs to target unique sequences within a genome in a variety of different cells. Moreover, subsequent to double-stranded breakage, homologous recombination or non-homologous end joining takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease.

Guide RNA can be used, for example, with gene-editing systems such as CRISPR-Cas systems. CRISPR-Cas systems include CRISPR repeats and a set of CRISPR-associated genes (Cas).

In general, any system capable of resulting in functional expression of delivered nucleotides can be used within the current disclosure.

Introduction of genes can be carried out by any method known in the art, including transfection, electroporation, microinjection, lipofection, calcium phosphate mediated transfection, infection with a viral or bacteriophage vector (e.g., a lentiviral vector or plasmid) containing the gene sequences, cell fusion, chromosome-mediated gene transfer, microcell-mediated gene transfer, sheroplast fusion, etc. Numerous techniques are known in the art for the introduction of foreign genes into cells (see e.g., Loeffler and Behr, Meth. Enzymol, 217, 599-618 (1993); Cohen et al., Meth. Enzymol, 217, 618-644 (1993); Cline, Pharmac. Ther, 29, 69-92 (1985)) and may be used in accordance with the present disclosure, provided that the necessary developmental and physiological functions of the lymphocytes are not disrupted. In particular embodiments, the technique provides for the stable transfer of the gene to the cell, so that the gene is expressible by the cell and preferably heritable and expressible by its cell progeny. In particular embodiments, the technique provides for transient expression of the gene within a cell.

Methods commonly known in the art of recombinant DNA technology which can be used to genetically modify the lymphocytes are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In particular embodiments, lymphocytes will be embedded within the scaffolds at or near the time of scaffold implantation in a subject, for example within 48 hours of implantation, within 36 hours of implantation, within 24 hours of implantation, within 12 hours of implantation, within 6 hours of implantation, within 3 hours of implantation, within 1 hour of implantation or within 30 minutes of implantation. Generally, lymphocyte loading into pre-molded scaffolds will occur within 30 minutes of implantation whereas the loading will more often occur closer (i.e., within 5 minutes; within 2 minutes, within 1 minute or within 30 seconds) to the actual implantation time when injectable forms of the scaffolds are used.

The lymphocytes can be fresh lymphocytes or can be previously cryo-preserved lymphocytes. If previously-cryo-preserved lymphocytes are used, they should be thawed quickly (e.g., in a water bath maintained at 37°-41° C.) and chilled immediately upon thawing. It may be desirable to further treat the lymphocytes in order to prevent cellular clumping upon thawing. To prevent clumping, various procedures can be used, including the addition before and/or after freezing of DNase, low molecular weight dextran and citrate, hydroxyethyl starch, etc. Where necessary due to potential cytotoxicities, cryoprotective agents should be removed. After removal of cryoprotective agents, when necessary, cell count and/or viability testing can be performed.

A variety of methods to embed the lymphocytes into structures disclosed herein can be used ("embedding" is also referred to as "seeding"). For example, passive (static) seeding can be used. In particular embodiments, lymphocytes are resuspended in cell culture medium (e.g., RPMI). This cell suspension is then added dropwise on top of a lyophilized scaffold. In particular embodiments, where static seeding is used, a lymphocyte suspension is seeded onto a structure and afterwards incubated for a certain time in the absence of agitation before being exposed to dynamic culture conditions, for example into a spinner flask that is slowly agitated. In particular embodiments, dynamic seeding can be used. For dynamic seeding the structure and the lymphocyte suspension can be placed together in, e.g., a container and the container is then incubated with gentle agitation for a certain time allowing the lymphocytes to embed themselves within the structure. In additional embodiments, rotational systems (including centrifuges) and/or vacuum systems can be used. In additional embodiments, sheet-based lymphocyte seeding, electrostatic lymphocyte seeding, magnetic lymphocyte seeding, filtration lymphocyte seeding, and/or oscillating perfusion lymphocyte seeding can be used. Various combinations of these methods can also be used. The use of various biological hydrogels is also appropriate. For discussions of the various seeding options, see Li et al., Biotechnol. Prog, 17, 935-944 (2001).; Wendt et al., Biotechnology and Bioengineering, 84, 205-214 (2003); Yang, et al., J. Biomed. Mater. Res, 55, 379-386 (2001); and Sittinger et al., Int. J. Artif. Organs, 20, 57 (1997).

Figure 10D:
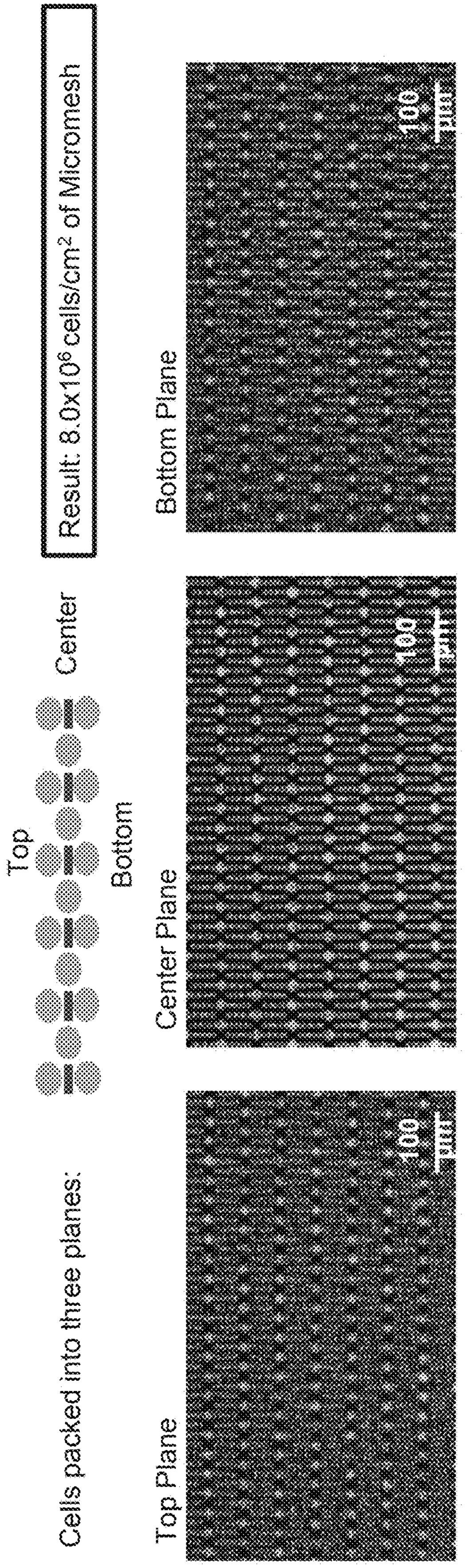
Figure 11A:
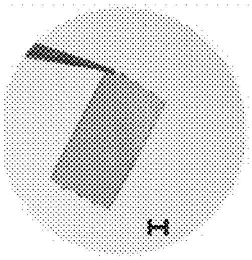
FIGS. 11A-11H. TFN micromeshes functionalized with appropriate lymphocyte-adhesion moieties and stimulatory cues support rapid migration and robust expansion of T cells.
Figure 11B:
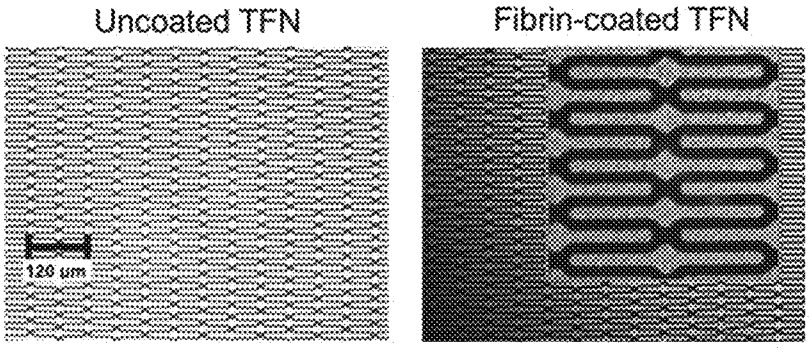
Figure 11C:
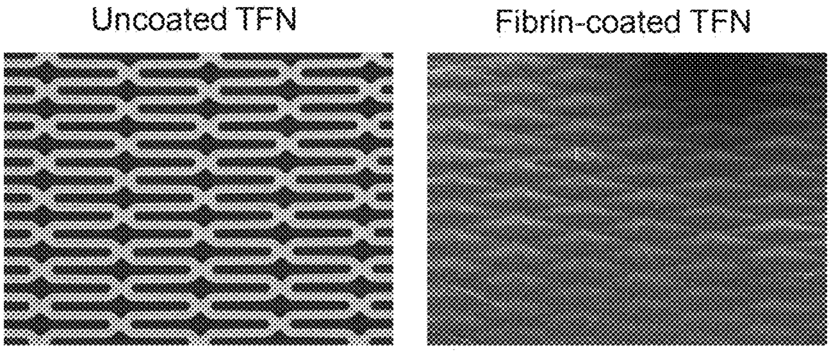
Figure 11D:
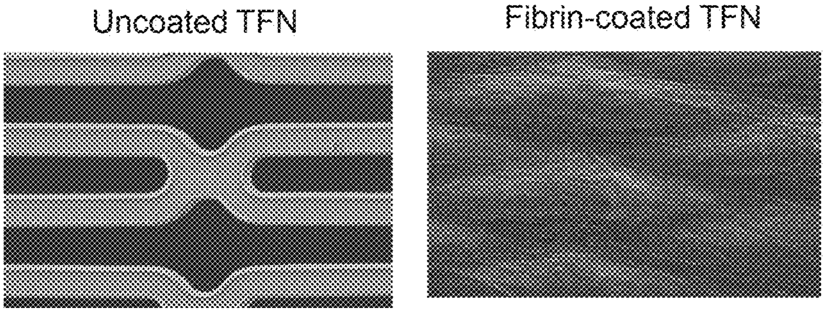
Figure 11E:
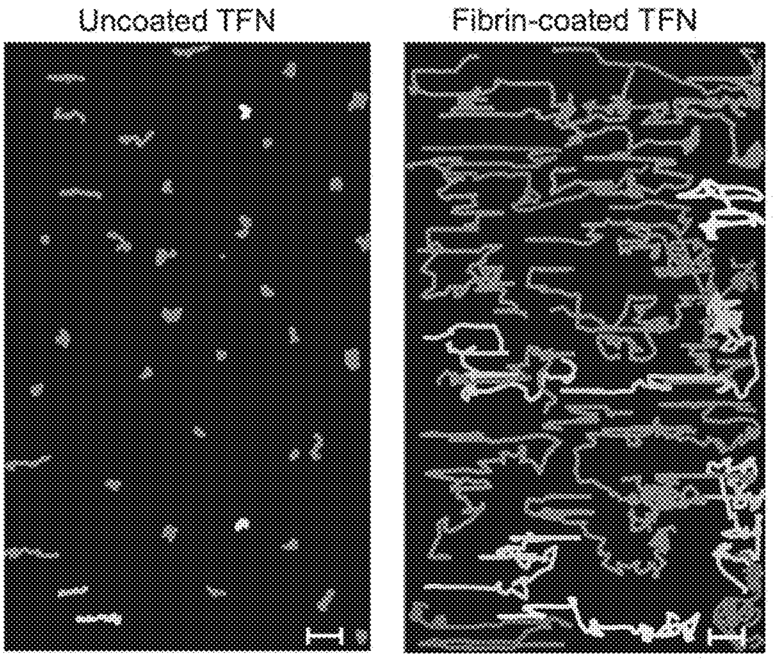
Figure 11F:
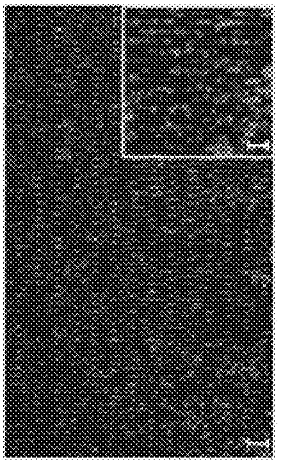
Figure 11G:
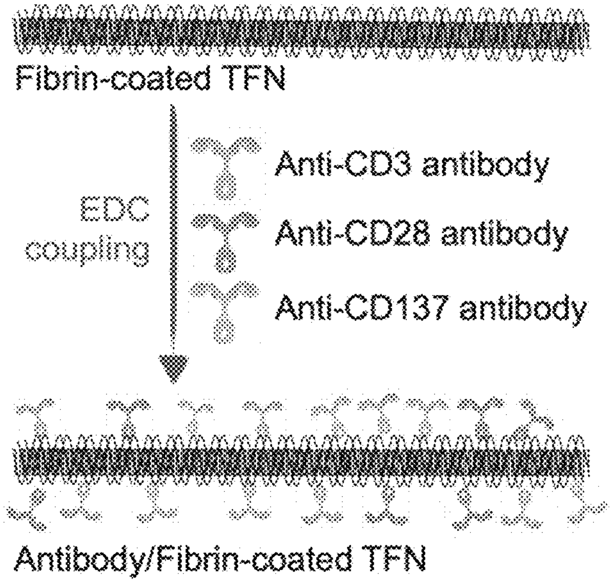
Figure 11H:
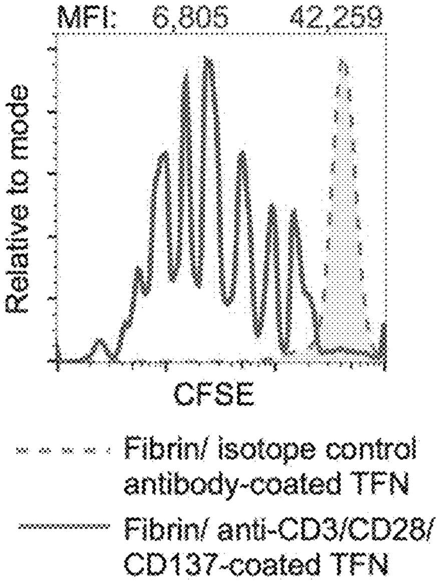

In particular embodiments, a lymphocyte scaffold including a TFN micromesh can include a high-density of cells (at least $7\times10^6$ per $cm^2$ or at least $8\times10^6$ cells per $cm^2$). TFN micromesh can allow for high cell densities, for example, by packing three layers of cells into each layer of TFN micromesh (see, e.g., FIG. 10D). Stacking multiple layers of a micropatterned metallic thin film (e.g., TFN micromesh) can also be useful for achieving high densities of cells.

Effective variants of proteins and protein sequences disclosed herein can also be used. Variants include peptides having one or more conservative amino acid substitutions. As used herein, a "conservative substitution" involves a substitution of one amino acid for another found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gin); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W. H. Freeman and Company.

Variants also include sequences with at least 70% sequence identity, 80% sequence identity, 85% sequence, 90% sequence identity, 95% sequence identity, 96% sequence identity, 97% sequence identity, 98% sequence identity, or 99% sequence identity to any of SEQ ID NOs: 1-27.

"% identity" refers to a relationship between two or more protein sequences, as determined by comparing the sequences. In the art, "identity" also means the degree of sequence relatedness between proteins as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the Lasergene™ bioinformatics computing suite (DNASTAR®, Inc., Madison, WI). Multiple alignment of the sequences can also be performed using the Clustal method of alignment (Higgins and Sharp CABIOS, 5, 151-153 (1989), with default parameters (GAP PENALTY=10, GAP LENGTH PENALTY=10). Relevant programs also include the GCG suite of programs (Wisconsin Package Version 9.0, Genetics Computer Group (GCG), Madison, WI); BLASTP, BLASTN, BLASTX (Altschul, et al., J. Mol. Biol. 215:403-410 (1990)); DNASTAR®; and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y.). Within the context of this disclosure it will be understood that where sequence analysis software is used for analysis, the results of the analysis are based on the "default values" of the program referenced. As used herein "default values" will mean any set of values or parameters which originally load with the software when first initialized.

The current disclosure also provides salts, solvates, hydrates, N-oxides, prodrugs, and/or active metabolites of molecules and/or peptides described herein. Suitable acid addition salts can be prepared from an inorganic acid or an organic acid, in particular pharmaceutically acceptable organic acid. Examples of such inorganic acids include hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable base addition salts can be prepared from a metallic salt or an organic salt. Metallic salts can be prepared from aluminum, calcium, lithium, magnesium, potassium, sodium and zinc. Organic salts can be prepared from N,N'-dibenzylethylene-diamine, chloroprocaine, choline, diethanolamine, ethylenediamine, N-methylglucamine, lysine, arginine, procaine, and any pharmaceutically acceptable organic bases.

Methods of Use. The scaffolds described herein can be placed in the vicinity of a solid tumor, an un-resecatable tumor and/or non-resected tumor cells to have an anti-tumor effect in a subject. As used herein, the terms "subject" or "individual" typically refer to a mammal, such as a human, but can also be another mammal such as dogs, cats, rabbits, cows, horses, etc.

A "tumor" is a swelling or lesion formed by an abnormal growth of cells (called neoplastic cells or tumor cells). A "tumor cell" is an abnormal cell that divides by a rapid, uncontrolled cellular proliferation and continues to divide after the stimuli that initiated the new division cease. Tumors show partial or complete lack of structural organization and functional coordination with the normal tissue, and usually form a distinct mass of tissue, which may be either benign, pre-malignant or malignant.

Figure 9A:
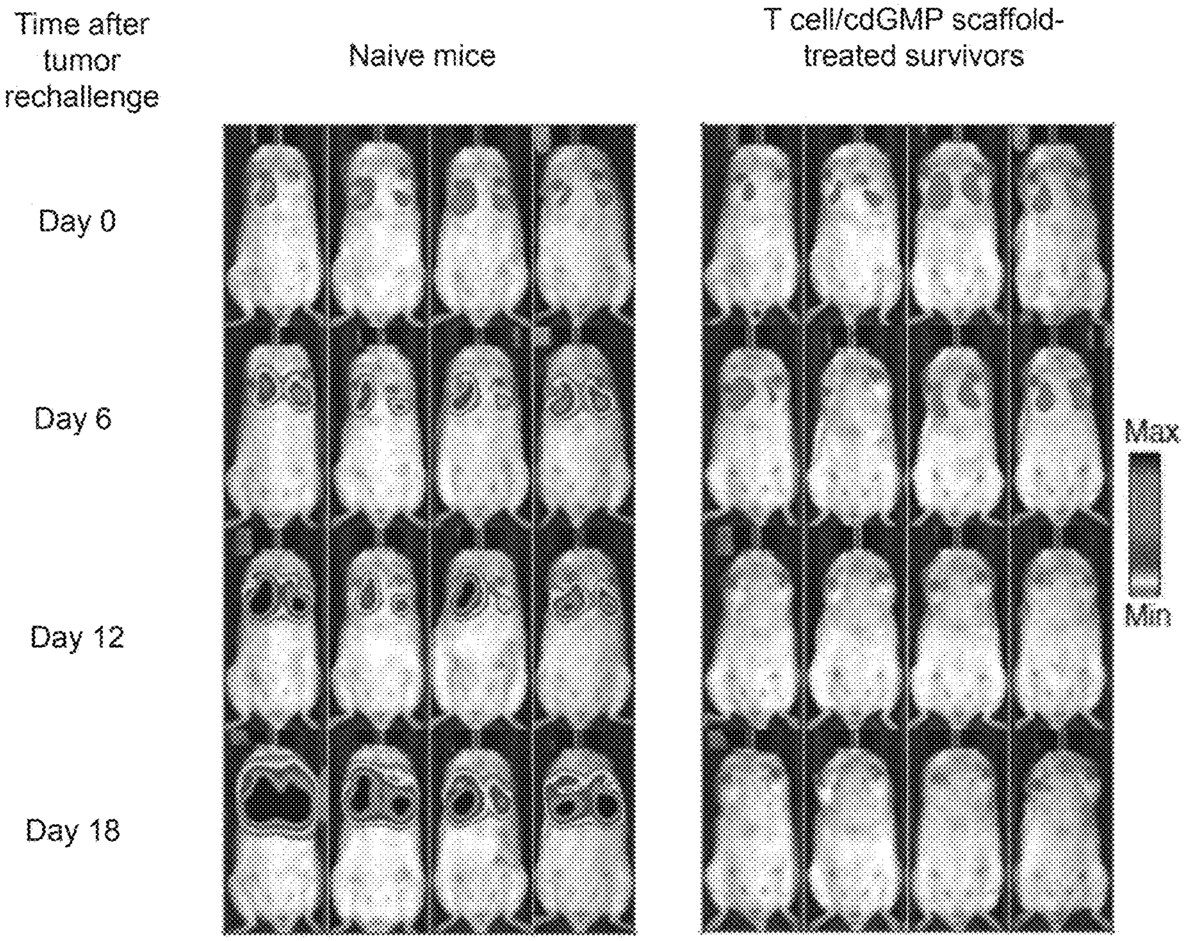
FIGS. 9A, 9B. Scaffolds can elicit global antitumor immunity.
Figure 9B:
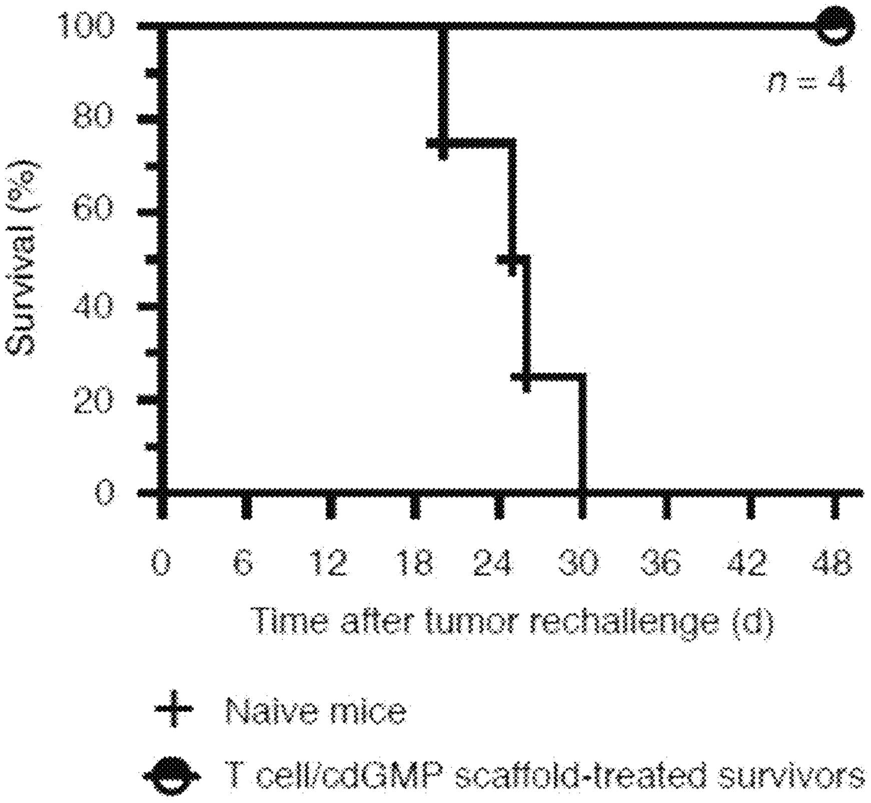

As used herein, an anti-tumor effect refers to a biological effect, which can be manifested by a decrease in tumor volume, a decrease in the number of tumor cells, a decrease in the number of metastases, an increase in life expectancy, or a decrease of various physiological symptoms associated with the cancerous condition. An anti-tumor effect can also be manifested by a decrease in recurrence or an increase in the time before recurrence. Accordingly, the scaffolds disclosed herein can be used to treat a variety of cancers, can prevent or significantly delay metastasis, and/or can prevent or significantly delay relapse. As shown in FIGS. 9A and 9B, lymphocyte scaffolds can continue to provide anti-tumor immunity after eradication/reduction of an initial tumor, and can prevent and/or reduce metastases or development of secondary tumors.

Cancer (medical term: malignant neoplasm) refers to a class of diseases in which a group of cells display uncontrolled growth (division beyond the normal limits), invasion (intrusion on and destruction of adjacent tissues), and sometimes metastasis. "Metastasis" refers to the spread of cancer cells from their original site of proliferation to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential.

Cancers that can be treated with the anti-tumor effects of the scaffolds and methods disclosed herein include, for example, adrenal cancer, brain cancer, breast cancer, cervical cancer, colon cancer, colorectal cancer, ear, nose and throat (ENT) cancer, endometrial cancer, esophageal cancer, gastrointestinal cancer, gliomas, head and neck cancer, intestinal cancer, kidney cancer, liver cancer, lung cancer, lymph node cancer, melanomas, neuroblastomas, ovarian cancer, pancreatic cancer, prostate cancer, rectal cancer, seminomas, skin cancer, stomach cancer, teratomas, thyroid cancer, uterine cancer, and metastases thereof.

Without limiting the scope of the disclosure, the following cancer types are noted:

Brain tumor (Glioblastoma): An estimated 10,000 new cases/year in the U.S. are seen. Currently no curative therapy is available. Gliobastoma shows very infiltrative growth and cannot be resected completely. 90% of tumors relapse within a 2 cm margin from the originally resected tumor. Biomaterial wafers loaded with chemotherapy are United States Food and Drug Administration (FDA)-approved (GLIADEL®, MGI Pharma, Inc., Woodcliff Lake, NJ) for glioblastoma. However, due to insufficient tissue penetration, biomaterial implant delivered chemotherapy is mostly ineffective. In contrast, tumor-reactive lymphocytes deployed from the scaffolds disclosed herein can actively migrate to affected tissue, seeking out and destroying residual tumor cells.

Pancreatic adenocarcinoma: An estimated 43,920 new cases of pancreatic cancer were expected to occur in the U.S. in 2012. Only 20% will have resectable disease at the time of diagnosis (80% of patients do not undergo surgery as their tumor is too advanced at the time of diagnosis). Even surgery is considered a palliative venture with a 5-year survival rate of only 20%. Local recurrence is usually attributed to the difficulty of achieving microscopically negative surgical margins. Beyond the current scaffold's ability to eradicate residual disease following surgical tumor resection, the scaffolds can also provide pancreatic tumor patients with inoperable disease (80% of patients) with a highly effective treatment option. In particular embodiments, scaffolds are implanted directly onto un-resectable established pancreatic adenocarcinomas.

Ovarian cancer: An estimated 22,000 new cases in 2012 in the U.S. were seen. Despite multimodality therapy with surgery and chemotherapy, most ovarian cancer patients have a poor prognosis (15,500 estimated deaths/year in U.S.). Ovarian cancer primarily disseminates within the peritoneal cavity. Adoptive T-cell therapy in ovarian cancer patients is currently being investigated at several centers. However, to date clinical results have been disappointing due to a poor survival of infused T-cells and a failure to combat immunosuppressive factors released by tumor cells to render T-cells dysfunctional. Multiple scaffolds embedded with tumor-reactive lymphocytes could be implanted laparoscopically into the peritoneal cavity of ovarian cancer patients, where they release tumor-reactive lymphocytes and STING agonists over an extended time period.

As will be understood by one of ordinary skill in the art, the scaffolds are implanted in close proximity to a solid tumor, un-resectable tumor cells and/or in tumor resection beds following resection. The scaffolds can be available in a number of different sizes and shapes and can be shape-conformable to fit the particular needs of individual subjects. In particular embodiments, the scaffolds are injected using ultrasound guidance in close proximity to (or in physical contact with) a solid tumor, un-resected or non-resected tumor cells. Depending on the stage, size or severity of a tumor, scaffolds may be provided with different therapeutic strengths. Therapeutic strength can be manipulated by altering the size of the scaffold, volume of the scaffold, the number of lymphocytes embedded within a scaffold, the number of lymphocyte-activating moieties within a scaffold, the presence or amount of STING agonists within the scaffold, etc. Each of these parameters can be assessed and determined by a treating physician.

For the purposes of the present disclosure, the term "proximity" refers to a distance within 10 cm, within 9 cm, within 8 cm, within 7 cm, within 6 cm, within 5 cm, within 4 cm, within 3 cm, within 2 cm, within 1 cm, within 0.9 cm, within 0.8 cm, within 0.7 cm, within 0.6 cm, within 0.5 cm, within 0.4 cm, within 0.3 cm, within 0.2 cm, or within 0.1 cm of a solid tumor, an un-resectable tumor, un-resectable tumor cells, and/or a tumor resection bed.

It is also understood by one of ordinary skill in the art that the scaffolds can be implanted only once, at the time of resection or at a first treatment time in a subject with a solid tumor, an un-resectable tumor, un-resectable tumor cells, and/or a tumor resection bed. Additionally, the scaffolds can be implanted a plurality of times to provide ongoing therapy over months or years. Such treatment regimens can be determined by a treating physician.

Figure 12I:
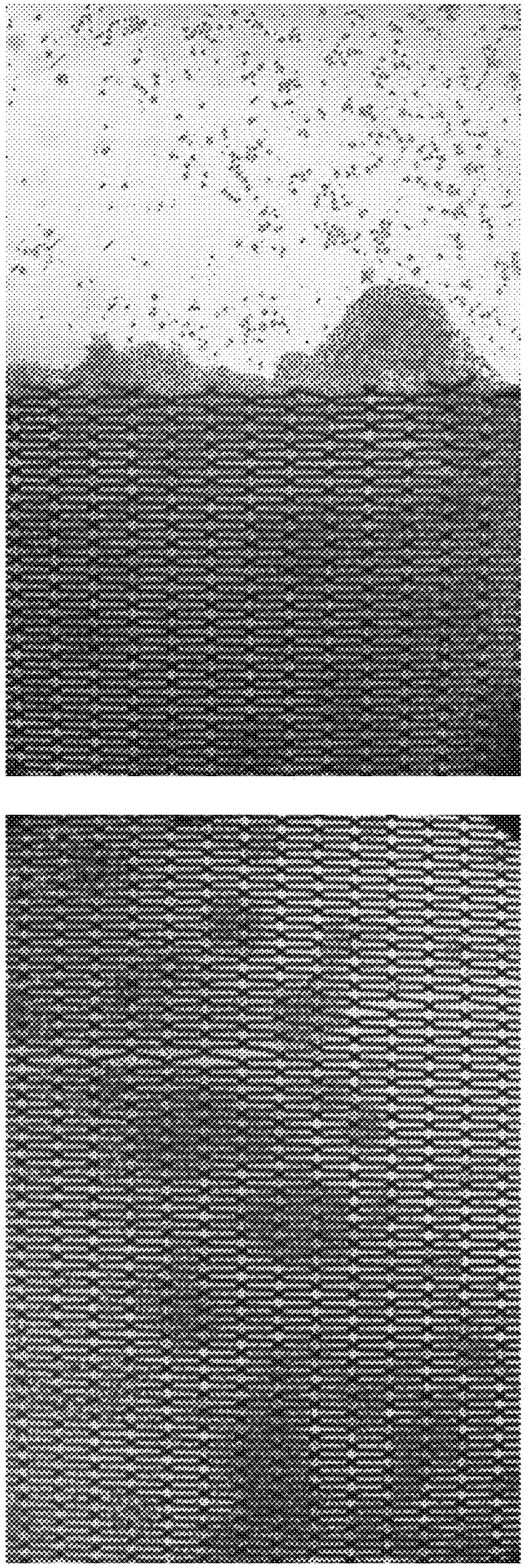
Figure 13B:
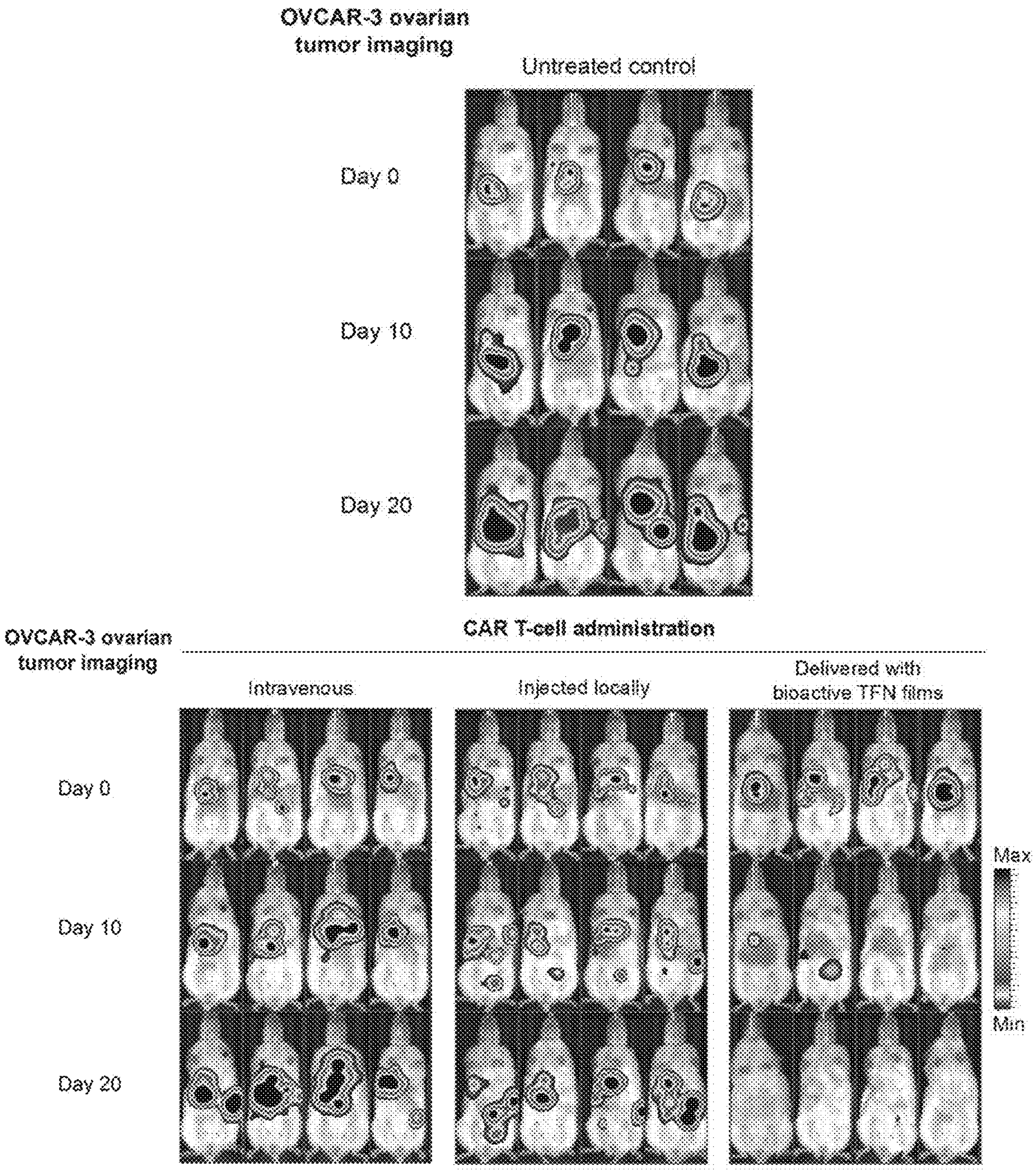
Figure 14:
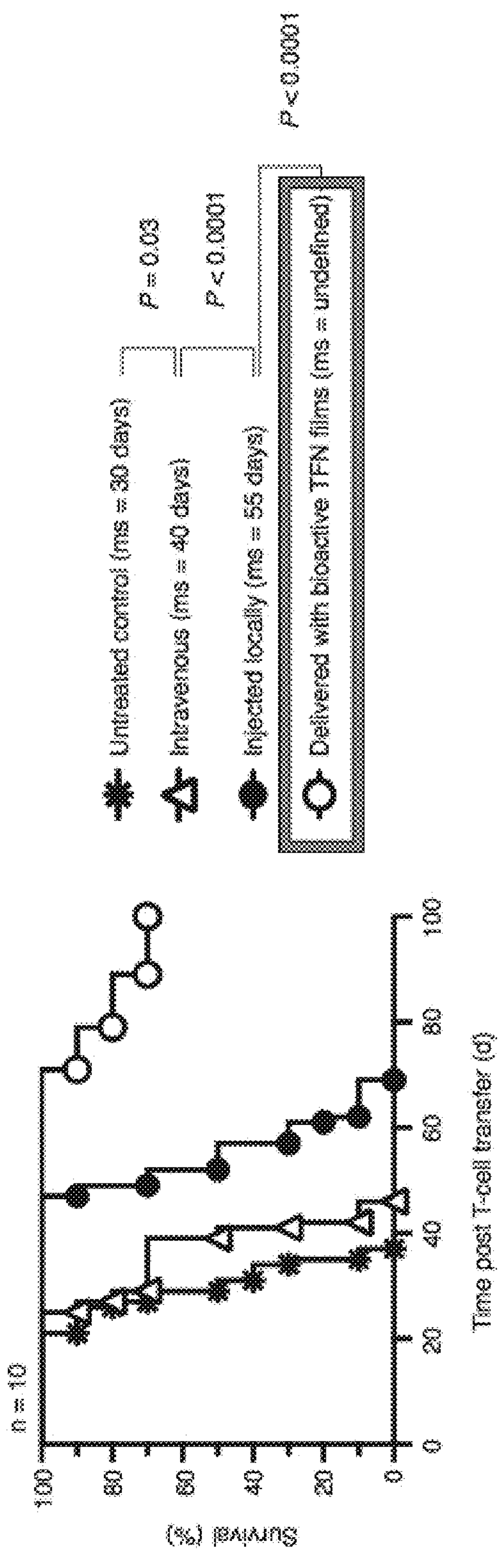
FIG. 14. Kaplan-Meier survival curve for mice treated with the TFN micromesh lymphocyte scaffold.
Figure 15:
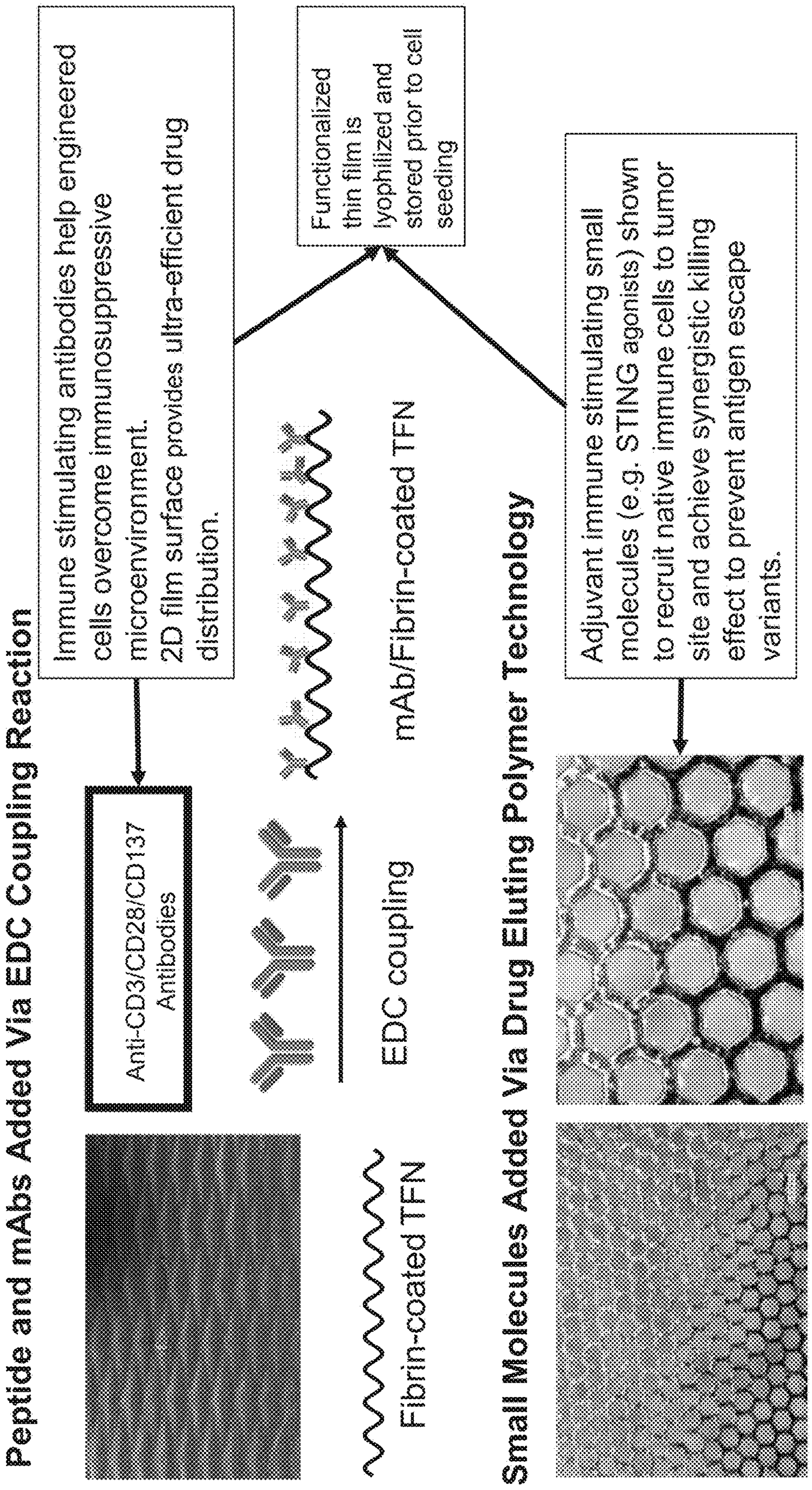
FIG. 15. Small molecules (e.g., STING agonists and/or immune stimulants) may be incorporated into lymphocyte scaffolds (e.g., TFN micromesh scaffolds) using a drug eluting polymer.

In particular embodiments, a lymphocyte scaffold including a TFN micromesh can be used as a long-acting scaffold (see, e.g., FIG. 12I). TFN micromesh can be used as a non-biodegradable scaffold matrix material, and therefore a TFN-micromesh based lymphocyte scaffold may continue to deliver lymphocytes for several days, for more than one week, and/or for more than two weeks.

As used herein, the term "surgical treatment failure" refers to relapse of cancer in a subject who had previously undergone tumor resection. Surgical treatment failure may include metastatic relapse.

The Examples and Exemplary Embodiments below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A lymphocyte scaffold including (i) genetically-reprogrammed lymphocytes disposed within a scaffold matrix including a micropatterned metallic thin film, and (ii) a lymphocyte-activating moiety.
2. The lymphocyte scaffold of embodiment 1, further including a STING agonist.
3. The lymphocyte scaffold of embodiment 2, wherein the STING agonist includes c-diGMP, c-diAMP, c-GAMP, c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)], c-[2'FdAMP(S)-2'FdIMP(S)](POM)2, and/or DMXAA.
4. The lymphocyte scaffold of embodiment 2, wherein the STING agonist includes c-diGMP.
5. The lymphocyte scaffold of any of embodiments 1-4, further including a drug eluting polymer.
6. The lymphocyte scaffold of embodiment 5, wherein the STING agonist is embedded within the drug eluting polymer.
7. The lymphocyte scaffold of embodiment 5 or 6, wherein the drug eluting polymer includes PLGA.
8. The lymphocyte scaffold of any of embodiments 1-7, wherein the lymphocytes include T-cells and/or natural killer cells.
9. The lymphocyte scaffold of any of embodiments 1-8, wherein the lymphocytes include CD8+ T-cells.
10. The lymphocyte scaffold of any of embodiments 1-9, including at least $2\times10^6$ lymphocytes.
11. The lymphocyte scaffold of any of embodiments 1-9, including at least $7\times10^6$ lymphocytes.
12. The lymphocyte scaffold of any of embodiments 1-11, wherein the lymphocyte-activating moiety includes at least one of IL-15, or an antibody specific for CD3, CD28, or CD137.
13. The lymphocyte scaffold of any of embodiments 1-12, wherein the lymphocyte-activating moiety includes antibodies specific for CD3, CD128, and CD137.
14. The lymphocyte scaffold of any of embodiments 1-13, wherein the lymphocyte-activating moiety includes IL-15 and CD137.
15. The lymphocyte scaffold of any of embodiments 1-14, further including an immune stimulant.
16. The lymphocyte scaffold of embodiment 15, wherein the immune stimulant is a cytokine, an antibody, a small molecule, an siRNA, a plasmid DNA, and/or a vaccine adjuvant.
17. The lymphocyte scaffold of embodiment 15, wherein the immune stimulant is selected from (i) a Toll-like receptor ligand selected from CpG, Cpg-28, Poly(I:C), α-galactoceramide, MPLA, VTX-2337, EMD1201081) imiquimod, MGN1703, G100, CBLB502, Hiltonol, and Imiquimod, and/or (ii) 17-dimethylaminoethylamino-17-demethoxygeldanamycin).
18. The lymphocyte scaffold of any of embodiments 15-17, wherein the immune stimulant is embedded within a drug eluting polymer.
19. The lymphocyte scaffold of any of embodiments 1-18, further including a lymphocyte-adhesion moiety.
20. The lymphocyte scaffold of embodiment 19, wherein the lymphocyte-adhesion moiety and the lymphocyte-activating moiety are covalently linked.
21. The lymphocyte scaffold of embodiment 19 or 20, wherein the lymphocyte-adhesion moiety includes fibrin.
22. The lymphocyte scaffold of any of embodiments 19-21, wherein the lymphocyte-adhesion moiety includes a peptide that binds $\alpha_I\beta_I$ integrin, $\alpha2\beta_I$ integrin, $\alpha4\beta_I$ integrin, $\alpha5\beta_I$ integrin, or lymphocyte function associated antigen (LFA-1).
23. The lymphocyte scaffold of any of embodiments 19-22, wherein the lymphocyte-adhesion moiety includes a GFOGER (SEQ ID NO: 1) peptide.
24. The lymphocyte scaffold of any of embodiments 19-23, wherein the lymphocyte-adhesion moiety includes a GFOGER (SEQ ID NO: 1) peptide of SEQ ID NO: 1 or SEQ ID NO: 2.
25. The lymphocyte scaffold of any of embodiments 19-24, wherein the lymphocyte-adhesion moiety includes an ICAM-1 peptide.
26. The lymphocyte scaffold of any of embodiments 19-25, wherein the lymphocyte-adhesion moiety includes an ICAM-1 peptide of SEQ ID NO: 3.
27. The lymphocyte scaffold of any of embodiments 19-26, wherein the lymphocyte-adhesion moiety includes a $FNIII_{7-10}$ peptide.
28. The lymphocyte scaffold of any of embodiments 19-27, wherein the lymphocyte-adhesion moiety includes a $FNIII_{7-10}$ peptide of SEQ ID NO: 4.
29. The lymphocyte scaffold of any of embodiments 2-28, wherein the STING agonist and/or the lymphocyte-activating moiety is linked to the scaffold matrix.
30. The lymphocyte scaffold of any of embodiments 2-29, wherein the STING agonist and/or the lymphocyte-activating moiety is embedded within the scaffold matrix.
31. The lymphocyte scaffold of any of embodiments 2-30, wherein the STING agonist and/or the lymphocyte-activating moiety is within a bioactive coating overlaying at least a portion of the surface of the scaffold matrix.
32. The lymphocyte scaffold of embodiment 31, wherein the bioactive coating includes a drug eluting polymer.
33. The lymphocyte scaffold of embodiment 32, further including a lymphocyte-adhesion moiety, wherein: the STING agonist is within the drug eluting polymer, the drug eluting polymer forms a monolayer on the surface of the scaffold matrix, and the lymphocyte-adhesion moiety directly coats the drug eluting polymer.
34. The lymphocyte scaffold of any of embodiments 2-33, wherein the STING agonist and/or the lymphocyte-activating moiety is linked to particles.
35. The lymphocyte scaffold of embodiment 34, wherein the particles are linked to the scaffold and/or embedded within the scaffold matrix.
36. The lymphocyte scaffold of any of embodiments 2-35, wherein the STING agonist and/or the lymphocyte-activating moiety is bound to a liposome of a protocell.
37. The lymphocyte scaffold of embodiment 36, wherein the ratio of the protocells to the lymphocytes within the scaffold matrix is 0.5:1; 1:1; 5:1; or 10:1.
38. The lymphocyte scaffold of any of embodiments 1-37, wherein the lymphocyte scaffold includes $7\times10^6$ to $1\times10^{10}$ protocells.

39. The lymphocyte scaffold of any of embodiments 1-38, wherein the micropatterned metallic thin film includes a TFN micromesh.
40. A lymphocyte scaffold consisting of a scaffold matrix, genetically reprogrammed lymphocytes, and three lymphocyte-activating moieties.
41. The lymphocyte scaffold of embodiment 40, wherein the scaffold matrix includes an alginate scaffold, a collagen/alginate scaffold, a chitosan scaffold, a self-assembling peptide scaffold, a mesoporous silica scaffold, a micropatterned metallic thin film scaffold, or a PLGA scaffold.
42. The lymphocyte scaffold of embodiment 40 or 41, wherein the micropatterned metallic thin film scaffold includes a TFN micromesh scaffold.
43. The lymphocyte scaffold of any of embodiments 40-42, wherein the scaffold matrix includes an alginate scaffold.
44. The lymphocyte scaffold of any of embodiments 40-43, wherein the scaffold matrix includes a polymeric calcium cross-linked alginate scaffold.
45. The lymphocyte scaffold of any of embodiments 40-44, wherein the genetically reprogrammed lymphocytes are genetically reprogrammed T-cells and/or natural killer cells.
46. The lymphocyte scaffold of any of embodiments 40-45, wherein the genetically reprogrammed lymphocytes are CD8+ T-cells.
47. The lymphocyte scaffold of any of embodiments 40-46, including at least $2\times10^6$ genetically reprogrammed lymphocytes.
48. The lymphocyte scaffold of any of embodiments 40-46, including at least $7\times10^6$ genetically reprogrammed lymphocytes.
49. The lymphocyte scaffold of any of embodiments 40-48, wherein the lymphocyte-activating moieties include antibodies specific for CD3, CD28, and/or CD137.
50. The lymphocyte scaffold of any of embodiments 40-49, wherein the lymphocyte-activating moieties are linked to the scaffold.
51. The lymphocyte scaffold of any of embodiments 40-50, wherein the lymphocyte-activating moieties are embedded within the scaffold.
52. A lymphocyte scaffold including: a scaffold matrix, genetically-reprogrammed lymphocytes, and a lymphocyte-activating moiety.
53. The lymphocyte scaffold of embodiment 52, further including a STING agonist.
54. The lymphocyte scaffold of embodiment 53, wherein the STING agonist includes c-diGMP, c-diAMP, c-GAMP, c-AIMP, (3',2')c-AIMP, (2',2')c-AIMP, (2',3') c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)], c-[2'FdAMP (S)-2'FdIMP(S)](POM)2, and/or DMXAA.
55. The lymphocyte scaffold of embodiment 52 or 53, wherein the STING agonist includes c-diGMP.
56. The lymphocyte scaffold of any of embodiments 52-55, wherein the genetically-reprogrammed lymphocytes are genetically-reprogrammed T-cells and/or natural killer cells.
57. The lymphocyte scaffold of any of embodiments 52-56, wherein the genetically-reprogrammed lymphocytes are CD8+ T-cells.
58. The lymphocyte scaffold of any of embodiments 52-57, including at least $2\times10^6$ or at least $7\times10^6$ genetically-reprogrammed lymphocytes.
59. The lymphocyte scaffold of any of embodiments 52-58, wherein the lymphocyte-activating moiety includes IL-15 and/or antibodies specific for CD3, CD28, and/or CD137.
60. The lymphocyte scaffold of any of embodiments 52-59, further including an immune stimulant.
61. The lymphocyte scaffold of embodiment 60, wherein the immune stimulant includes a cytokine, an antibody, a small molecule, an siRNA, a plasmid DNA, and/or a vaccine adjuvant.
62. The lymphocyte scaffold of embodiment 60 or 61, wherein the immune stimulant includes (i) a Toll-like receptor ligand selected from CpG, Cpg-28, Poly(I:C), α-galactoceramide, MPLA, VTX-2337, EMD1201081) imiquimod, MGN1703, G100, CBLB502, Hiltonol, and Imiquimod, and/or (ii) 17-dimethylaminoethylamino-17-demethoxygeldanamycin).
63. The lymphocyte scaffold of any of embodiments 52-62, further including a lymphocyte-adhesion moiety.
64. The lymphocyte scaffold of embodiment 63, wherein the lymphocyte-adhesion moiety includes fibrin.
65. The lymphocyte scaffold of embodiment 63 or 64, wherein the lymphocyte-adhesion moiety includes a peptide that binds $\alpha_1\beta_1$ integrin, $\alpha2\beta_1$ integrin, $\alpha4\beta_1$ integrin, $\alpha5\beta_1$ integrin, or lymphocyte function associated antigen (LFA-1).
66. The lymphocyte scaffold of any of embodiments 63-65, wherein the lymphocyte-adhesion moiety includes a GFOGER (SEQ ID NO: 1) peptide.
67. The lymphocyte scaffold of any of embodiments 63-66, wherein the lymphocyte-adhesion moiety includes a GFOGER (SEQ ID NO: 1) peptide of SEQ ID NO: 1 or SEQ ID NO: 2.
68. The lymphocyte scaffold of any of embodiments 63-67, wherein the lymphocyte-adhesion moiety includes an ICAM-1 peptide.
69. The lymphocyte scaffold of any of embodiments 63-68, wherein the lymphocyte-adhesion moiety includes an ICAM-1 peptide of SEQ ID NO: 3.
70. The lymphocyte scaffold of any of embodiments 63-69, wherein the lymphocyte-adhesion moiety includes a $FNIII_{7-10}$ peptide.
71. The lymphocyte scaffold of any of embodiments 63-70, wherein the lymphocyte-adhesion moiety includes a $FNIII_{7-10}$ peptide of SEQ ID NO: 4.
72. The lymphocyte scaffold of any of embodiments 53-71, wherein the STING agonist and/or the lymphocyte-activating moiety is linked to the scaffold matrix.
73. The lymphocyte scaffold of any of embodiments 53-72, wherein the STING agonist and/or the lymphocyte-activating moiety is embedded within the scaffold matrix.
74. The lymphocyte scaffold of any of embodiments 53-73, wherein the STING agonist and/or the lymphocyte-activating moiety is within a bioactive coating overlaying at least a portion of the surface of the scaffold matrix.
75. The lymphocyte scaffold of any of embodiments 53-74, wherein the STING agonist and/or the lymphocyte-activating moiety is linked to particles.

76. The lymphocyte scaffold of embodiment 75, wherein the particles are linked to the scaffold matrix and/or embedded within the scaffold matrix.
77. The lymphocyte scaffold of any of embodiments 53-76, wherein the STING agonist and/or the lymphocyte-activating moiety is bound to a liposome of a protocell.
78. The lymphocyte scaffold of embodiment 77, wherein the ratio of the protocells to the lymphocytes within the scaffold matrix is 0.5:1; 1:1; 5:1; or 10:1.
79. The lymphocyte scaffold of any of embodiments 53-78, wherein the lymphocyte scaffold includes $7\times10^6$ to $1\times10^{10}$ protocells.
80. The lymphocyte scaffold of any of embodiments 52-79, wherein the scaffold matrix includes an alginate scaffold, a collagen/alginate scaffold, a chitosan scaffold, a self-assembling peptide scaffold, a mesoporous silica scaffold, a micropatterned metallic thin film scaffold, or a PLGA scaffold.
81. The lymphocyte scaffold of embodiment 80, wherein the micropatterned metallic thin film scaffold includes a TFN micromesh scaffold.
82. The lymphocyte scaffold of embodiment 80 or 81, wherein the scaffold matrix includes an alginate scaffold.
83. The lymphocyte scaffold of any of embodiments 80-82, wherein the scaffold matrix includes a polymeric calcium cross-linked alginate scaffold.
84. A lymphocyte scaffold including: (i) a scaffold matrix material, (ii) natural killer cells with anti-cancer activity, and (iii) lymphocyte-activating moieties including IL-15 and an antibody specific to CD137.
85. The lymphocyte scaffold of embodiment 84, wherein the scaffold matrix material includes a micropatterned metallic thin film.
86. The lymphocyte scaffold of embodiment 84 or 85, wherein the micropatterned metallic thin film includes a TFN micromesh.
87. The lymphocyte scaffold of any of embodiments 84-86, further including a STING agonist.
88. The lymphocyte scaffold of embodiment 113, wherein the STING agonist includes c-diGMP, c-diAMP, c-GAMP, c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)], c-[2'FdAMP(S)-2'FdIMP(S)](POM)2, and/or DMXAA.
89. The lymphocyte scaffold of any of embodiments 84-88, further including a drug-eluting polymer.
90. The lymphocyte scaffold of embodiment 89, wherein the drug eluting polymer includes PLGA.
91. The lymphocyte scaffold of embodiment 87 or 88 wherein the STING agonist is embedded within a drug eluting polymer.
92. The lymphocyte scaffold of any of embodiments 84-91, further including a lymphocyte-adhesion moiety.
93. The lymphocyte scaffold of embodiment 92, wherein the lymphocyte-adhesion moiety includes fibrin.
94. The lymphocyte scaffold of embodiment 92 or 93, wherein the lymphocyte-adhesion moiety includes a peptide that binds $\alpha_I\beta_I$ integrin, $\alpha2\beta_I$ integrin, $\alpha4\beta_I$ integrin, $\alpha5\beta_I$ integrin, or lymphocyte function associated antigen (LFA-1).
95. The lymphocyte scaffold of any of embodiments 92-94, wherein the lymphocyte-adhesion moiety includes a GFOGER (SEQ ID NO: 1) peptide.
96. The lymphocyte scaffold of any of embodiments 92-95, wherein the lymphocyte-adhesion moiety includes a GFOGER (SEQ ID NO: 1) peptide of SEQ ID NO: 1 or SEQ ID NO: 2.
97. The lymphocyte scaffold of any of embodiments 84-96, wherein the lymphocyte-adhesion moiety includes an ICAM-1 peptide.
98. The lymphocyte scaffold of any of embodiments 84-97, wherein the lymphocyte-adhesion moiety includes an ICAM-1 peptide of SEQ ID NO: 3.
99. The lymphocyte scaffold of any embodiments 84-98, wherein the lymphocyte-adhesion moiety includes a $FNIII_{7-10}$ peptide.
100. The lymphocyte scaffold of any of embodiments 84-99, wherein the lymphocyte-adhesion moiety includes a $FNIII_{7-10}$ peptide of SEQ ID NO: 4.
101. A method of treating a heterogenous solid tumor including escape variant tumor cells in a subject including implanting a lymphocyte scaffold of any of embodiments 1-100 into the subject within a proximity of the heterogenous solid tumor cell sufficient to lead to the destruction of the heterogenous solid tumor in the subject, thereby treating the heterogenous solid tumor including escape variant tumor cells.
102. A method of vaccinating a subject against development of cancer recurrence including implanting a lymphocyte scaffold of any of embodiments 1-100 into the subject within a proximity of a heterogenous solid tumor or within a solid tumor resection bed in the subject, thereby vaccinating the subject against development of cancer recurrence.
103. A method of treating tumor cells in a subject in need thereof including implanting a lymphocyte scaffold of any of embodiments 1-100 into the subject within a tumor resection bed thereby treating the tumor cells in the subject.
104. The method of embodiment 103, wherein a treated tumor cell is an adrenal cancer cell, a brain cancer cell, a breast cancer cell, a cervical cancer cell, a colon cancer cell, a colorectal cancer cell, an ear, nose and throat (ENT) cancer cell, an endometrial cancer cell, an esophageal cancer cell, a gastrointestinal cancer cell, a glioma cell, a head and neck cancer cell, an intestinal cancer cell, a kidney cancer cell, a liver cancer cell, a lung cancer cell, a lymph node cancer cell, a melanoma cell, a neuroblastoma cell, an ovarian cancer cell, a pancreatic cancer cell, a prostate cancer cell, a rectal cancer cell, a seminoma cell, a skin cancer cell, a stomach cancer cell, a teratoma cell, a thyroid cancer cell, or a uterine cancer cell.
105. The method of embodiment 103, wherein a treated tumor cell is a glioblastoma cell, a pancreatic adenocarcinoma cell, or an ovarian cancer cell.
106. A method of reducing surgical treatment failure caused by metastatic relapse after resection of a primary tumor, including administering a lymphocyte scaffold of any of embodiments 1-100 to a tumor resection bed of a subject thereby reducing surgical treatment failure caused by metastatic relapse after primary tumor resection.
107. The method of embodiment 106, wherein the primary tumor includes a seminoma cell, a melanoma cell, a teratoma cell, a neuroblastoma cell, a glioma cell, a rectal cancer cell, an endometrial cancer cell, a kidney cancer cell, an adrenal cancer cell, a thyroid cancer cell, a skin cancer cell, a brain cancer cell, a cervical cancer cell, an intestinal cancer cell, a liver cancer cell, a colon cancer cell, a stomach cancer cell, a head and neck cancer cell, a gastrointestinal cancer cell, a lymph node cancer cell, an esophageal cancer cell, a colorectal cancer cell, a pancreatic cancer cell, an ear, nose and throat (ENT) cancer cell, a breast cancer cell, a prostate cancer cell, a uterine cancer cell, an ovarian cancer cell, or a lung cancer cell.

108. A method of treating a subject for cancer including implanting into the subject a medical device coated with a lymphocyte scaffold including a TFN micromesh, genetically-modified lymphocytes, and a lymphocyte activating moiety.

109. The method of embodiment 108, wherein the implanting includes a minimally invasive procedure.

110. The method of embodiment 108, wherein the medical device includes a stent.

111. A kit to form a lymphocyte scaffold to treat a solid tumor in a subject including (i) a scaffold matrix; and (ii) lymphocyte-activating moieties including antibodies specific for CD3, CD28, and CD137.

112. The kit of embodiment 111, further including porous particles.

113. The kit of embodiment 111 or 112, further including liposomes.

114. The kit of any of embodiments 111-113, further including protocells.

115. The kit of any of embodiments 111-114, further including a STING agonist.

116. The kit of embodiment 115, wherein the STING agonist includes c-diGMP, c-diAMP, c-GAMP, c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)], c-[2'FdAMP(S)-2'FdIMP(S)](POM)2, and/or DMXAA.

117. The kit of embodiment 115, wherein the STING agonist includes c-diGMP.

118. The kit of any of embodiments 111-117, further including an immune stimulant.

119. The kit of embodiment 118, wherein the immune stimulant includes a cytokine, an antibody, a small molecule, an siRNA, a plasmid DNA, and/or a vaccine adjuvant.

120. The kit of embodiment 118 or 119, wherein the immune stimulant includes (i) a Toll-like receptor ligand selected from CpG, Cpg-28, Poly(I:C), α-galactoceramide, MPLA, VTX-2337, EMD1201081) imiquimod, MGN1703, G100, CBLB502, Hiltonol, and Imiquimod, and/or (ii) 17-dimethylaminoethylamino-17-demethoxygeldanamycin).

121. The kit of any of embodiments 111-120, further including a lymphocyte-adhesion moiety.

122. The kit of embodiment 121, wherein the lymphocyte-adhesion moiety includes fibrin.

123. The kit of embodiment 121 or 122, wherein the lymphocyte-adhesion moiety includes a peptide that binds $\alpha_1\beta_1$ integrin, $\alpha 2\beta_1$ integrin, $\alpha 4\beta_1$ integrin, $\alpha 5\beta_1$ integrin, or lymphocyte function associated antigen (LFA-1).

124. The kit of any of embodiments 121-123, wherein the lymphocyte-adhesion moiety includes a GFOGER (SEQ ID NO: 1) peptide.

125. The kit of any of embodiments 121-124, wherein the lymphocyte-adhesion moiety includes a GFOGER (SEQ ID NO: 1) peptide of SEQ ID NO: 1 or SEQ ID NO: 2.

126. The kit of any of embodiments 121-125, wherein the lymphocyte-adhesion moiety includes an ICAM-1 peptide.

127. The kit of any of embodiments 121-126, wherein the lymphocyte-adhesion moiety includes an ICAM-1 peptide of SEQ ID NO: 3.

128. The kit of any of embodiments 121-127, wherein the lymphocyte-adhesion moiety includes a $FNIII_{7-10}$ peptide.

129. The kit of any of embodiments 121-128, wherein the lymphocyte-adhesion moiety includes a $FNIII_{7-10}$ peptide of SEQ ID NO: 4.

130. The kit of any of embodiments 111-129, wherein the kit includes $7\times10^6$ to $1\times10^{10}$ particles, liposomes or protocells.

131. The kit of any of embodiments 111-130, further including genetically-reprogrammed lymphocytes.

132. The kit of embodiment 131, wherein the genetically-reprogrammed lymphocytes include T-cells and/or natural killer cells.

133. The kit of embodiment 131 or 132, wherein the genetically-reprogrammed lymphocytes include CD8+ T-cells.

134. The kit of any of embodiments 131-133, wherein the lymphocytes include at least $7\times10^6$ lymphocytes.

135. The kit of any of embodiments 131-134, wherein the scaffold matrix includes alginate, collagen, chitosan, a self-assembling peptide, mesoporous silica, TFN micromesh, or PLGA.

136. The kit of embodiment 135, wherein the scaffold matrix includes alginate.

137. The kit of any of embodiments 111-136, further including calcium.

138. The kit of any of embodiments 111-137, further including a drug eluting polymer.

139. The kit of embodiment 138, wherein the drug eluting polymer is coated on the scaffold matrix.

140. The kit of embodiment 138, wherein a STING agonist or an immune stimulant is embedded within the drug eluting polymer.

141. The kit of any of embodiments 111-140, wherein the drug eluting polymer includes PLGA.

142. An implantable medical device including: (i) a micropatterned metallic thin film scaffold, (ii) genetically reprogrammed lymphocytes, and (iii) a lymphocyte-activating moiety.

143. The implantable medical device of embodiment 142 further including a STING agonist and/or an immune stimulant.

144. The implantable medical device of embodiment 143 further including a drug eluting polymer, wherein the STING agonist and/or the immune stimulant is embedded within the drug eluting polymer.

145. The implantable medical device of any of embodiments 142-144, wherein the micropatterned metallic thin film scaffold has a three-dimensional shape.

146. The implantable medical device of embodiment 145, wherein the three-dimensional shape is a cylinder.

147. The implantable medical device of any of embodiments 142-146, including a stent.

148. The implantable medical device of any of embodiments 142-147, including a minimally invasive medical device.

149. The implantable medical device of any of embodiments 142-148, wherein the micropatterned metallic thin film scaffold is stacked in layers.

150. The implantable medical device of any of embodiments 142-149, wherein the micropatterned metallic thin film includes a TFN micromesh.

151. The implantable medical device of any of embodiments 142-150, wherein the genetically-reprogrammed lymphocytes are at a concentration of at least $7\times10^6$ cells/$cm^3$.

Examples. Methods. Human pancreatic ductal adenocarcinoma. For the confocal imaging of human pancreatic adenocarcinoma (PDA, FIG. 1) fresh tumor was procured from patients undergoing pancreatic resection for PDA, who provided written informed consent under a research protocol approved by the Cancer Consortium Institutional Review Board (CC-IRB) at the Fred Hutchinson Cancer Research Center.

Cell lines. The murine pancreatic ductal adenocarcinoma cell line KPC, a gift from Dr. Sunil Hingorani (Fred Hutchinson Cancer Research Center, Seattle, WA), was derived from spontaneously developing pancreatic tumors of transgenic KPC (LSL-KrasG12D; p53lox/+) mice at 17 weeks of age. This cell line was cultured in IMDM medium with 10% heat-inactivated fetal bovine serum (FBS), 2 mM L-glutamine, 1.5 g/L sodium bicarbonate, 4.5 g/L glucose, 10 mM HEPES, 1.0 mM sodium pyruvate, and 0.05 mM 2-mercaptoethanol. The Phoenix™ Eco retroviral packaging cell line (Orbigen) was cultured in DMEM containing 10% FBS, 2 mM glutamate, 100 U/mL penicillin, and 100 μg/mL streptomycin. For in vivo bioluminescent imaging, the KPC cell line was retrovirally transduced with firefly luciferase (F-luc).

Mice and in vivo tumor model. Animals were housed in the animal facility of Fred Hutchinson Cancer Research Center, and used in the context of an animal protocol approved by their Institutional Animal Care and Use Committee. For the orthotopic mouse model of pancreatic ductal adenocarcinoma, $1\times10^5$ KPC tumor cells were surgically implanted into the head of the pancreas in female Albino B6 (C57BL/6J-Tyr<c-2J>) mice (Jackson Laboratories) and were allowed to establish for one week before treatment. To differentiate between adoptively transferred and endogenous T cells in the flow cytometry studies shown in FIG. 7A, 7B, NKG2D CAR T cells were generated from splenocytes isolated from wild-type (CD45.2+) C57BL/6 mice. Following gene transfer, T cells were used to treat B6.SJL-Ptprca Pepcb/BoyJ recipient mice (Jackson Laboratories), which express the pan leukocyte marker CD45.1.

Retroviral vectors and viral production. SFG-CBR-luc (expressing click beetle red luciferase) and SFG-F-luc (expressing firefly luciferase) were kindly provided by Dr. Michel Sadelain (Memorial Sloan-Kettering Cancer Center, New York). The retroviral vector pFb-chNKG2D-IRES-Neo was provided by Dr. Charles Sentman (The Geisel School of Medicine at Dartmouth, Lebanon), and has been described previously. Zhang, et al., Blood $10^6$, 1544-1551 (2005). NKG2D CARs include the full-length mouse NKG2D (UniProt ID No. O54709) fused with the cytoplasmic portion of CD3ζ. To generate retroviral particles, Phoenix™ Eco retroviral packaging cells ($1.5\times10^6$/10 cm culture plate) were transfected overnight with 10 μg of vector-DNA using standard calcium phosphate methods; the following day, they were incubated in 10 mL fresh DMEM for an additional day before the retroviral supernatant was filtered (0.45-μm, Nalgene) and concentrated 10-fold using Ultracel 100K membranes (Millipore).

Preparation of tumor-targeting lymphocytes. To generate pancreatic cancer-specific (NKG2D CAR-transduced) T cells, spleens of C57BL/6J mice were harvested, macerated over a filter, and resuspended in ACK lysing Buffer (Biosource). Effector CD8+ T cells were prepared by incubating splenocytes ($3\times10^6$/mL) in complete RPMI 1640 with 1 ng/mL interleukin-7 (PeproTech) and 2 μg/mL Concavalin A (Calbiochem) at 37° C. Two days later, dead cells were removed by Ficoll® polysaccharide gradient separation (GE Healthcare) and CD8+ cells were isolated using a mouse CD8 Negative Isolation Kit (Stemcell Technologies). Introduction of the NKG2D CAR into T cells was performed by retroviral transduction. Concentrated NKG2D CAR expressing retrovirus (1 mL) was preloaded onto six-well non-tissue culture treated dishes coated with RetroNectin® recombinant human fibronectin (TakiraBio) and incubated at 37° C. for 1 hr. An equal volume of isolated T-cells ($3\times10^6$ cells/mL supplemented with 10 ng mIL-2/mL) was added and centrifuged at 2000×g for 30 min). 6 hr after spinoculation, 1 mL of fresh, prewarmed RPMI, containing 10 ng mIL-2 (PeproTech) was added. Two days after infection, transduced primary T cells (0.5-1×10/mL) were selected in RPMI-10 media containing G418 (0.5 mg/mL) plus 25 U/mL recombinant human (rHu) IL-2 for an additional 3 days. Viable cells were isolated using Histopaque®-1083 polysucrose and sodium diatrizoate solution (Sigma, St Louis, MO) and expanded for 2 days without G418 before adoptive transfer. For bioluminescence T-cell imaging experiments, the targeted T cells were genetically tagged with click beetle red luciferase (CBR-luc). Dobrenkov, et al., J Nucl Med 49, 1162-1170 (2008). Six hours after this spinoculation, 1 mL of RPMI containing 50 IU IL-2 was added, and the transduced T cells were used for experiments 1 day later.

Preparation of stimulatory lipid-coated silica microspheres. Preparation of maleimide-functionalized lipid film. Lipid stock solutions were formulated in chloroform. 140 mL DOPC (10 mg/mL), 30 mL DSPE-PEG(2000) maleimide (5 mg/mL), 150 mL cholesterol (5 mg/mL), and 50 mL 18:1 PEG 2000-PE (5 mg/mL, all purchased from Avanti Polar Lipids) were combined to attain a DOPC:DSPE-PEG (2000) maleimide:cholesterol:PEG 2000-PE mass ratio of 55:5:30:10 and 2.5 mg total lipid. Chloroform was evaporated under a stream of nitrogen and residual solvent was removed under vacuum overnight.

Amine modification of silica microparticles. 500 mg of spherical silica gel (15 μm particle diameter, 100 Å pore diameter, Sorbent Technologies) was suspended in 4 mL of a 25% solution of 3-[2-(2-aminoethylamino)ethylamino] propyltrimethoxysilane (AEPTMS) in ethanol then mixed gently at room temperature for 5 h. Unreacted AEPTMS was removed by centrifugation (2 min, 1000×g) and decantation of the supernatant. The amine-modified silica was washed with ethanol (4×2 mL) then air-dried for 2 days.

Loading of STING agonist into mesoporous silica microparticles. A 100 mg/mL suspension of amine-modified silica was prepared in phosphate buffered saline at pH 7.2 (PBS), and 360 μL of it was combined with 500 μL of c-di-GMP (InvivoGen, 2 mg/mL in PBS), gently vortexed for 1 h, then diluted with 400 μL PBS.

Lipid adsorption on silica. 400 μL of the SiO2/c-di-GMP suspension was added to a 2.5 mg batch of lipid film and vortexed for 15 s at 10 min intervals for a total of 1 h. The particles were pelleted at 3500×g for 2 min, washed with PBS (2×1 mL), then resuspended in 250 μL PBS.

Antibody conjugation to lipid-coated particles. The hinge region disulfide bonds of anti-mouse CD3, CD28, and CD137 antibodies (BioXcell) were selectively reduced with dithiothreitol (DTT) as previously described. Kwong, et al., Cancer Res 73, 1547-1558 (2013). After DTT was removed with a desalting column, these mildly-reduced antibodies (anti-CD3: 200 μg; anti-CD28 and CD137: 400 μg) were added to 250 μL maleimide-functionalized particles, vortexed briefly before rotation for 2 h, and centrifuged at 3500×g for 2 min. The pellet was washed with PBS (2×1 mL), then suspended in 125 μL PBS.

Scaffold fabrication. Alginate scaffolds were produced from high molecular weight (250 kDa) ultrapure sodium alginate powder (Novamatrix Pronova UP MVG alginate) enriched in G blocks 60%) after it was oxidized with sodium periodate to create hydrolytically labile bonds, as previously described. Boontheekul, et al., Biomaterials 26, 2455-2465 (2005).

Briefly, 200 μL of 0.25% sodium periodate was added dropwise to 10 mL aqueous 1% alginate, and stirred in the dark at 25° C. for 5 h before the reaction was quenched by stirring with equimolar ethylene glycol for 30 min. The sample was dialyzed against deionized water for three days using membranes with a 3,500 molecular weight cut-off, then lyophilized. The oxidized alginate solution was reconstituted in a MES solution (0.1 M MES, 0.3 M NaCl, pH 6.5) and covalently conjugated to the collagen-mimetic peptide "GFOGER50" (obtained from the MIT Biopolymers facility) using carbodiimide chemistry51: sulfo-NHS, EDC (both Thermo Scientific), and the GFOGER (SEQ ID NO: 1) peptide were added sequentially, and 24 h later the solution was again dialyzed (MWCO 20 kDa dialysis membrane, Thermo Scientific) and lyophilized.

To make scaffolds, the alginate stock was reconstituted to 7 mL of a 2% w/v solution in PBS, and warmed to 55° C. before mixing with $7\times10^6$ stimulatory microspheres in aqueous suspension. Mild cross-linking was initiated by adding 1.4 mL of 0.1% (w/v) calcium chloride solution while vortexing, then 700 μL was immediately transferred per 15 mm round Teflon™ (polytetrafluoroethylene)-coated mold to form 2 mm-thick scaffolds. These were frozen at −78° C. and lyophilized to yield porous matrices, which were stored at 4° C. in a desiccator.

T cell seeding onto scaffolds. Following ex vivo expansion, mouse CD8+ effector T cells specific for 4T1 breast tumor antigens or genetically engineered to express NKG2D-CAR were washed twice in PBS and resuspended in non-supplemented RPMI medium at a concentration of $14\times10^6$ cells/mL. After adding 5% AlgiMatrix™ animal origin-free 3D cell culture system Firming Buffer (Invitrogen), 500 μL of this cell suspension was immediately inoculated on top of each lyophilized scaffold in a 24-well tissue culture plate. Cells were allowed to infuse into these matrices on ice for 30 min before implantation into the tumor resection cavity or the peritoneal cavity.

Cytotoxicity assays. In vitro cytotoxic activity of T cells was measured using standard $^{51}$Cr release assays as described elsewhere. Erskine, J Vis Exp, e3683 (2012). Briefly, 4T1 breast tumor, ID8-VEGF ovarian tumor or B16F10 melanoma control tumor cells were labeled with $^{51}$Cr for 1 h at 37° C., washed with RPMI containing 10% FCS, and resuspended in the same medium at a concentration of $1\times10^5$ tumor cells/mL. T cells were added to the suspensions at varying effector-to-target cell ratios in 96-well plates (final volume, 200 μL) and incubated for 4 h at 37° C., then 30 μL of supernatant from each well was transferred into Lumaplate-96 microplates (Packard Bioscience) for analysis with a Top Count NXT microplate scintillation counter (Packard Bioscience). Effector cell numbers were calculated based on the total number of IFN-γ+ CD8+ T cells measured by flow cytometry using commercially available kits (R&D Systems).

In vivo bioluminescence and imaging. D-Luciferin (Xenogen) in PBS (15 mg/mL) was used as a substrate for F-luc (imaging of 4T1 breast tumor and ID8-VEGF ovarian tumor) and CBR-luc47 (T-cell imaging). Bioluminescence images were collected with a Xenogen IVIS® non-invasive Spectrum Imaging System (Xenogen, Alameda, CA). Living Image® in vivo imaging software version 4.3.1 (Xenogen) was used to acquire (and later quantitate) the data 10 min after intraperitoneal injection of D-luciferin into animals anesthetized with 150 mg/kg of 2% isoflurane (Forane, Baxter Healthcare). Acquisition times ranged from 10 sec to 5 min.

Flow cytometry. Anti-recombinant Annexin V (used to quantify apoptotic cells) and other antibodies used with the FACSCanto™ Flow Cytometer (BD Biosciences) were purchased from eBioscience.

Confocal microscopy. To visualize scaffolds by confocal microscopy, HiLyte™ Fluor 647 carbonyl-reactive fluorescent labeling dye (Anaspec) was conjugated to alginate using standard EDC/NHS chemistry, then mixed 1 part of the conjugate with 9 parts of GFOGER (SEQ ID NO: 1) peptide-modified alginate to fabricate scaffolds as described above. T cells were labeled with CellTracker™ Orange CMTMR fluorescent dye (Invitrogen) immediately before seeding into these scaffolds. Three days post-implantation, the tumor resection bed was snap-frozen in OCT formulation of clear, water-soluble glycols and resins (Tissue-Tek®) to produce cryosections, which were fixed with 2% paraformaldehyde, mounted in ProLong™ Gold Antifade liquid mountant reagent (Invitrogen), and imaged with a Zeiss® LSM 780 NLO laser scanning confocal microscope.

Statistics. Statistical significance of measured differences in T cell migration parameters was calculated using one-way ANOVA, followed by Dunnett's comparison test. Pairwise differences in the bioluminescent tumor and T cell signals were analyzed at selected time points using the Wilcoxon rank-sum test, and survival data was characterized using the Log-rank test. All statistical analyses were performed using GraphPad Prism software version 6.0.

Study approval. Experiments and handling of mice were conducted under federal, state, and local guidelines under an IACUC protocol and with approval from the Fred Hutchinson Cancer Research Center IACUC.

Figure 2A:
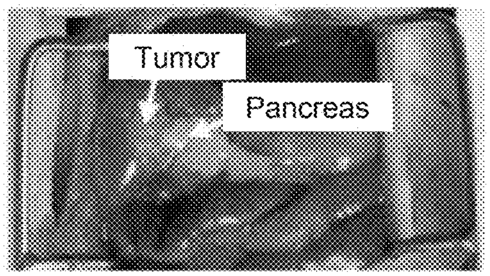
FIGS. 2A-2I. Systemic infusions of tumor-specific CAR-T cells produce only modest therapeutic benefits.
Figure 2B:
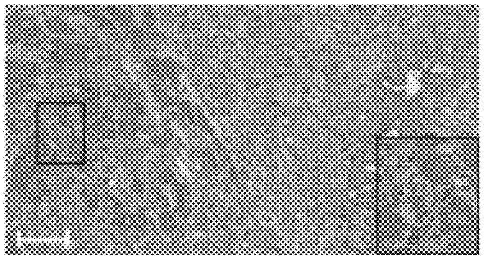
Figure 2C:
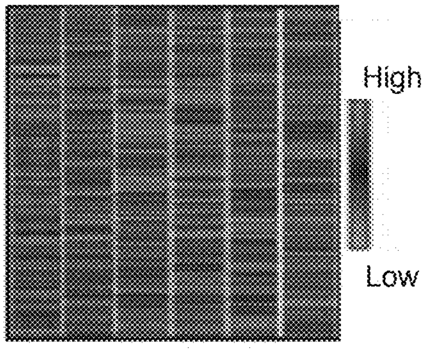

Results. Intravenous injections of tumor-reactive T cells fail to clear pancreatic ductal adenocarcinoma. In order to test the new immunotherapy approach in a clinically relevant setting, described experiments were performed using a cell line derived from the spontaneous pancreatic tumors that LSL-KrasG12D; p53lox/+ (KPC) mice produce (Hingorani, et al. *Cancer Cell* 7, 469-483 (2005)); this allowed creation of an immunocompetent, orthotopic murine model of pancreatic cancer that has rapid and predictable growth kinetics. The KPC cells were genetically tagged with luciferase so that tumor burdens could be noninvasively quantified using bioluminescence imaging. When orthotopically transplanted into the pancreas of non-KPC littermates, these tumor cells reproducibly develop into lesions that mimic human pancreatic cancer in terms of genetic mutations, histologic appearance, and heterogeneity of antigen/target expression (FIGS. 2A-2C).

Figure 2D:
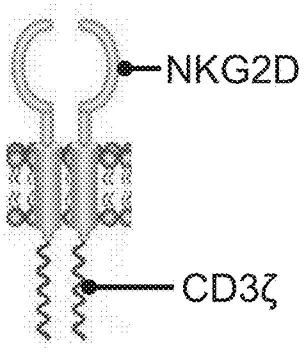
Figure 2E:
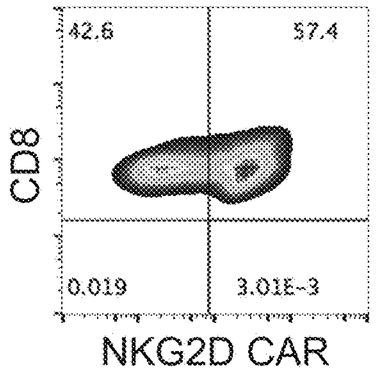
Figure 2F:
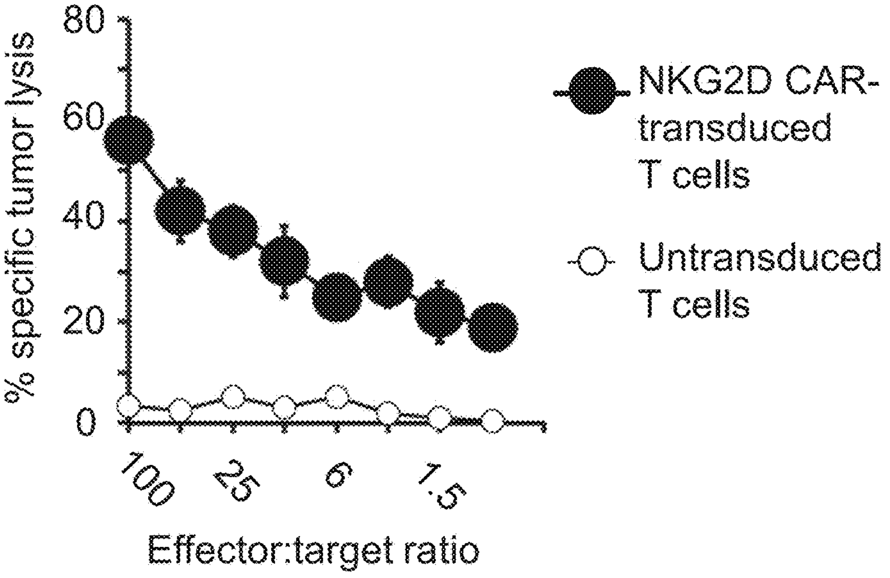
Figure 2G:
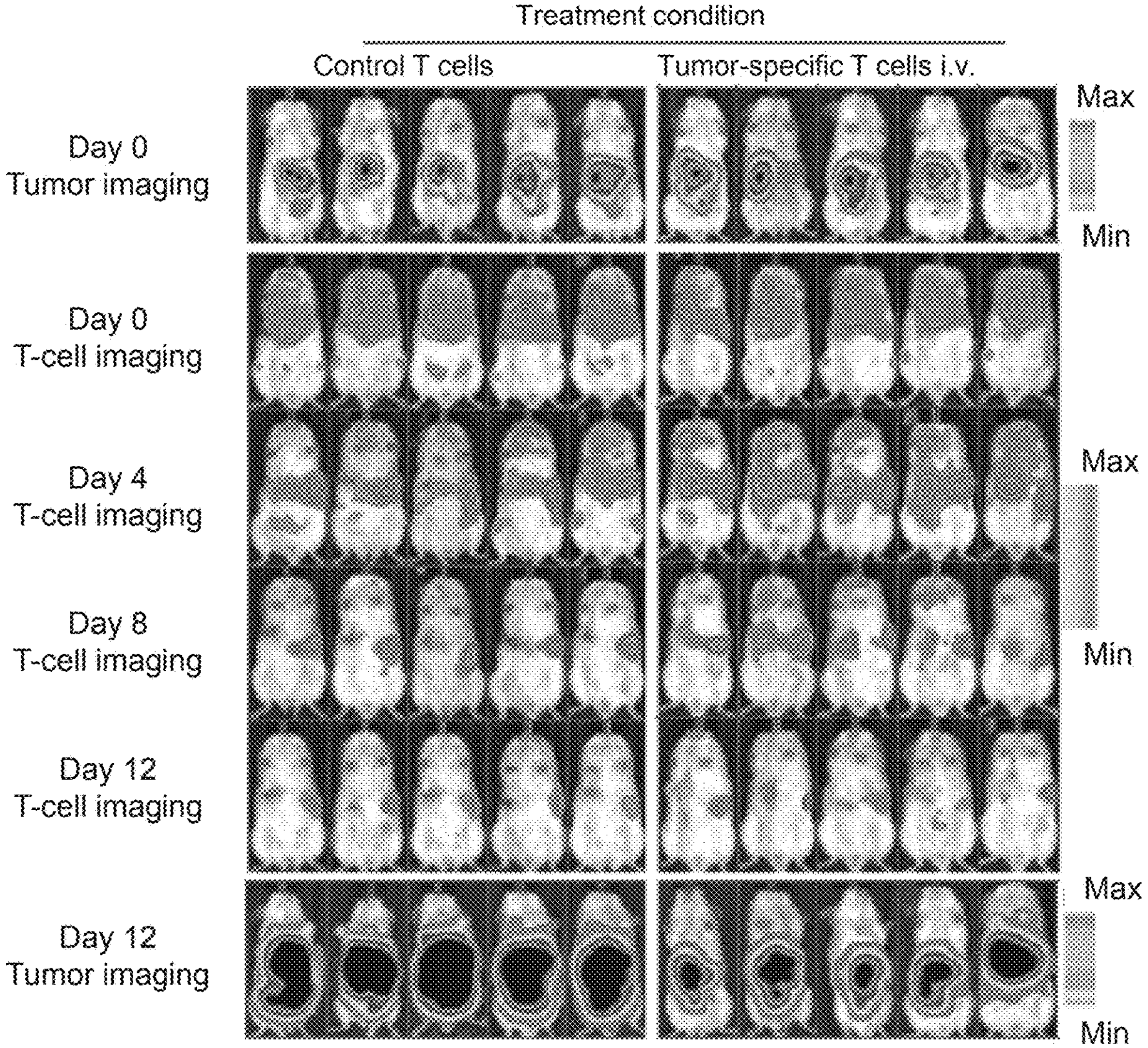
Figure 2H:
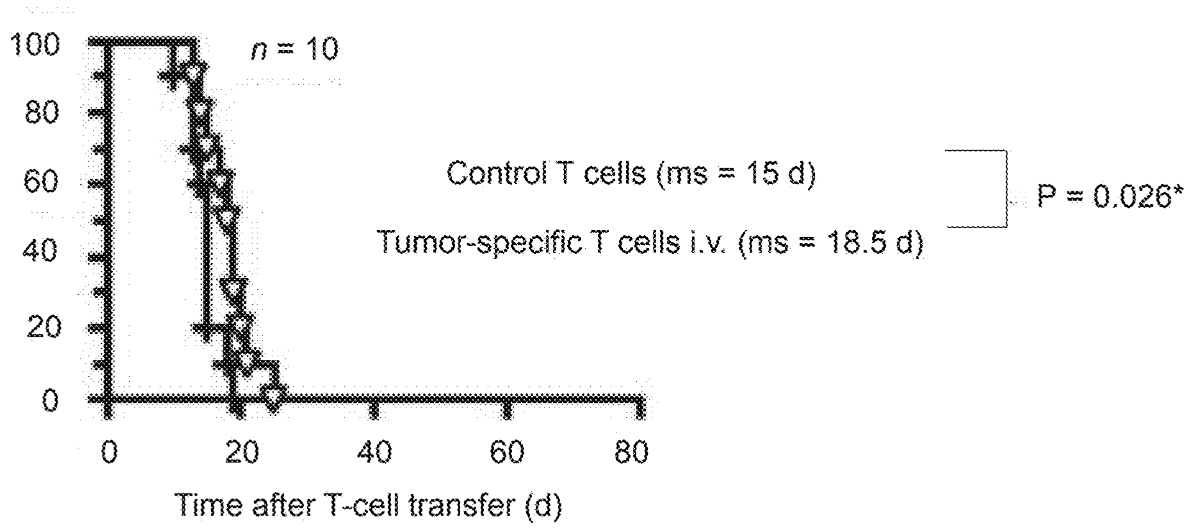
Figure 2I:
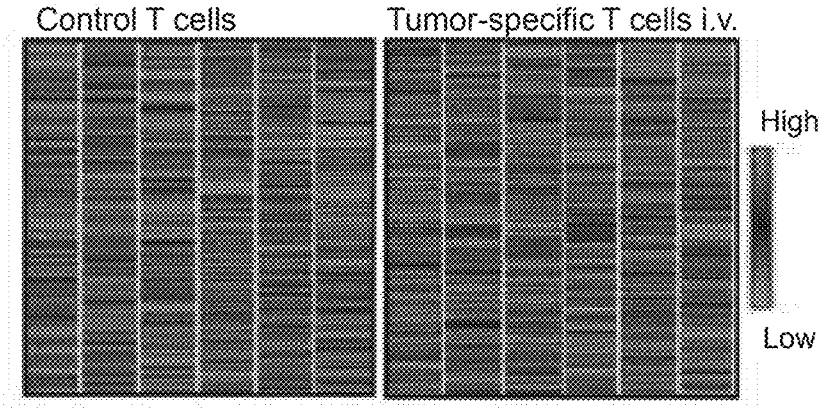

It was first verified that conventional intravenous injections of pancreatic cancer-specific lymphocytes fail to eradicate tumors in this KPC model. To create these lymphocytes, mouse T cells were transduced with a retrovirus encoding a chimeric natural killer receptor (including NKG2D linked to the cytoplasmic signaling domain of CD3ζ30; FIG. 2D) that is specific for Rae-1, a KPC antigen that is recognized by T cells expressing these receptors (FIGS. 2E, 2F). In order to track and quantify the in vivo migration and accumulation of the transferred T cells in relation to KPC tumors, vectors for click beetle luciferase were included in the plasmid. The results establish that, although intravenously infused T cells accumulate at high levels in the spleen and the liver, they inefficiently traffic to KPC tumor sites (FIG. 2G), yielding a modest 4-day survival advantage compared to untreated control animals (FIG. 2H). Furthermore, Rae-1 target antigen expression levels were only slightly lower following infusion of CAR-T cells when compared to control lymphocytes (FIG. 2I).

Figure 3A:
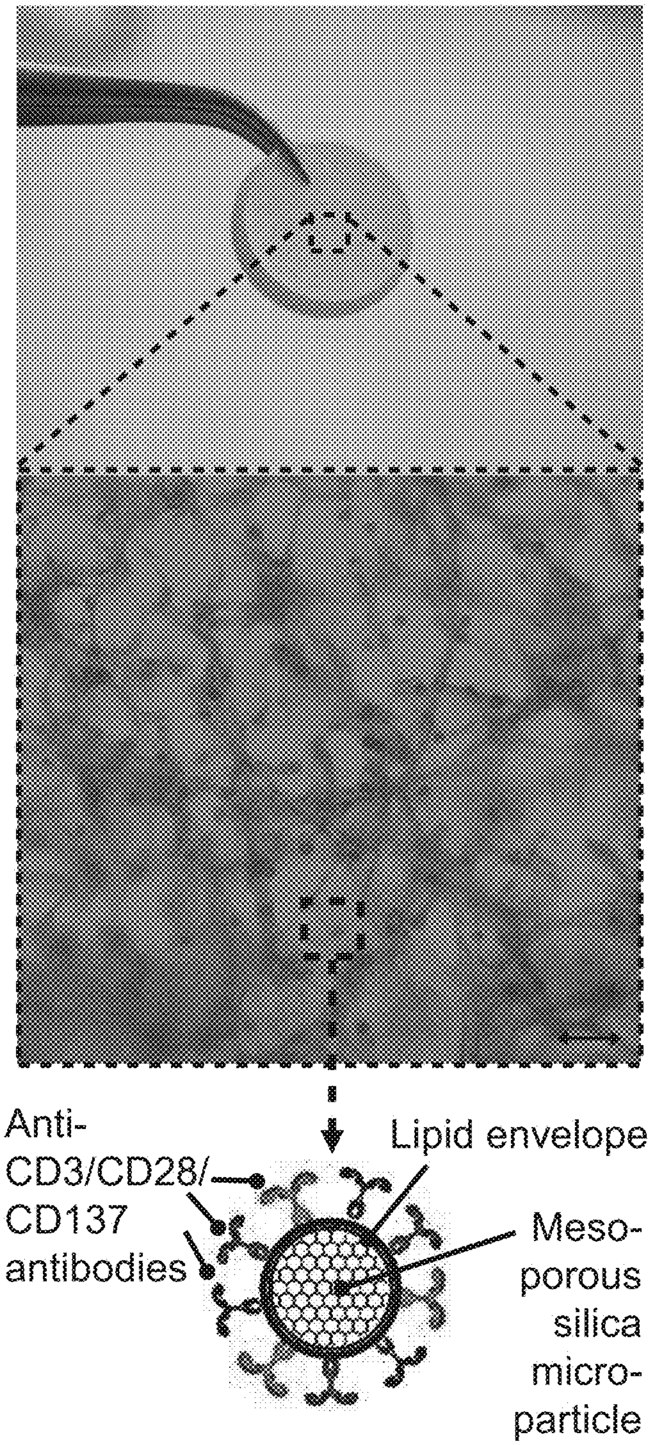
FIGS. 3A, 3B. Biomatrices placed directly on pancreatic tumors can function as an effective delivery platform for CAR-programmed T cells.
Figure 3B:
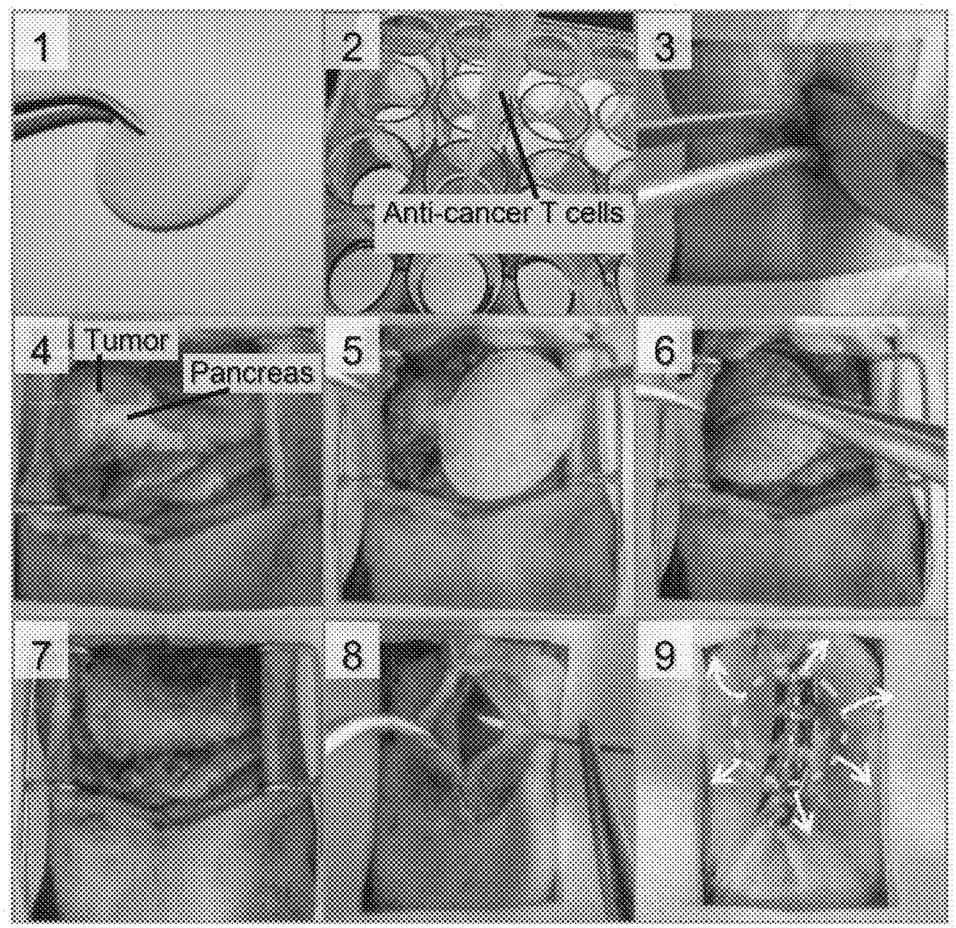
Figure 4A:
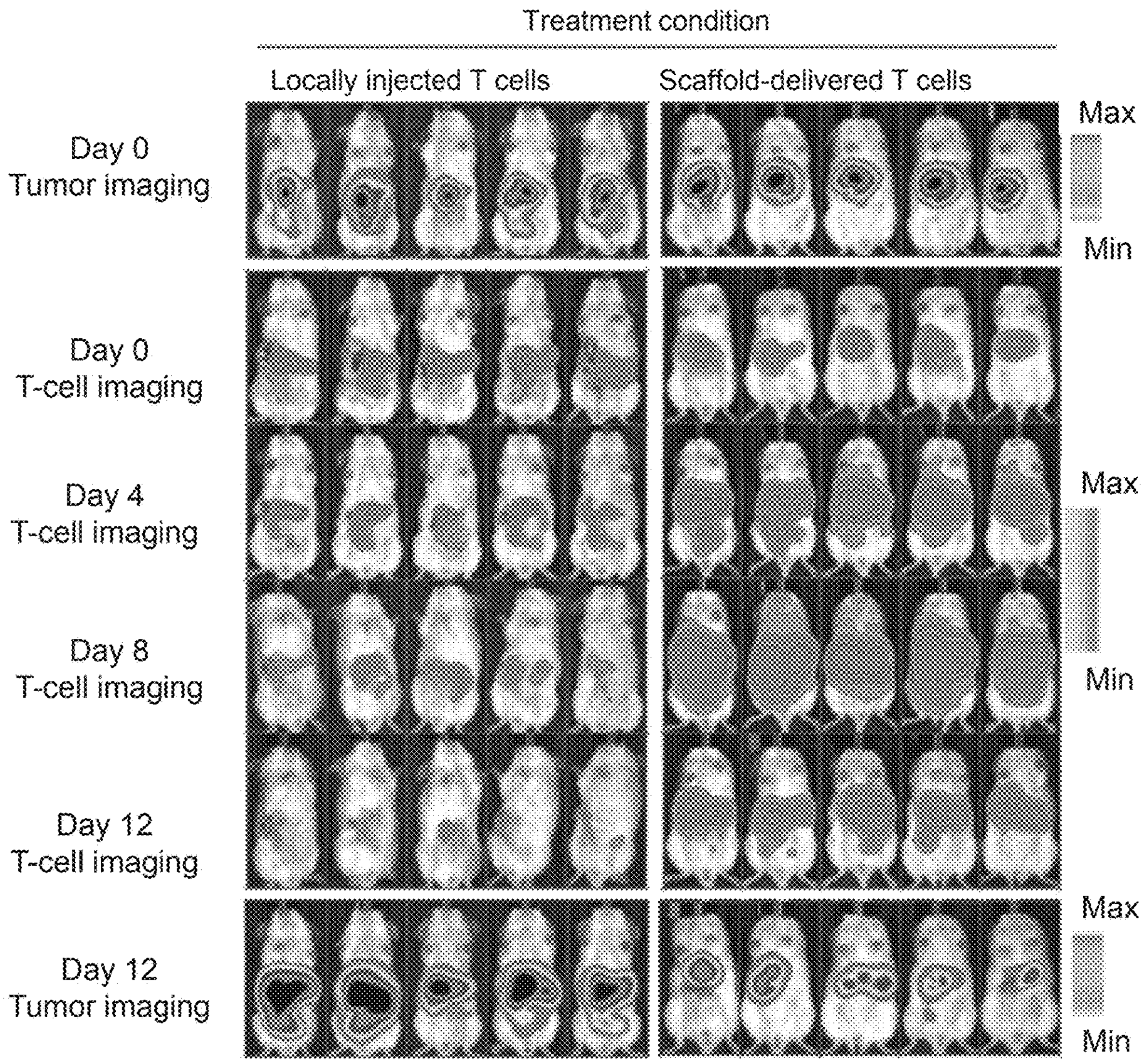
FIGS. 4A-4E. Polymer-launched CAR-T cells robustly expand at the tumor site and trigger tumor regression, but do not affect cells missing the target antigen.
Figure 4B:
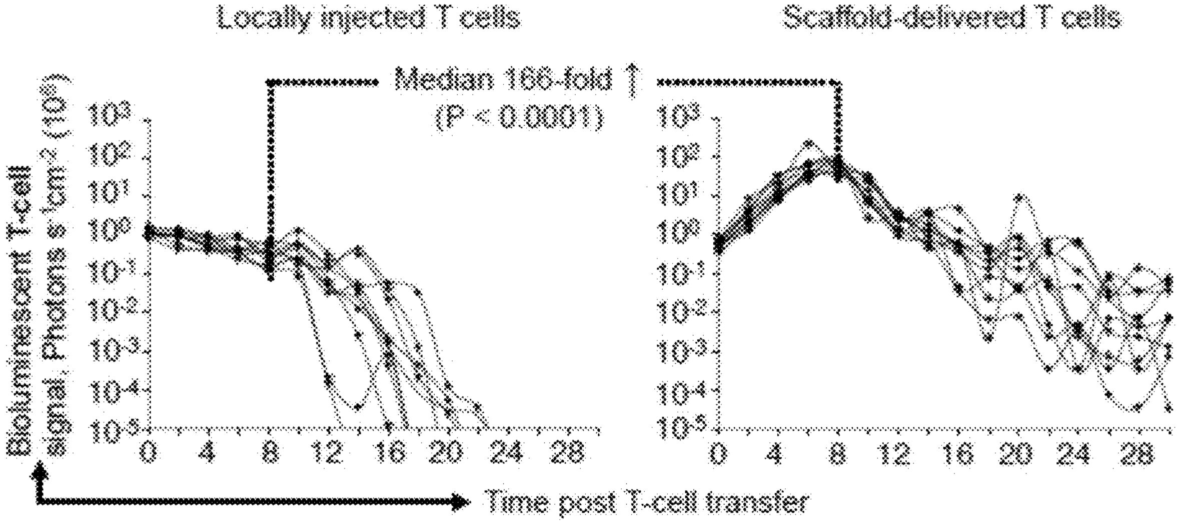
Figure 4C:
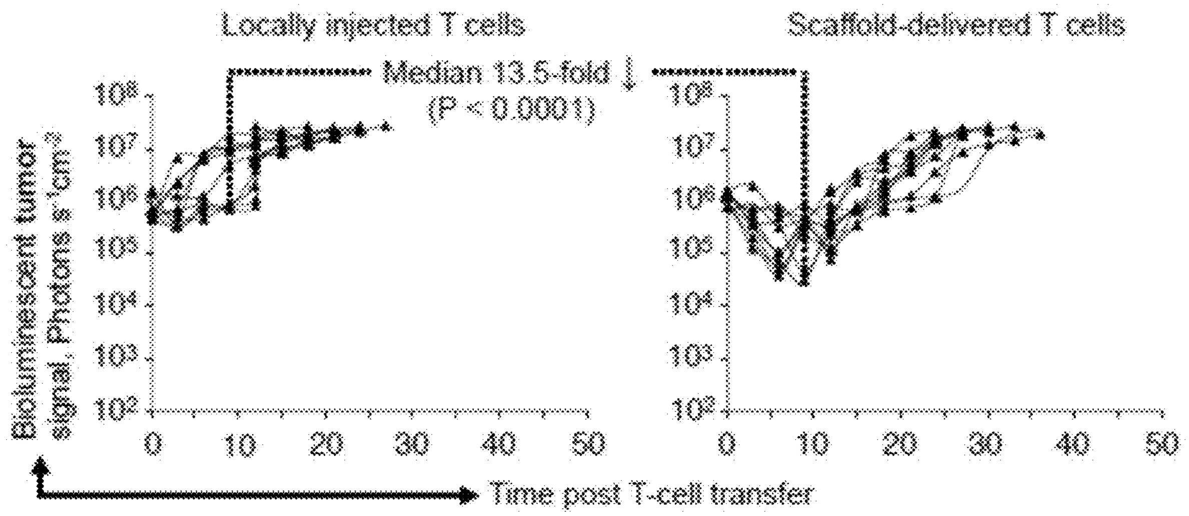
Figure 4D:
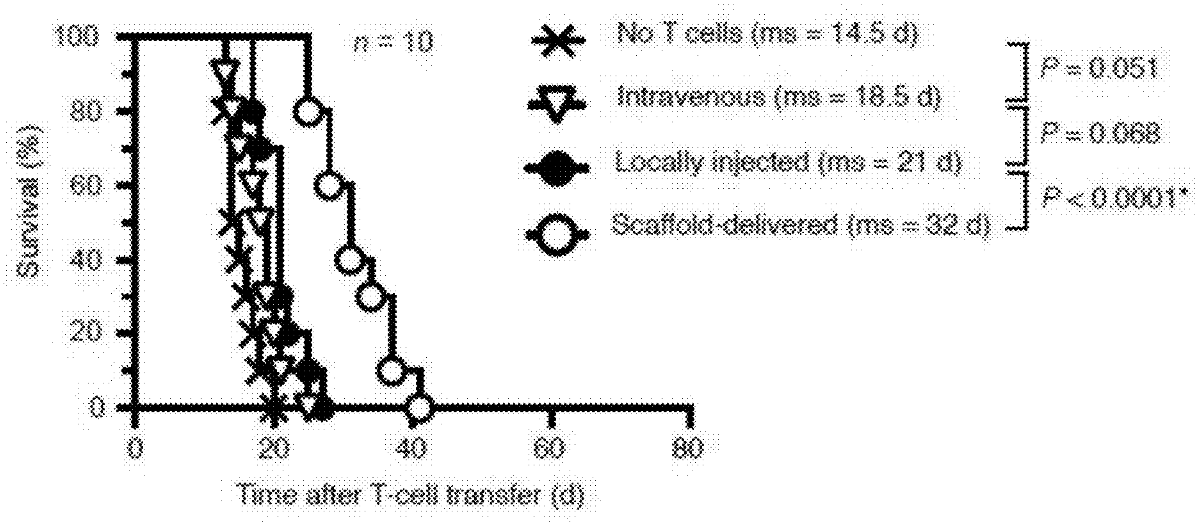
Figure 4E:
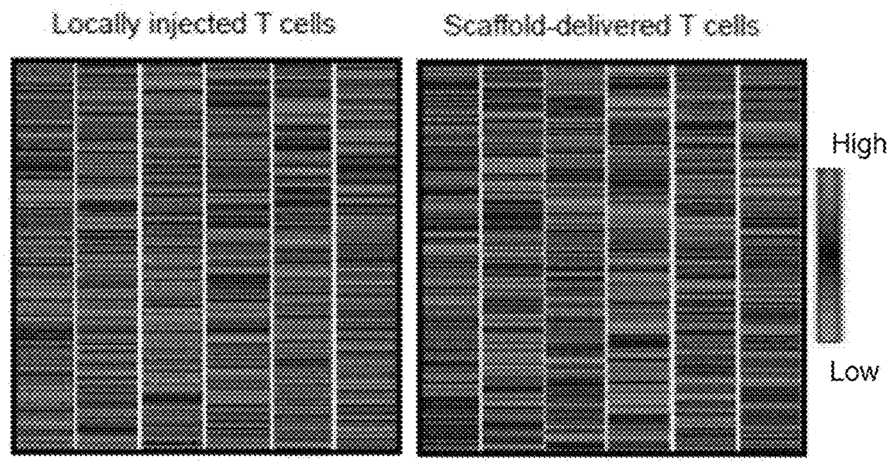

Delivery via bioactive carriers substantially improves T cell expansion and function at the tumor site, but antigen-negative tumor subtypes escape elimination by these cells. The results described above prompted exploration of the potential of using biomaterials for the localized delivery of tumor-reactive T cells to pancreatic tumor sites, and to create ways to sustain them. A method to embed cancer-fighting immune cells in a resorbable polymeric device that can be surgically implanted where a tumor has been excised, or upon one that is non-resectable (FIG. 3A) was recently developed and is described in US2016/0008399 and Stephan, et al., Nat Biotechnol 33, 97-101 (2015). Already at their target site, the delivered lymphocytes begin eliminating cancer cells immediately. The porous scaffolds are created from polymerized alginate, a castable, naturally-occurring polysaccharide that has been approved by the FDA for human use because of its exceptional biocompatibility and biodegradability. Baldwin & Kiick, Biopolymers 94, 128-140 (2010). To enable them to function as efficient delivery vehicles for active T cells, these devices were augmented with migration-promoting macromolecules (e.g., collagen-mimetic peptide) and stimulatory cues (e.g., embedded microparticles displaying anti-CD3, anti-CD28, and anti CD137 antibodies; FIG. 3A). Ten days after introducing the luciferase-expressing KPC tumor cells, scaffolds containing $7\times10^{6}$ NKG2D-CAR+ T cells were implanted directly on top of the resulting pancreatic tumors (FIG. 3B). A second group received the same dose of cells injected directly into the tumor, and control mice received no treatment. Bioluminescence imaging was used to quantify tumor growth and, in parallel experiments, to track tissue distribution, expansion, and persistence of the lymphocytes. It was found that the CAR-T cells injected directly into pancreatic tumors persisted poorly in the immunosuppressive microenvironment and only produced a temporary delay in disease progression (21 days compared to 14.5 days median overall survival in the untreated control group, FIGS. 4A-4D). By contrast, T cells delivered from implanted scaffolds underwent significant proliferation at the tumor site (166-fold higher peak photon count relative to injected T cells on day 8, $P<0.0001$, FIGS. 4A, 4B) and substantially reduced KPC tumor growth (FIGS. 4A, 4C). However, even though they more than doubled the survival of treated mice, T cell-loaded scaffolds failed to completely clear the disease as all mice eventually developed Rae-1 low/negative immune-escape variants (FIG. 4E).

Figure 6A:
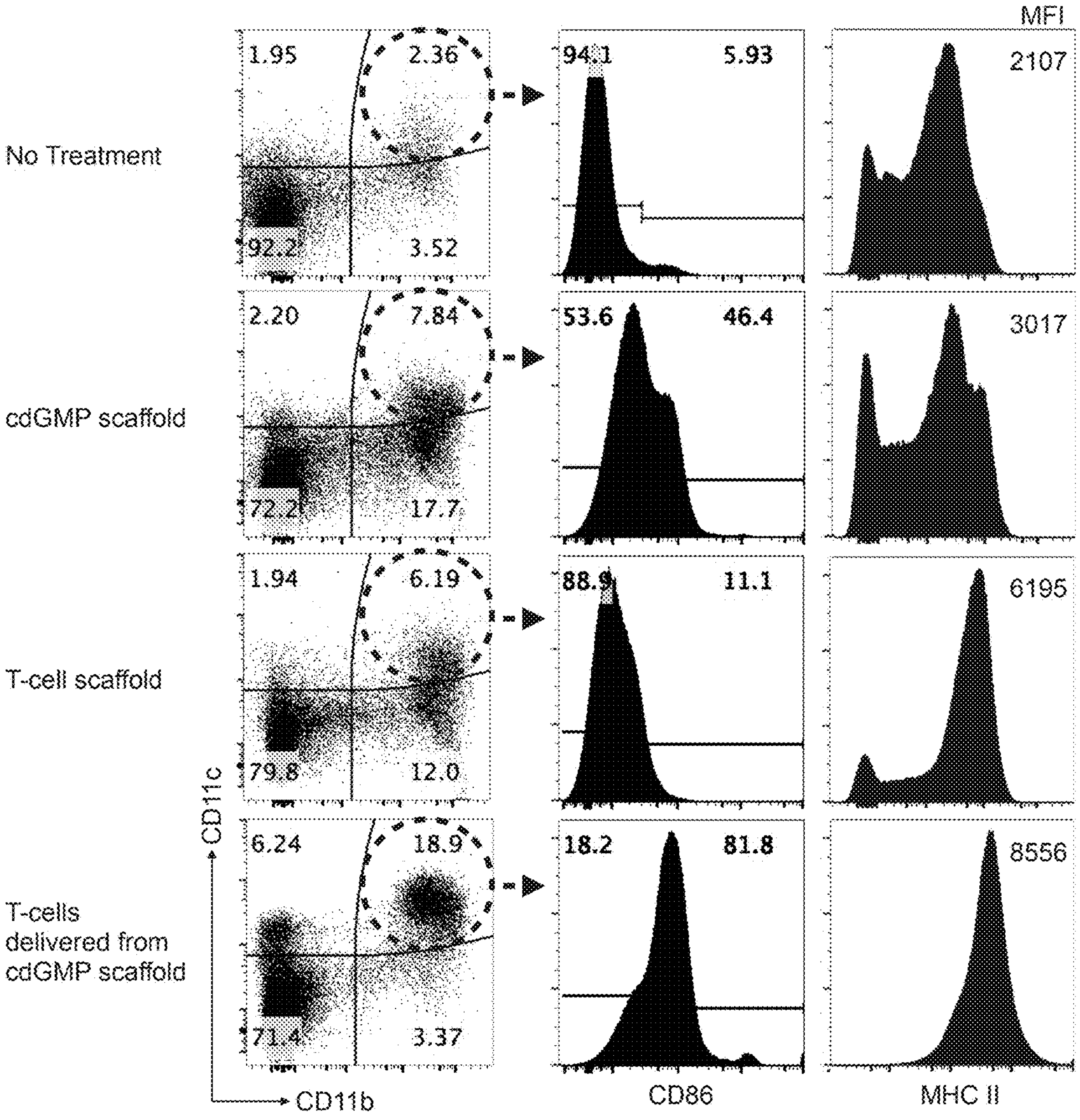
FIGS. 6A, 6B. Scaffold-released CAR-T cells and STING agonist synergize to activate host antigen-presenting cells.
Figure 6B:
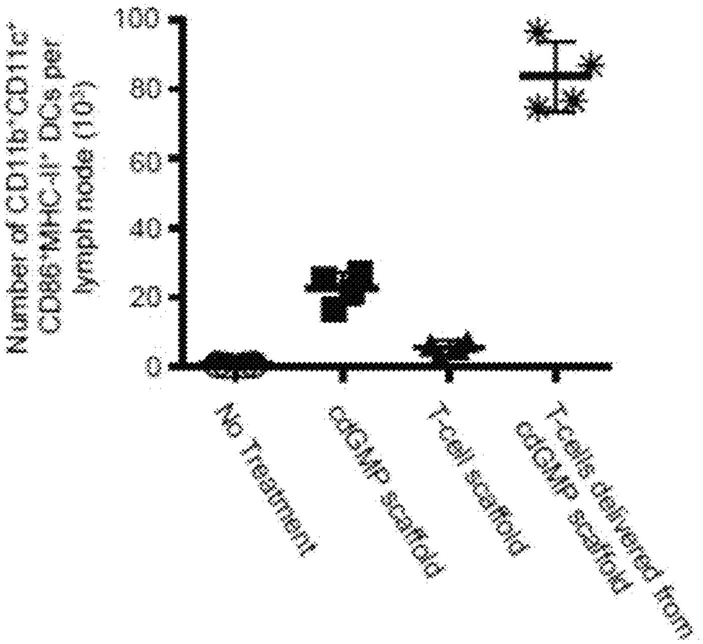

Combined release of CAR-T cells and STING agonist from scaffolds results in synergistic maturation and activation of host antigen-presenting cells. The observations described above indicate that targeting a single antigen with CAR-T cells is unlikely to protect against the outgrowth of antigen-negative cells—even when the tumor is saturated with optimally stimulated anti-cancer T cells delivered from an implantable scaffold. Accordingly, it was next sought to synergistically launch host T cell responses in an effort to eliminate residual CAR-resistant tumor cell types (see FIG. 5A). An intact immune system is able to generate effective tumor-specific responses, but it requires stimulation to do so. Unfortunately, tumors inhibit the maturation and activation of antigen-presenting cells located in their draining lymph nodes, and thereby prevent tumor-reactive T cells from differentiating into cytolytic effectors. In an effort to reverse this suppression, the scaffolds were used to achieve high local concentrations of the immune-stimulatory STING agonist cyclic-di-GMP (c-diGMP) in order to render the tumor milieu more conducive for T cell priming via the recruitment and stimulation of antigen-presenting cells (FIG. 5B). Dendritic cells (DCs), defined by their high expression of the major histocompatibility complex class II (MHC-II) and T cell costimulatory molecules (e.g., CD86), are the most potent antigen-presenting cells and are capable of orchestrating an adaptive anti-tumor immune response. Immune phenotyping of tumor-associated lymph nodes associated with established KPC tumors revealed that less than 6% of their DCs (recognized in flow cytometry as CD11c+ CD11b+) were appropriately activated, as evidenced by their expression of CD86; the majority of the DCs were tolerogenic (CD86-negative; FIG. 6A). Releasing only c-diGMP from implanted scaffolds upregulated CD86 and MHC-II expression by a large proportion of these DCs, and increased their overall frequency in the draining lymph nodes 38-fold (FIG. 6B). Following implantation of CAR-T cell-loaded scaffolds fabricated without the STING agonist, numbers of CD11c+CD86+ mature DCs increased only modestly (9.4-fold), but the MHC-II expression levels on these cells was more than twice as high compared to the c-diGMP treatment group (FIG. 6A, 6B). Release of both c-diGMP and CAR-T cells from implanted matrices produced a synergistic activation of DCs, reflected by robust increases in the frequencies of activated DCs (3.7-fold higher compared to c-diGMP alone). Notably, these cells expressed high levels of costimulatory molecules as well as MHC-II, indicating that they can efficiently cross-present tumor antigens and launch anti-tumor T cell responses (FIG. 6B).

Figure 7A:
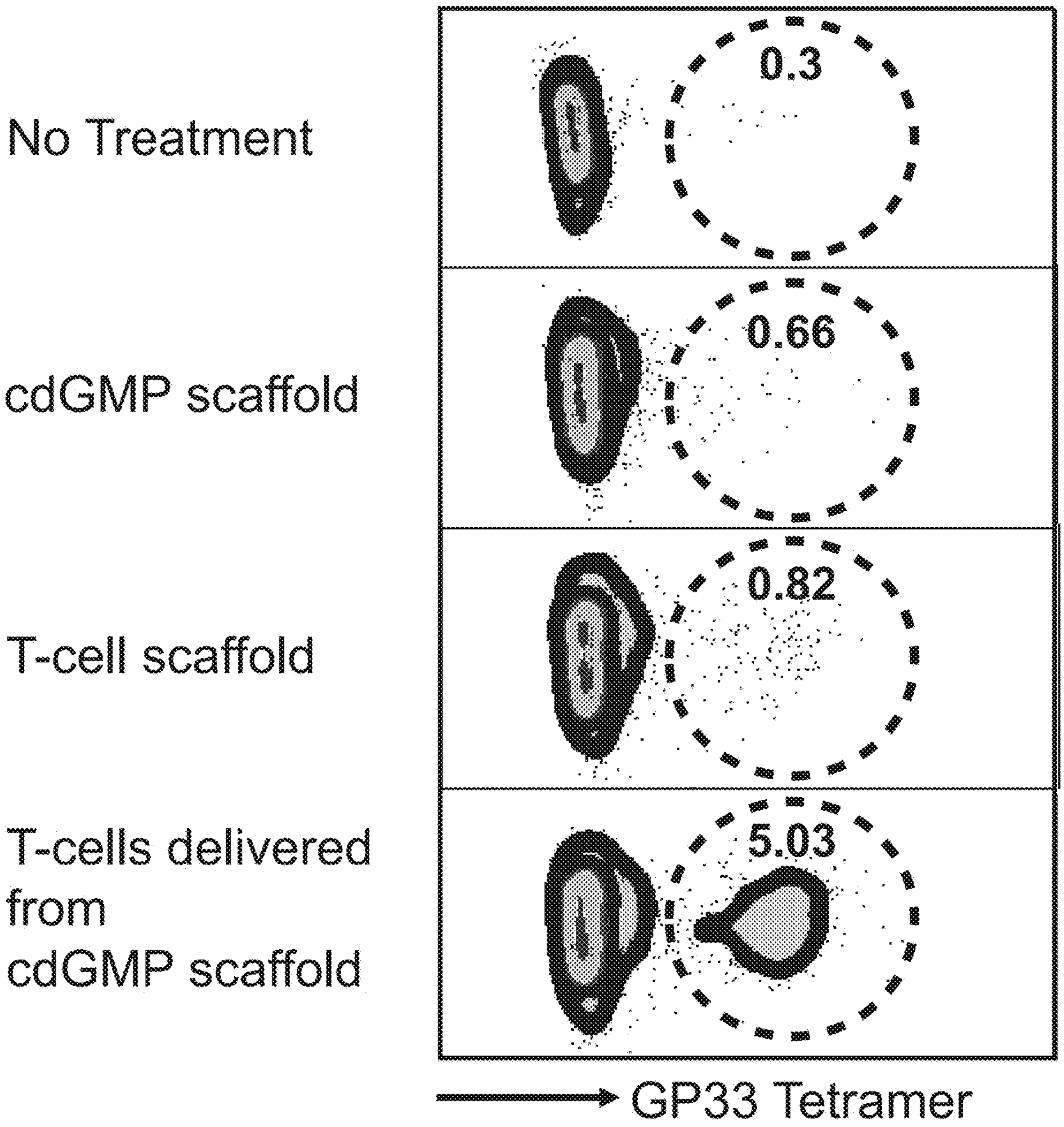
FIGS. 7A, 7B. Co-release of c-diGMP along with CAR-expressing T cells from scaffolds primes endogenous tumor-reactive lymphocytes.
Figure 7B:
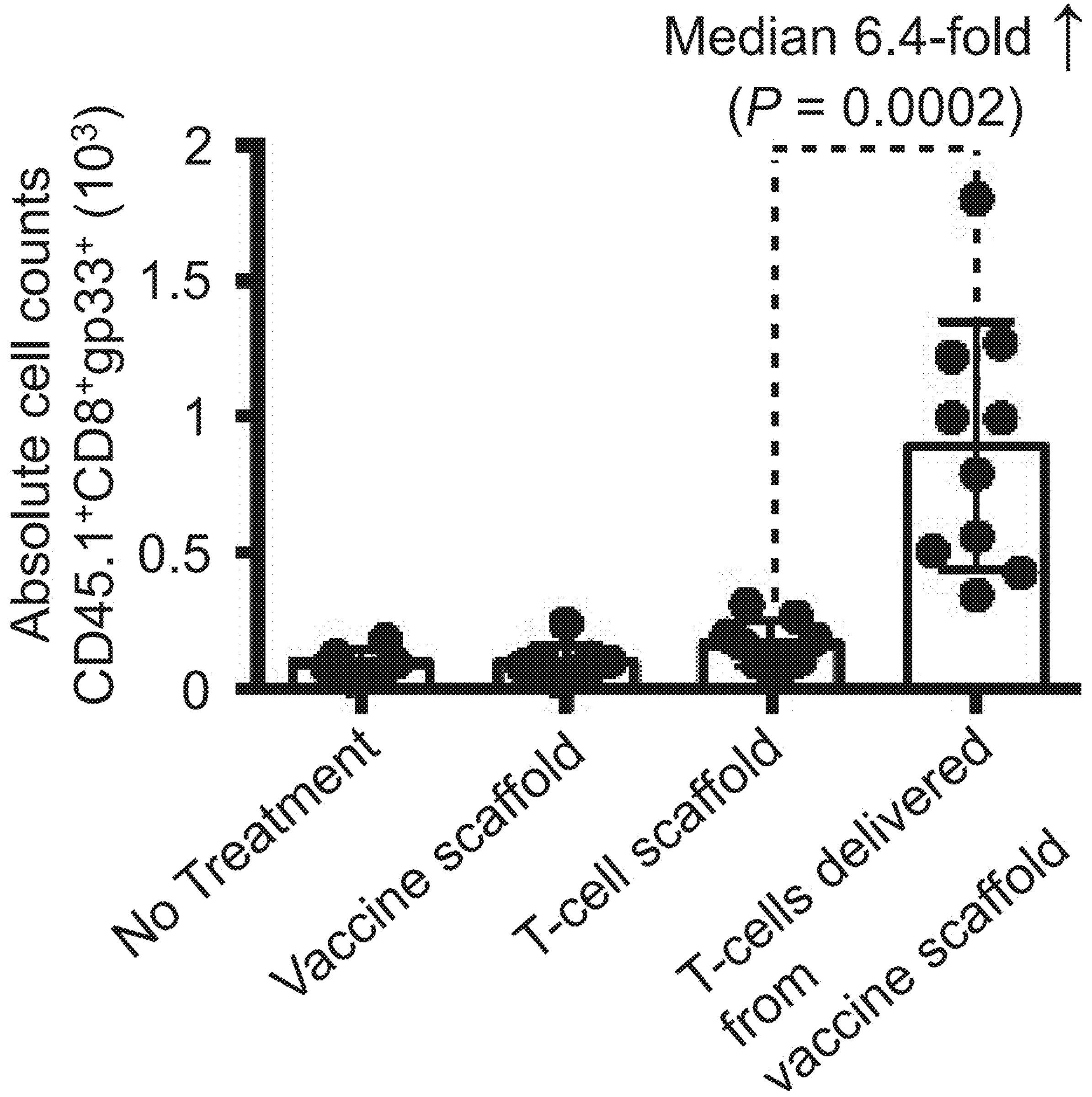

Combined CAR-T cell/STING agonist therapy primes robust tumor-specific host lymphocyte responses. To measure activation of tumor-specific T cells in the host, a KPC pancreatic tumor model that expresses the lymphocytic choriomeningitis virus (LCMV) glycoprotein gp33 was used. As a surrogate pancreatic tumor antigen, this protein enabled use of flow cytometry to analyze how the scaffolds affect the frequency of tetramer-positive cells among CD8+ T cells. In order to distinguish between scaffold-delivered and endogenous T cells, the donor cells were genetically tagged with a CD45.2 marker and CD45.1-transgenic mice were used as hosts. Mice were treated with biomaterial scaffolds engineered to release either c-diGMP, CAR-T cells, or a combination of the two into the tumor. Control mice received no treatment. As expected, spontaneous anti-tumor T cell responses rarely occurred in untreated mice (FIG. 7A), establishing that, despite their expression of the gp33 xenoantigen, KPC-gp33 tumors continue to be highly immunosuppressive. Treatment with c-diGMP-loaded scaffolds or those prepared with lymphocytes alone produced host antitumor T cell activities, although the overall response was modest (1.3-fold and 2-fold increased numbers in peripheral blood gp33 tetramer-positive T cells, respectively; FIGS. 7A, 7B). By contrast, the combination of c-diGMP and CAR-expressing T cells elicited synergistic antitumor responses, which were on average 6.4-fold higher than implants releasing the lymphocytes only (FIGS. 7A, 7B).

Figure 8A:
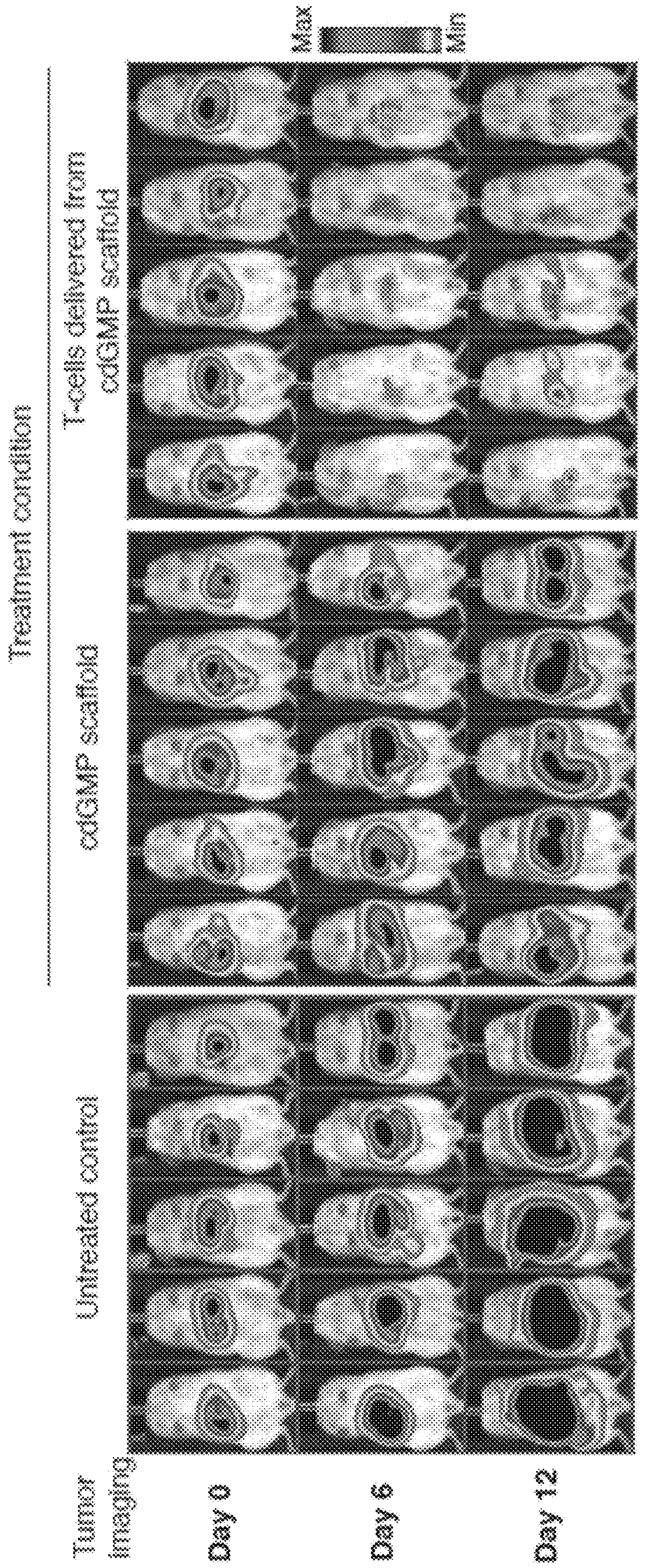
FIGS. 8A-8C. Scaffolds that co-deliver STING agonists along with CAR-expressing T cells can limit tumor immune escape.
Figure 8B:
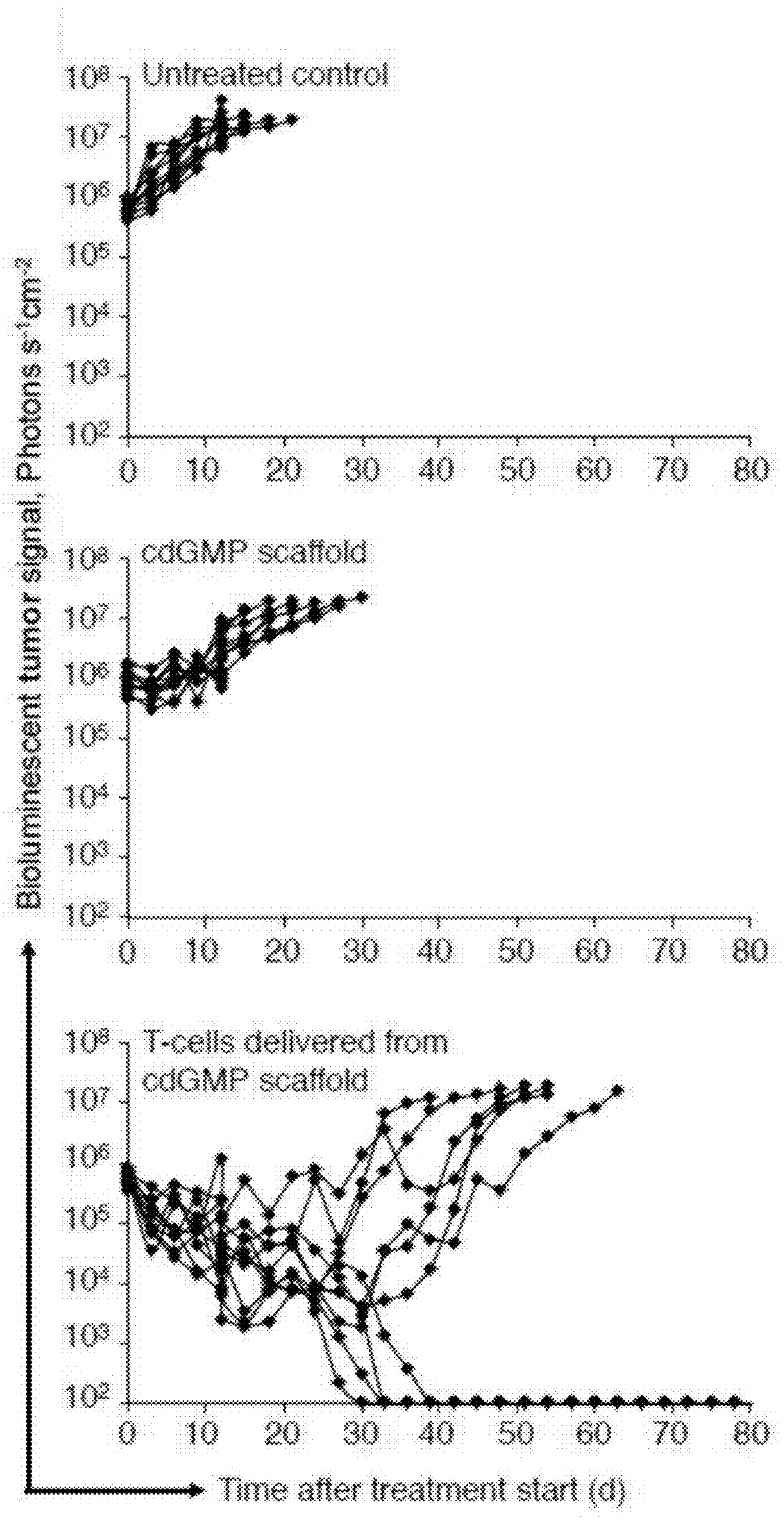
Figure 8C:
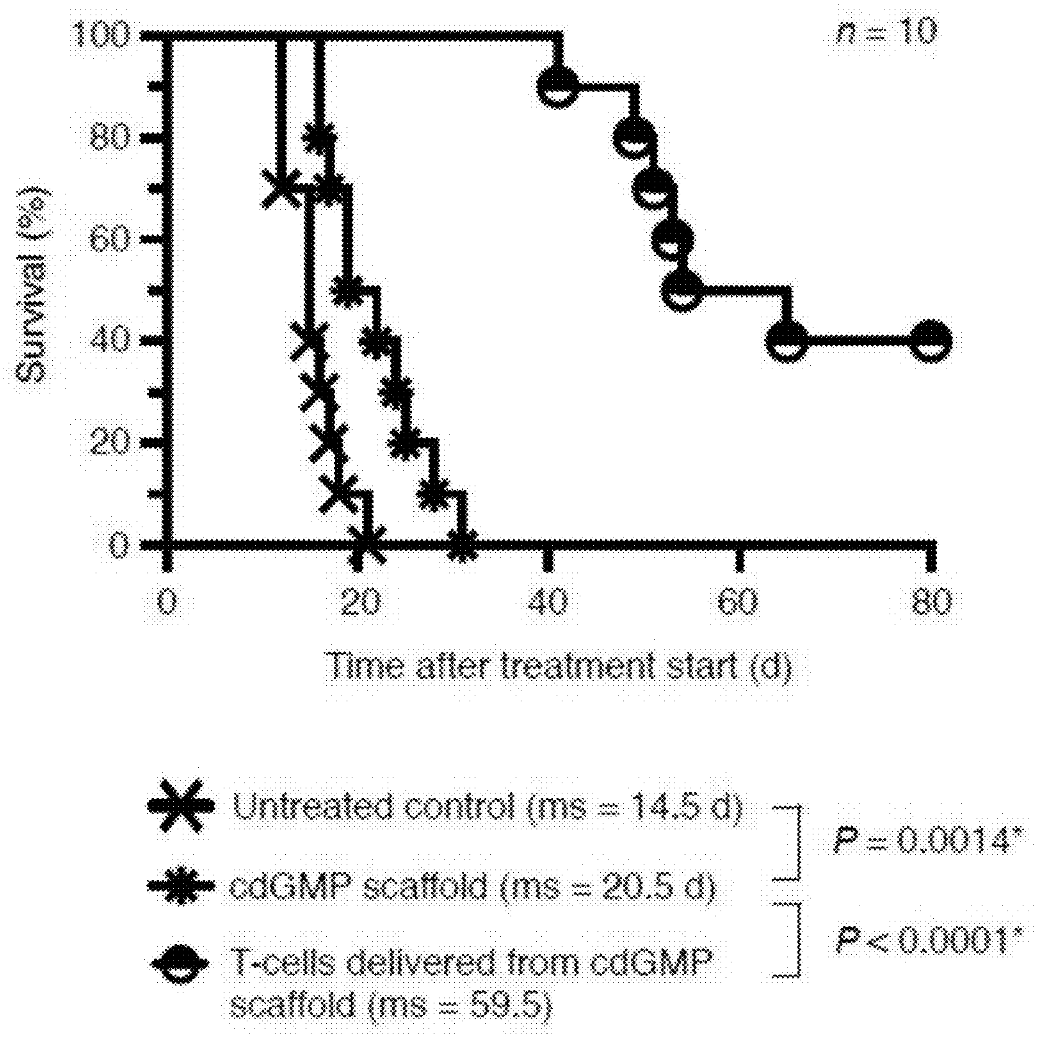

Scaffolds can trigger host antitumor immunity sufficient to clear tumors and eliminate metastases. To measure the anti-tumor benefits provided by scaffolds that co-deliver the STING agonist along with CAR-programmed T cells, mice bearing orthotopic KPC tumors were treated using scaffolds functionalized with either c-diGMP alone, or with both c-diGMP and CAR-T cells; control mice received no treatment. Tumor growth was quantified by serial bioluminescence imaging. It was found that the combined release of CAR-T cells and c-diGMP from scaffolds eradicated KPC tumors in four of ten treated mice (FIGS. 8A-8C), and the other six showed substantial tumor regression with an average 37-day improvement in survival. Although the STING agonist alone never produced complete clearance, it increased survival by 6 days compared to the control group. To determine if the scaffolds elicit global antitumor immunity, the four mice that experienced complete tumor regression (FIGS. 9A, 9B) were re-challenged with a systemic dose of $10^4$ luciferase-expressing KPC tumor cells; tumor-naïve mice were used as controls. Bioluminescence imaging was then used to quantify differences in growth rates of lung metastases between the treatment groups. The results establish that all mice cured with CAR-T cell/STING agonist immunotherapy were fully protected from this re-challenge, with no measurable tumor mass 4 weeks after the KPC cells were administered. By contrast, control animals quickly formed metastatic foci in their lungs and rapidly succumbed to their disease (FIG. 9B). Thus, appropriately formulated combination therapy using CAR-programmed T cells and STING agonists can eliminate local tumors and trigger systemic host antitumor immunity powerful enough to prevent untreated distant metastases.

This work demonstrates a new concept in cancer therapy that achieves both rapid tumor clearance and systemic antitumor immunity. The developed scaffolds enable surgeons to deliver cancer-fighting lymphocytes along with potent STING agonists directly to tumors at high local concentrations and over an extended period of time. This will not only maximize treatment successes following, for example, pancreatic tumor surgery, but will also reduce healthcare costs because a single treatment with the disclosed scaffolds is likely to spare patients from complicated second or third surgeries, costly extended hospital stays, cycles of radiation and chemotherapy, and expensive palliative care. More broadly, this platform can eventually shift the focus from broad-impact chemical and radiation-based approaches to tumor-specific immunotherapeutics by providing surgeons with an appropriate tool to easily and safely apply treatments directly to a solid tumor.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the anti-tumor effects of a claimed scaffold or method in at least two measures of anti-tumor activity disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

The invention claimed is:

1. A lymphocyte scaffold comprising (i) genetically-reprogrammed lymphocytes disposed within a scaffold matrix at a density of at least $7\times10^6$ genetically-reprogrammed lymphocytes per $cm^2$, the scaffold matrix comprising thin film nitinol (TFN) micromesh, (ii) a lymphocyte-adhesion moiety comprising fibrin, and (iii) lymphocyte-activating moieties comprising antibodies specific for CD137, wherein the lymphocyte-activating moieties are covalently coupled to the scaffold matrix.

2. The lymphocyte scaffold of claim 1, wherein the genetically-reprogrammed lymphocytes comprise T cells and the lymphocyte-activating moieties comprise antibodies specific for CD3, CD28 and CD137.

3. The lymphocyte scaffold of claim 1, wherein the genetically-reprogrammed lymphocytes comprise natural killer (NK) cells and the lymphocyte-activating moieties comprise interleukin 15 and antibodies specific for CD137.

4. The lymphocyte scaffold of claim 1, wherein the genetically-reprogrammed lymphocytes comprise T cells and NK cells and the lymphocyte-activating moieties comprise antibodies specific for CD137.

5. The lymphocyte scaffold of claim 1, further comprising a STING agonist.

6. The lymphocyte scaffold of claim 5, wherein the STING agonist comprises c-diGMP, c-diAMP, c-GAMP, c-AIMP, (3',2')c-AIMP, (2',2')c-AIMP, (2',3')c-AIMP, c-AIMP(S), c-(dAMP-dIMP), c-(dAMP-2'FdIMP), c-(2'FdAMP-2'FdIMP), (2',3')c-(AMP-2'FdIMP), c-[2'FdAMP(S)-2'FdIMP(S)], c-[2'FdAMP(S)-2'FdIMP(S)](POM)2, and/or 5,6-dimethylxanthenone-4-acetic acid (DMXAA).

7. The lymphocyte scaffold of claim 6, wherein the STING agonist comprises c-diGMP.

8. The lymphocyte scaffold of claim 5, wherein the STING agonist is embedded within a drug eluting polymer coated onto the surface of the TFN micromesh.

9. The lymphocyte scaffold of claim 1, wherein the TFN micromesh comprises a surface-modified layer and the lymphocyte-activating moieties are covalently coupled to the surface of the TFN layer.

10. The lymphocyte scaffold of claim 1, wherein the TFN micromesh comprises a multilayer mesh architecture configured to retain multiple layers of genetically-reprogrammed lymphocytes within a single micromesh layer.

* * * * *